(12) United States Patent
Carl et al.

(10) Patent No.: US 9,744,140 B2
(45) Date of Patent: *Aug. 29, 2017

(54) PHARMACEUTICALS FOR ORAL DELIVERY

(71) Applicant: Enteris BioPharma, Inc., Boonton, NJ (US)

(72) Inventors: Stephen M. Carl, Budd Lake, NJ (US); John Stanley Vrettos, Union, NJ (US); William Stern, Tenafly, NJ (US)

(73) Assignee: Enteris Biopharma, Inc., Boonton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/353,213

(22) Filed: Nov. 16, 2016

(65) Prior Publication Data

US 2017/0056328 A1    Mar. 2, 2017

Related U.S. Application Data

(63) Continuation of application No. 15/184,971, filed on Jun. 16, 2016, now Pat. No. 9,526,785, which is a continuation of application No. 14/197,405, filed on Mar. 5, 2014, now Pat. No. 9,457,086.

(60) Provisional application No. 61/772,927, filed on Mar. 5, 2013, provisional application No. 61/925,443, filed on Jan. 9, 2014.

(51) Int. Cl.

| | |
|---|---|
| *A61K 31/65* | (2006.01) |
| *A61K 31/351* | (2006.01) |
| *A61K 31/7036* | (2006.01) |
| *A61K 9/52* | (2006.01) |
| *A61K 9/48* | (2006.01) |
| *A61K 47/18* | (2017.01) |
| *A61K 31/216* | (2006.01) |
| *A61K 47/12* | (2006.01) |
| *A61K 47/10* | (2017.01) |
| *A61K 47/14* | (2017.01) |
| *A61K 31/122* | (2006.01) |
| *A61K 31/397* | (2006.01) |
| *A61K 31/64* | (2006.01) |
| *A61K 31/7012* | (2006.01) |
| *A61K 9/00* | (2006.01) |

(52) U.S. Cl.
CPC .......... *A61K 9/4891* (2013.01); *A61K 9/0019* (2013.01); *A61K 9/0053* (2013.01); *A61K 9/4858* (2013.01); *A61K 9/4866* (2013.01); *A61K 31/122* (2013.01); *A61K 31/216* (2013.01); *A61K 31/351* (2013.01); *A61K 31/397* (2013.01); *A61K 31/64* (2013.01); *A61K 31/65* (2013.01); *A61K 31/7012* (2013.01); *A61K 31/7036* (2013.01); *A61K 47/10* (2013.01); *A61K 47/12* (2013.01); *A61K 47/14* (2013.01); *A61K 47/183* (2013.01); *A61K 47/186* (2013.01)

(58) Field of Classification Search
None
See application file for complete search history.

(56) References Cited

U.S. PATENT DOCUMENTS

| | | |
|---|---|---|
| 2,956,926 A | 10/1960 | Grief |
| 5,789,234 A | 8/1998 | Bertelsen et al. |
| 5,912,014 A | 6/1999 | Stern et al. |
| 6,086,918 A | 7/2000 | Stern et al. |
| 6,103,495 A | 8/2000 | Mehta et al. |
| 6,210,925 B1 | 4/2001 | Mehta et al. |
| 6,627,438 B2 | 9/2003 | Mehta et al. |
| 6,673,574 B2 | 1/2004 | Stern et al. |
| 6,737,250 B2 | 5/2004 | Mehta et al. |
| 7,316,819 B2 | 1/2008 | Crotts et al. |
| 7,445,911 B2 | 11/2008 | Consalvo et al. |
| RE40,812 E | 6/2009 | Stern |
| 7,553,655 B2 | 6/2009 | Mehta et al. |
| 7,666,446 B2 | 2/2010 | Choi et al. |
| 7,968,311 B2 | 6/2011 | Mehta et al. |
| 8,088,734 B2 | 1/2012 | Mehta et al. |
| 8,093,207 B2 | 1/2012 | Stern et al. |
| 8,163,871 B2 | 4/2012 | Consalvo et al. |
| 8,216,822 B2 | 7/2012 | Mehta et al. |
| 8,227,241 B2 | 7/2012 | Mehta et al. |
| RE43,580 E | 8/2012 | Stern |
| 8,252,580 B2 | 8/2012 | Mehta et al. |
| 8,377,863 B2 | 2/2013 | Stern et al. |
| 8,513,183 B2 | 8/2013 | Stern et al. |
| 8,592,366 B2 | 11/2013 | Stern et al. |

(Continued)

FOREIGN PATENT DOCUMENTS

| | | |
|---|---|---|
| WO | 97/33531 | 9/1997 |
| WO | 98/46722 | 10/1998 |

(Continued)

OTHER PUBLICATIONS

International Preliminary Report on Patentability issued in International Application No. PCT/US2014/020763 dated Sep. 17, 2015.
PCT International Search Report and Written Opinion issued in International Application No. PCT/US2014/020763 dated Jun. 6, 2014.
Non-Final Office Action in U.S. Appl. No. 14/197,405 dated Oct. 23, 2014.
Final Office Action in U.S. Appl. No. 14/197,405 dated Mar. 2, 2015.
Non-Final Office Action in U.S. Appl. No. 14/197,405 dated Jul. 28, 2015.
Non-Final Office Action in U.S. Appl. No. 14/197,405 dated Jan. 5, 2016.

(Continued)

*Primary Examiner* — Jessica Worsham
(74) *Attorney, Agent, or Firm* — Greenberg Traurig, LLP; David J. Dykeman; Natalie Salem

(57) ABSTRACT

The present invention provides pharmaceutical compositions suitable for oral delivery and methods of treating subjects in need thereof. The pharmaceutical compositions of the present invention enhance bioavailability of at least one compound classified as BCS Class II, BCS Class III or BCS Class IV.

18 Claims, 57 Drawing Sheets

(56) References Cited

U.S. PATENT DOCUMENTS

| | | |
|---|---|---|
| 8,664,178 B2 | 3/2014 | Stern et al. |
| 8,815,583 B2 | 8/2014 | Miller et al. |
| 8,835,161 B2 | 9/2014 | Mehta et al. |
| 8,835,377 B2 | 9/2014 | Mehta et al. |
| 9,399,017 B2 | 7/2016 | Stern et al. |
| 2005/0215476 A1 | 9/2005 | Mehta et al. |
| 2007/0243244 A1 | 10/2007 | Shah et al. |
| 2009/0317462 A1 | 12/2009 | Stern et al. |
| 2010/0256060 A1 | 10/2010 | Stern |
| 2011/0045029 A1 | 2/2011 | Choi et al. |
| 2012/0071410 A1 | 3/2012 | Mehta et al. |
| 2013/0072446 A1 | 3/2013 | Consalvo et al. |
| 2013/0171248 A1 | 7/2013 | Choi et al. |
| 2013/0345134 A1 | 12/2013 | Sauerberg et al. |
| 2014/0249085 A1 | 9/2014 | Mehta et al. |
| 2014/0255479 A1 | 9/2014 | Carl et al. |
| 2014/0335169 A1 | 11/2014 | Stern et al. |
| 2015/0125522 A1 | 5/2015 | Mehta et al. |
| 2016/0199303 A1 | 7/2016 | Vrettos et al. |
| 2016/0296624 A1 | 10/2016 | Carl et al. |

FOREIGN PATENT DOCUMENTS

| | | |
|---|---|---|
| WO | 01/56594 | 8/2001 |
| WO | 02/43767 | 6/2002 |
| WO | 02/072075 | 9/2002 |
| WO | 02/087621 | 11/2002 |
| WO | 2004/064758 | 8/2004 |
| WO | 2005/089182 | 9/2005 |
| WO | 2006/026592 | 3/2006 |
| WO | 2006/058225 | 6/2006 |
| WO | 2007/002532 | 1/2007 |
| WO | 2007/070450 | 6/2007 |
| WO | 2007/075792 A1 | 7/2007 |
| WO | 2008/150426 | 12/2008 |
| WO | 2012/174117 | 12/2012 |
| WO | 2012/174397 | 12/2012 |
| WO | 2014/138241 | 9/2014 |

OTHER PUBLICATIONS

Final Office Action in U.S. Appl. No. 14/197,405 dated May 4, 2016.

Bastin, Richard et al.; "Salt Selection and Optimisation Procedures for Pharmaceutical New Chemical Entities", Organic Process Research and Development, vol. 4, No. 5, pp. 427-435, 2000.

Constantinides, P. et al., "Considerations and recommendations on traditional and non-traditional uses of excipients in oral drug products", AAPS Open 2:3, pp. 1-6 (May 10, 2016).

PHARMACEUTICALS FOR ORAL DELIVERY

CROSS-REFERENCE TO RELATED APPLICATIONS

This application is a continuation of U.S. application Ser. No. 15/184,971, filed on Jun. 16, 2016, which is a continuation of U.S. application Ser. No. 14/197,405, filed on Mar. 5, 2014, now U.S. Pat. No. 9,457,086, which claims priority to and the benefit of U.S. Provisional Application No. 61/772,927, filed Mar. 5, 2013 and U.S. Provisional Application No. 61/925,443, filed Jan. 9, 2014. The contents of each of these applications are incorporated herein by reference in their entirety.

BACKGROUND OF THE INVENTION

The biopharmaceutical classification system ("BCS") guidance was published in 2000 by the U.S. Food and Drug Administration ("FDA"), to standardize oral formulation development that currently forms the basis of the scientific framework used for classifying drug substances based on their aqueous solubility and intestinal permeability. According to the BCS, drug substances are classified into four classes based solely on their solubility and intestinal permeability: Class I: High Solubility, High Permeability; Class II: Low Solubility, High Permeability; Class III: High Solubility, Low Permeability and Class IV: Low Solubility, Low Permeability. Poor solubility leads to significant hurdles in the oral absorption and bioavailability of the drug candidate by decreasing its dissolution rate and membrane permeation. Permeability across biological membranes is a key factor in the absorption and distribution of drugs. Poor permeability can lead to poor absorption across the gastrointestinal mucosa or poor distribution throughout the body.

Poor oral bioavailability ("F") is one of the leading causes of compound failure in preclinical and clinical development. Compounds with poor oral F tend to have low plasma exposure and high interindividual variability, which limits their therapeutic usefulness. Thus, there is a need in the art for pharmaceutical compositions that improve oral bioavailability. The present invention addresses these needs.

SUMMARY OF THE INVENTION

The present invention provides a pharmaceutical composition suitable for oral delivery including at least one compound classified as BCS Class II, BCS Class III or BCS Class IV; at least one absorption enhancer; at least one pH lowering compound; and at least one chelating agent.

The present invention also provides methods for enhancing the bioavailability of a therapeutically effective amount of at least one compound classified as BCS Class II, BCS Class III or BCS Class IV including orally administering a pharmaceutical composition including at least one compound classified as BCS Class II, BCS Class III or BCS Class IV; at least one absorption enhancer; at least one pH lowering compound; and at least one chelating agent.

The present invention also provides methods of treating a bacterial or viral infection in a subject in need thereof including orally administering a pharmaceutical composition including at least one compound classified as BCS Class II, BCS Class III or BCS Class IV; at least one absorption enhancer; at least one pH lowering compound; and at least one chelating agent. The bacterial infection can be a gram-positive or gram-negative infection.

The present invention also provides methods of treating complicated skin and skin structure infections (cSSSI) in a subject in need thereof including orally administering a pharmaceutical composition including at least one compound classified as BCS Class II, BCS Class III or BCS Class IV; at least one absorption enhancer; at least one pH lowering compound; and at least one chelating agent.

The at least one compound classified as BCS Class II, BCS Class III or BCS Class IV can be a small molecule organic compound. The at least one compound classified as BCS Class II, BCS Class III or BCS Class IV can be an antibiotic or antiviral compound. The at least one compound classified as BCS Class II, BCS Class III or BCS Class IV can be a tigecycline, zanamivir, kanamycin, tobramycin or fenofibrate.

The pharmaceutical composition can be a solid dosage pharmaceutical composition, the pharmaceutical composition can be a multilayer solid dosage pharmaceutical composition.

The pH lowering compound can have a pKa no higher than 4.2, the pH lowering compound can have a pKa no higher than 3.0. Preferably, the pH lowering agent is sodium citrate.

The chelating agent can be a carboxylic acid chelating agent or an amino acid chelating agent. The carboxylic acid chelating agent can be acetylsalicylic acid, acetic acid, ascorbic acid, citric acid, fumaric acid, glucuronic acid, glutaric acid, glyceric acid, glycocolic acid, glyoxic acid, isocitric acid, isovaleric acid, lactic acid, maleic acid, oxaloacetic acid, oxalosuccinic acid, propionic acid, pyruvic acid, succinic acid, tartaric acid, or valeric acid. Preferably, the carboxylic acid chelating agent is citric acid.

The at least one absorption enhancer can include an acylcarnitine. Preferably, the acylcarnitine is lauroyl carnitine. The at least one absorption enhancer can include a surface acting agent. The surface acting agent can be an acid soluble bile acid.

The pharmaceutical composition can further include a cationic surface acting agent.

The pharmaceutical composition can further include an acid resistant protective vehicle. Preferably, the acid resistant protective vehicle is a viscous protective syrup.

A multilayered solid dosage pharmaceutical composition including a chelating agent and an acid resistant protective vehicle can also include a water soluble barrier is layered between the chelating agent and the acid resistant protective vehicle.

The present invention provides a pharmaceutical composition suitable for oral delivery including: at least one antibiotic or antiviral compound classified as BCS Class II, BCS Class III or BCS Class IV; lauroyl-carnitine; citric acid; and sodium citrate, wherein the composition is buffered at pH 3.5.

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

While this disclosure has been particularly shown and described with references to preferred aspects thereof, it will be understood by those skilled in the art that various changes in form and details may be made therein without departing from the scope of the disclosure encompassed by the appended claims.

The patent and scientific literature referred to herein establishes the knowledge that is available to those with skill

DETAILED DESCRIPTION OF THE INVENTION

Figure 1:
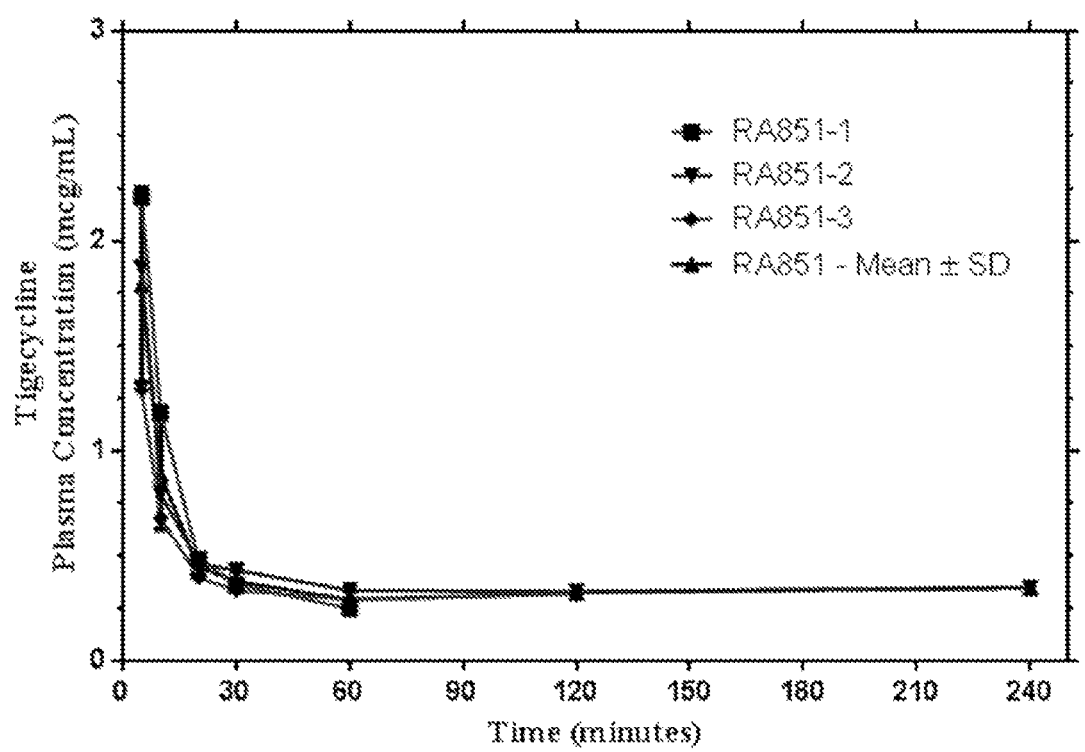
FIG. 1 is a graph showing Individual and Mean (±SD) Plasma Tigecycline Concentration in Sprague-Dawley Rats Following a Single Dose IV Bolus Injection of 0.64 mg/kg.

The present invention provides a pharmaceutical composition suitable for oral delivery including at least one compound classified as BCS Class II, BCS Class III or BCS Class IV; at least one absorption enhancer; at least one pH lowering compound; and at least one chelating agent.

The at least one compound classified as BCS Class II, BCS Class III or BCS Class IV can be a small molecule organic compound. The at least one compound classified as BCS Class II, BCS Class III or BCS Class IV can be an antibiotic or antiviral compound. The at least one compound classified as BCS Class II, BCS Class III or BCS Class IV can be a tigecycline, zanamivir, kanamycin, tobramycin or fenofibrate.

The pharmaceutical composition can be a solid dosage pharmaceutical composition (e.g., tablet, capsule). The pharmaceutical composition can be a multilayer solid dosage pharmaceutical composition.

The pH lowering compound can have a pKa no higher than 4.2, the pH lowering compound can have a pKa no higher than 3.0. Preferably, the pH lowering agent is sodium citrate.

The chelating agent can be a carboxylic acid chelating agent or an amino acid chelating agent. The carboxylic acid chelating agent can be acetylsalicylic acid, acetic acid, ascorbic acid, citric acid, fumaric acid, glucuronic acid, glutaric acid, glyceric acid, glycocolic acid, glyoxic acid, isocitric acid, isovaleric acid, lactic acid, maleic acid, oxaloacetic acid, oxalosuccinic acid, propionic acid, pyruvic acid, succinic acid, tartaric acid, or valeric acid. Preferably, the carboxylic acid chelating agent is citric acid.

The at least one absorption enhancer can include an acylcarnitine. Preferably, the acylcarnitine is lauroyl carnitine. The at least one absorption enhancer can include a surface acting agent. The surface acting agent can be an acid soluble bile acid.

The pharmaceutical composition can further include a cationic surface acting agent.

The pharmaceutical composition can further include an acid resistant protective vehicle. Preferably, the acid resistant protective vehicle is a viscous protective syrup.

A multilayered solid dosage pharmaceutical composition including a chelating agent and an acid resistant protective vehicle can also include a water soluble barrier is layered between the chelating agent and the acid resistant protective vehicle.

The present invention provides a pharmaceutical composition suitable for oral delivery including: at least one antibiotic or antiviral compound classified as BCS Class II, BCS Class III or BCS Class IV; lauroyl-carnitine; citric acid; and sodium citrate, wherein the composition is buffered at pH 3.5.

The present invention provides pharmaceutical compositions comprising a therapeutically effective amount of at least one compound selected from one of a Class II drug, a Class III drug or a Class IV drug; at least one chelating agent; and at least one absorption enhancer. The composition can further comprise at least one pH lowering agent. The composition can further comprise an acid resistant protective vehicle effective to transport the pharmaceutical composition through the stomach of a patient. The composition can further comprise a water soluble barrier layer that separates the chelator from the acid resistant protective vehicle. In an aspect, the chelating agent is a carboxylic acid. In an aspect, the carboxylic acid is citric acid. In an aspect, the citric acid is present in the pharmaceutical composition in a quantity which, if the composition were added to ten milliliters of 0.01M aqueous sodium bicarbonate solution, would be sufficient to lower the pH of the solution to no higher than 5.5. In an aspect, the citric acid is present in the pharmaceutical composition in a quantity which, if the composition were added to ten milliliters of 0.05M aqueous sodium bicarbonate solution, would be sufficient to lower the pH of the solution to no higher than 5.5. In an aspect, the citric acid is present in the pharmaceutical composition in a quantity which, if the composition were added to ten milliliters of 0.1M aqueous sodium bicarbonate solution, would be sufficient to lower the pH of the solution to no higher than 5.5. In an aspect, the absorption enhancer is lauroyl carnitine.

Pharmaceutical Compositions

The present invention provides a pharmaceutical composition suitable for oral delivery including at least one compound classified as BCS Class II, BCS Class III or BCS Class IV.

The Biopharmaceutical Classification System (BCS), originally developed by G. Amidon, separates pharmaceuticals for oral administration into four classes depending on their aqueous solubility and their permeability through the intestinal cell layer. According to the BCS, drug substances are classified as follows: Class I—High Permeability, High Solubility; Class II—High Permeability, Low Solubility; Class III—Low Permeability, High Solubility; and Class IV—Low Permeability, Low Solubility.

As used herein, a compound is considered highly soluble when the highest dose strength is soluble in <250 ml water over a pH range of 1 to 7.5. As used herein, a compound is considered highly permeable when the extent of absorption in humans is determined to be >90% of an administered dose, based on mass-balance or in comparison to an intravenous reference dose. As used herein, a compound is considered to be rapidly dissolving when >85% of the labeled amount of drug substance dissolves within 30 minutes using USP apparatus I or II in a volume of <900 ml buffer solutions.

As used herein, a compound or drug (these terms are interchangeably) does not include a peptide bond in its molecular structure. It should be understood that a compound of the invention can comprise a small molecule. The term small molecule as used herein refers to a low molecular weight organic, inorganic, or organometallic compound. A small molecule may comprise a molecular weight of less than 2000 Daltons. A small molecule may comprise a molecular weight of less than 500 Daltons. A small molecule may comprise a molecular weight of about 50 to 500 Daltons.

A compound of the present invention can be a compound that targets bacterial functions or growth processes, for example an antibiotic. The compound can be an antibiotic that contains a central four-ring carbocyclic skeleton. The antibiotic can be a tetracycline or glycylcycline antibiotic. In preferred aspects, the antibiotic is tigecycline. The compound can be capable of binding to a ribosomal subunit of a bacterium. A compound of the present invention can be a compound that targets a virus or viral particle, for example an antiviral agent or compound.

The compound can be classified as a BCS class II drug, a class III drug, or a BCS class IV drug. Non-limiting examples of BCS class II drugs are: glibenclamide, bicalutamide, ezetimibe, fenofibrate, glipizide, atovaquone, carbamazepine, danazol, griseofulvin, ketoconazole, toglitazone, ibuprofen, nifedipine, nitrofurantoin, phenytoin, sulfamethoxazole, trimethoprim, valproic acid, praziquantel, retinol palmitate, and sulfasalazine. Non-limiting examples of BCS class III drugs are: cimetidine, acyclovir, atenolol, ranitidine, abacavir, captopril, chloramphenicol, codeine, colchicine, dapsone, ergotamine, kanamycin, tobramycin, tigecycline, zanamivir, hydralazine, hydrochlorothiazide, levothyroxine, methyldopa, paracetamol, propylthiouracil, pyrodostigmine, sodium cloxacillin, thiamine, benzidazole, didanosine, ethambutol, ethosuximide, folic acid, nicotinamide, nifurtimox, and salbutamol sulfate. Non-limiting examples of BCS class IV drugs are: hydrochlorothiazide, furosemide, cyclosporin A, itraconazole, indinavir, nelfinavir, ritonavir, saquinavir, nitrofurantoin, albendazole, acetazolamide, azithromycin.

In some preferred aspects of the present invention, the compound is Tigecycline. Tigecycline is the first approved member in a new class of glycylcycline-based tetracycline antibiotics. Tigecycline exhibits activity against a variety of gram-positive and gram-negative bacterial pathogens, many of which are resistant to existing antibiotics—including activity against Methicillin-Resistant *Staphylococcus aureus* (MRSA), *Stenotrophomonas maltophilia*, *Haemophilus influenzae*, and *Neisseria gonorrhoeae* (with MIC values reported at 2 mcg/mL) and multi-drug resistant strains of *Acinetobacter baumannii*, as non-limiting examples. Tigecycline is licensed for the treatment of skin and soft tissue infections as well as intra-abdominal infections and has been previously utilized as a lyophilized powder for reconstitution for IV infusion in the hospital setting primarily due to its inherently low innate permeability. Tigecycline's aqueous solubility is approximately 300 mg/mL, its permeability liability makes oral administration a challenge. Known formulations exhibit maximal oral bioavailablity % (% F) less than 5%. Commensurate with its high aqueous solubility and poor membrane permeation, tigecycline is not extensively metabolized. The drug is primarily cleared through the biliary route, largely as unchanged drug. In one aspect, the pharmaceutical composition of the present invention is an improved oral dosage formula of tigecycline. In one aspect, the pharmaceutical composition of the present invention is an oral dosage formula of tigecycline for oral conversion of treatment after a patient's clinical signs have stabilized, indicating control of infection. In one aspect, the oral dosage formulation of tigecycline of the present invention is used to control recurrent infections in patients with no, or minimal hepatic impairment.

In some preferred aspects of the present invention, the compound is zanamivir. In one aspect, a pharmaceutical composition of the present disclosure is zanamivir formulated with a pH-lowering agent (e.g. buffered citric acid) and/or a permeation enhancer (e.g. lauroyl-L-carnitine) or as an emulsion (e.g. an emulsion in Capmul).

A pharmaceutical composition suitable for oral delivery including at least one compound classified as BCS Class II, BCS Class III or BCS Class IV of the present invention can also comprise at least one chelating agent. The chelating agent can be a carboxylic acid chelating agent or an amino acid chelating agent.

Suitable carboxylic acids that can be used as a chelating agent of the present disclosure, include, but are not limited to, acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Suitable organic amino acids that can be used as a chelating agent of the present disclosure, include, but are not limited to, glutamic acid, aspartic acid, histidine, and the like.

The chelating agent can be a high affinity chelating agent. A high affinity chelating agent can chelate cationic metals, thereby inhibiting salt-induced precipitation. In a preferred aspect, the chelating agent is citric acid. Citric acid exhibits three (3) ionizable groups, distinguished by 3 different pKa, circa pH=3.09, 4.75, and 6.39. This property allows citric acid to act as a polydentate binder, or sequestering agent of cationic species in solution. The net result is that citric acid is an excellent chelating agent, specifically for small metal ions such as calcium. In the active pH range of the current formulation (<pH 5.5) however because of the respective pKa of the ionizable groups, one would expect that the larger percentage of 1, or 2 (depending on pH) of these ionizable groups would be protonated, and therefore, not available to bind cationic salts, such as calcium. As such, at the pH in question (<pH 5.5), citric acid would not be expected to be as efficient a chelating agent in this pH range as in more basic conditions.

Suitable chelating agents can also include EDTA, EGTA, Phosphonates, and bisphosphonates.

A pharmaceutical composition suitable for oral delivery including at least one compound classified as BCS Class II, BCS Class III or BCS Class IV of the present invention can also comprise coated acid particles.

In one aspect, the carboxylic acid can be provided, at least in part, by acid particles coated with a protective coating to reduce undesirable acid interaction with other components of the formulation, such as the compound and, where used, the outer enteric coating. When coated acid particles are used, the particles are coated with a pharmaceutically acceptable protective coating that is non-acidic and preferably has a solubility in water of at least one gram, and preferably at least 10 grams, per 100 milliliters of water at room temperature. As the coating is for the purpose of reducing acid interaction with other components of the pharmaceutical composition, it is important that the coating not itself be acidic such that its own acidity could undesirably cause some of the acid interactions that it is the coating's purpose to prevent. Good water solubility is also important for quick dissolution, which in turn desirably aids a more simultaneous release of the pharmaceutical acid, the drug and the absorption enhancer.

Appropriate coating materials include but are not limited to sugars (e.g. glucose), oligosaccharides (maltodextrin), and acid salts (e.g. sodium citrate). When acid salts are used, it is preferred, but not required, that they be salts of the acid being coated (e.g., sodium citrate-coated citric acid particles). Preferred coated acid particles include but are not limited to maltodextrin-coated citric acid particles available from Jungbunzlauer under the trademark CITROCOAT. When used as the acid, citric acid or other organic acids can be coated by spraying a coating solution which contains, for example, glucose, maltodextrin or sodium citrate onto granules of an organic acid in a fluid-bed dryer. Coatings discussed herein may be used on particles of other acids discussed herein.

The average size of the acid-coated particles can be from about 30 mesh to about 140 mesh.

A pharmaceutical composition suitable for oral delivery including at least one compound classified as BCS Class II, BCS Class III or BCS Class IV of the present invention can also comprise at least one pH-lowering compound.

The quantity of pH-lowering compound can be determined based on the type of pH-lowering compound used and the equivalents of protons provided by a given pH-lowering compound.

The pH-lowering compound can be any pharmaceutically acceptable compound that is not toxic in the gastrointestinal tract and is capable of either delivering hydrogen ions (a Bronsted-Lowry acid) or of inducing higher hydrogen ion content from the local environment (acting as an Arrhenius or Lewis acid). It can also be any combination of such compounds and/or a combination of such compounds and their respective conjugate bases to maintain the target pH. In one aspect, at least one pH-lowering compound used in the composition has a pKa no higher than 4.2, and preferably no higher than 3.0. In one aspect, at least one pH-lowering compound has a solubility in water of at least 30 grams per 100 milliliters of water at room temperature.

Non-limiting examples of compounds that are Arrhenius or Lewis acids include halide salts of metals, such as aluminum chloride and zinc chloride. Pharmaceutically acceptable traditional acids include, but are not limited to acid salts of amino acids (e.g., amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other useful pH-lowering compounds that might not usually be called "acids" in the art, but which may nonetheless be useful in accordance with the invention are organophosphates with at least one free phosphohydroxyl group, such as phosphate esters (e.g., fructose 1, 6 diphosphate, glucose 1, 6 diphosphate, phosphoglyceric acid, and diphosphoglyceric acid). CARBOPOL™. (Trademark BF Goodrich) and polymers such as polycarbophil may also be used to lower pH.

A pharmaceutical composition suitable for oral delivery including at least one compound classified as BCS Class II, BCS Class III or BCS Class IV of the present invention can also comprise at least one absorption enhancer.

The absorption enhancers can be present in a quantity that constitutes from 0.1 to 20.0 percent by weight, relative to the overall weight of the pharmaceutical composition (exclusive of the enteric coating). Suitable absorption enhancers can be surface active agents which act both as solubility enhancers and uptake enhancers. Generically speaking, "solubility enhancers" improve the ability of the components of the present disclosure to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which drugs cross the intestinal wall.

One or more absorption enhancers may perform one function only (e.g., solubility), or one or more absorption enhancers may perform the other function only (e.g., uptake). It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents can be useful both as solubility enhancers and as uptake enhancers. For example, detergents are useful in (1) solubilizing all of the active components quickly into the aqueous environment where they are originally released, (2) enhancing lipophilicity of the components of the present disclosure, especially the drug, aiding its passage into and through the intestinal mucus, (3) enhancing the ability of the drug to cross the epithelial barrier of the brush border membrane; and (4) increasing transcellular or paracellular transport as described herein.

When surface active agents are used as the absorption enhancers, they can be free flowing powders for facilitating the mixing and loading of capsules during the manufacturing process. When trying to increase the bioavailability of a compound, the surface active agent used as an absorption enhancer can be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. The absorption enhancer can be soluble at acid pH, particularly in the 3.0 to 5.0 range.

In one aspect, a combination of a cationic surface active agent together with an anionic surface active agent can be present in a pharmaceutical composition of the present invention. In one aspect, both the cationic surface active agent and the anionic surface active agent can be cholesterol derivatives and both can be soluble at acid pH.

In one aspect, a combination of an acid soluble bile acid together with a cationic surface active agent can be present in a pharmaceutical composition of the present invention. In one aspect, the combination can be acyl carnitine and sucrose ester. When a particular absorption enhancer is used alone, it is preferred that it be a cationic surface active agent. Acyl carnitines (e.g., lauroyl carnitine), phospholipids and bile acids are particularly good absorption enhancers, especially acyl carnitine. Anionic surfactants that are cholesterol derivatives are also used in some aspects. It is the intent of these preferences to avoid interactions with the drug that interfere with absorption of the drug into the blood.

To reduce the likelihood of side effects, preferred detergents, when used as the absorption enhancers of the present disclosure, can be either biodegradable or reabsorbable (e.g. biologically recyclable compounds such as bile acids, phospholipids, and/or acyl carnitines), preferably biodegradable. Acylcarnitines are believed particularly useful in enhancing paracellular transport.

Non-limiting examples of absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.), d-alpha tocopheryl polyethylene glycol 1000 succinate (vitamin E TPGS); (d) anionic surfactants such as dioctyl sodium sulfosuccinate; (e) lyso-phospholipids such as lyso-lecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, pahnitoylcholine, hexadecyllysine, N-acylphenylalanine, N-acylglycine etc.; (g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric, lauric acids and the like); (i) ethylenediaminetetraacetic acid; (j) cationic surfactants such as cetylpyridinium chloride, benzalkonium chloride, benzethonium chloride and the like; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc. In one aspect, the absorption enhancer is lauroyl carnitine.

A pharmaceutical composition suitable for oral delivery including at least one compound classified as BCS Class II, BCS Class III or BCS Class IV of the present invention can also comprise an acid-resistant protective vehicle.

Many acid-resistant protective vehicles (enteric coatings) are known in the art, and are useful in accordance with the present disclosure. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In one aspect, the compound, absorption enhancers such as solubility and/or uptake enhancer(s), and carboxylic acids, are included in a sufficiently viscous protective syrup to permit protected passage of the components of the present disclosure through the stomach.

Suitable enteric coatings may be applied, for example, to capsules after the remaining components of the present disclosure have been loaded within the capsule. In other aspects, enteric coating is coated on the outside of a tablet or coated on the outer surface of particles of active components which are then pressed into tablet form, or loaded into a capsule, which is itself preferably coated with an enteric coating.

All components of the present disclosure should be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present disclosure is believed effective in the colon as well as in the small intestine. Numerous vehicles or carriers, in addition to the ones discussed above, are known in the art. It is desirable (especially in optimizing how simultaneously the components of the present disclosure are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the present disclosure in 0.1N HC1 for at least two hours, then capable of permitting complete release of all contents of the pharmaceutical composition within thirty minutes after pH is increased to 6.3 in a dissolution bath in which said composition is rotating at 100 revolutions per minute. In aspects in which the water-soluble barrier layer of the present disclosure is used, less enteric coating may be required, sometimes less that the amount of water-soluble barrier layer.

A pharmaceutical composition suitable for oral delivery including at least one compound classified as BCS Class II, BCS Class III or BCS Class IV of the present invention can be a solid dosage form. The pharmaceutical composition can also be a multi-layered solid dosage form.

In an aspect where the pharmaceutical composition can also be a multi-layered solid dosage form, and the pharmaceutical composition includes citric acid and an acid resistant protective vehicle, a water-soluble barrier can be present to separate the chelating agent from the acid resistant protective vehicle. In some of the examples which follow, a conventional pharmaceutical capsule is used for the purpose of providing this barrier. Many water soluble barriers are known in the art and include, but are not limited to, hydroxypropyl methylcellulose and conventional pharmaceutical gelatins.

In an aspect, a peptide (such as albumin, casein, soy protein, other animal or vegetable proteins and the like) can be included to reduce non-specific adsorption (e.g., binding of peptide to the intestinal mucus barrier). When added, the peptide is preferably from 1.0 to 10.0 percent by weight relative to the weight of the overall pharmaceutical composition (excluding protective vehicle). Preferably, the peptide is not physiologically active and is most preferably a food peptide such as soy bean peptide or the like.

All pharmaceutical compositions of the present disclosure can also comprise common pharmaceutical diluents, glidants, fillers, lubricants, antioxidants, gelatin capsules, preservatives, colorants and the like in their usual known sizes and amounts.

A suitable filler includes a cellulose filler like PROSOLV™ available from JRS Pharma be utilized. Other fillers are known in the art can also be utilized.

Any disintegrant that performs the function of enhancing dissolution speed may be used. Non-limiting examples of suitable disintegrants include POLYPLASDONE, EXPLOTAB, and AC-DI-SOL, available from International Specialty Products, JRS Pharma and FMC Biopolymer, respectively. Preferably, the disintegrant is present in an amount between 1 and 15 percent by weight relative to the total tablet weight (when tablets are used), exclusive of any water-soluble barrier layer and any acid-resistant protective vehicle.

Any glidant that performs the function of enhancing powder flow may be used. Non-limiting examples of suitable glidants include talc, calcium silicate, magnesium silicate, silicon dioxide. Preferably, the glidant is present in an amount between 0.1 and 2.0 percent by weight relative to the weight of the pharmaceutical composition, exclusive of any water-soluble barrier layer and any acid-resistant protective vehicle.

Any lubricant that performs the function of preventing powder from sticking to the tooling may be used. Non-limiting examples of suitable lubricants include stearic acid, magnesium stearate, and hydrogenated vegetable oil type 1. Preferably, the lubricant is present in an amount between 0.5 and 5.0 percent by weight relative to the weight of the pharmaceutical composition, exclusive of any water-soluble barrier layer and any acid-resistant protective vehicle.

Non-limiting examples of suitable antioxidants include sodium pyruvate, derivatives of sodium pyruvate, ascorbic acid, ascorbyl palmitate, butylated hydroxyanisole, butylated hydroxytoluene, sodium bisulfate, and sodium metabisulfite. Preferably, the antioxidant is present in an amount between 0.5 and 5 mg per tablet.

The pharmaceutical composition can also comprise a peptide (such as albumin, casein, soy protein, other animal or vegetable proteins and the like) to reduce non-specific adsorption (e.g., binding of peptide to the intestinal mucus barrier) thereby lowering the necessary concentration of the drug. When added, the peptide is preferably from 1.0 to 10.0 percent by weight relative to the weight of the overall pharmaceutical composition (excluding any water-soluble barrier layer and any acid-resistant protective vehicle). Preferably, the peptide is not physiologically active and is most preferably a food peptide such as soybean peptide or the like.

The pharmaceutical composition can be a solid dosage form. Once suitable solid dosage form is a tablet. When the pharmaceutical composition is a table a pharmaceutical binder for dry compression can also be included. Non-limiting examples of suitable binders include KOLLIDON VA64, KOLLIDON VA64 fine, KOLLIDON 30, AVICEL PH-101, PHARMACOAT 606, and MALDEX. The first three are commercially available from BASF, and the latter three are available from FMC Biopolymer, Shin-Etsu, and Amylum, respectively.

To improve simultaneous release, thorough intermixing of the components of the pharmaceutical composition (other than any optional enteric coating or barrier layer) results in substantially uniform dispersion of said components within the binder. For this purpose, coated acid particles (when used) are considered a single component. It is especially preferred that acid (or when used, coated acid particles) and drug be uniformly dispersed.

When prepared in tablet form, it is preferred that the maximum weight loss during friability testing be no greater than 1%. As used herein, friability testing refers to the technique described in "Tablet Friability", Chapter 1216, USP 28 page 2745.

In one aspect, the weight ratio of citric acid to absorption enhancer can be between 3:1 and 20:1, preferably 4:1-12:1, and most preferably 5:1-10:1. The total weight of citric acid and the total weight of absorption enhancer in a given pharmaceutical composition are included in the foregoing preferred ratios.

In one aspect, a compound, a pH lowering compound, and a absorption enhancer (whether single compounds or a plurality of compounds in each category) are uniformly dispersed in the pharmaceutical composition. The pharmaceutical composition can comprise granules that include a pharmaceutical binder having the drug, the citric acid and the absorption enhancer uniformly dispersed within said binder. Preferred granules may also consist of an acid core, surrounded by a uniform layer of organic acid, a layer of enhancer and a layer of drug that is surrounded by an outer layer of organic acid. Granules may be prepared from an aqueous mixture consisting of pharmaceutical binders such as polyvinyl pyrrolidone or hydroxypropyl methylcellulose, together with the citric acid, absorption enhancer and drug of the present disclosure, or by dry granulation processes. Other aspects include matrix or other tablet or capsule-based systems that may include multiple granulation phases, such as granulation of the drug, with or without solubility enhancing excipients and other processing excipients, in concert with an external granulated citric acid phase.

Solubility enhancement for compounds with low or no water solubility can also be achieved using additional processing techniques known in the art. Such techniques include, but are not limited, to spray drying, lyophilization, or hot melt extrusion to form an amorphic dispersion using a suitable, pharmaceutically acceptable polymer, such as PVP, HPMC, HPMCP, HPMCAS, PEG, PVP/VA, MME, CAP, polaxamer, gelucire, Tween, Eudragit, CMEC, gelatin, etc. Many other such additional excipients will be apparent to one of skill in the art. The permeation enhancer can be used as the surfactant to aid dispersion formation during processing, while maintaining its permeation enhancing affects in vivo. Such aspects could then be filled as a dry blend into capsules with the remaining active and processing excipients, or compressed into tablets, with or without granulation.

In an aspect, a pharmaceutical composition of the present invention comprises a size 00 gelatin or HPMC capsule filled with 50 mg of compound, 500 mg of granular citric acid (available for example from Archer Daniels Midland Corp.), and 50 mg lauroyl carnitine (SIGMA).

All of the ingredients are preferably for eventual insertion into the gelatin or HPMC capsule and are preferably powders which may be added to a blender in any order. Thereafter, the blender is run for about five minutes until the powders are thoroughly intermixed. Then the mixed powders are loaded into the large end of the capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)).

An enteric coating solution is made as follows. Weigh 500 grams of EUDRAGIT L30 D-55 (poly(methacrylic acid-co-ethyl acrylate) 1:1; a methacrylic acid-ethyl acrylate copolymer (1:1), an enteric coating available from Evonik). Add 411 grams distilled water, 15 grams triethyl citrate and 38 grams talc. This amount of coating will be sufficient to coat about 500 size 00 capsules.

The capsules are the film coated using processes known in the art.

Because of the enhanced bioavailability provided by the present disclosure, the concentration of expensive drug in the pharmaceutical preparation of the present disclosure may be kept relatively low.

In an aspect, a pharmaceutical composition of the present disclosure is a tablet prepared as follows:
1. High shear or COMIL™ geometrical mixing of drug and microcrystalline cellulose (PROSOLV™—such as PROSOLV™ HD90).
2. Add mixed components of step 1 to V blender along with citric acid DC F20, lauroyl-L-carnitine, Crospovidone, KOLLIDON VA64 and sodium pyruvate. Mix in V blender.
3. Add magnesium stearate to V blender after step 2 completed. Mix in V blender briefly.
4. Compress blend into tablets.
5. Coat tablets with optional water-soluble barrier, such as hydroxypropylmethylcellulose (HPMC) or PVA subcoat, to 6% weight gain.
6. Coat tablets with optional enteric coat (EUDRAGIT L30D-55) to 7% weight gain.

Methods of Treatment

The present invention also provides methods for enhancing the bioavailability of a therapeutically effective amount of at least one compound classified as BCS Class II, BCS Class III or BCS Class IV including orally administering a pharmaceutical composition including at least one compound classified as BCS Class II, BCS Class III or BCS Class IV; at least one absorption enhancer; at least one pH lowering compound; and at least one chelating agent.

The present invention also provides methods of treating a bacterial or viral infection in a subject in need thereof including orally administering a pharmaceutical composition including at least one compound classified as BCS Class II, BCS Class III or BCS Class IV; at least one absorption enhancer; at least one pH lowering compound; and at least one chelating agent. The bacterial infection can be a gram-positive or gram-negative infection.

The present invention also provides methods of treating complicated skin and skin structure infections (cSSSI) in a subject in need thereof including orally administering a pharmaceutical composition including at least one compound classified as BCS Class II, BCS Class III or BCS Class IV; at least one absorption enhancer; at least one pH lowering compound; and at least one chelating agent.

The terms "subject" and "patient," as used herein, describes an organism, including mammals, to which treatment with the compositions and methods of the present invention are provided. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human. The terms "subject" and "patient" are used interchangeable herein.

The term "therapeutically effective amount," as used herein, refers to an amount of a pharmaceutical composition to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration.

According to aspects illustrated herein, there is disclosed a method for enhancing the bioavailability of a Class II, III or IV drug delivered orally that includes selectively releasing a therapeutically effective amount of the drug, together with at least one chelating agent and at least one absorption enhancer, into a patient's intestine following passage of the drug, chelating agent and absorption enhancer through the patient's mouth and stomach.

According to aspects illustrated herein, there is disclosed an oral pharmaceutical composition that includes a therapeutically effective amount of tigecycline; a sufficient amount of citric acid to yield chelating properties; and lauroyl carnitine. In an aspect, the composition further comprises at least one pH lowering agent. In an aspect, the composition further comprises an acid resistant protective vehicle effective to transport the pharmaceutical composition through the stomach of a patient. In an aspect, the composition further comprises a water soluble barrier layer that separates the citric acid from the acid resistant protective vehicle. In an aspect, the citric acid is present in the pharmaceutical composition in a quantity which, if the composition were added to ten milliliters of 0.01M aqueous sodium bicarbonate solution, would be sufficient to lower the pH of the solution to no higher than 5.5. In an aspect, the citric acid is present in the pharmaceutical composition in a quantity which, if the composition were added to ten milliliters of 0.05M aqueous sodium bicarbonate solution, would be sufficient to lower the pH of the solution to no higher than 5.5. In an aspect, the citric acid is present in the pharmaceutical composition in a quantity which, if the composition were added to ten milliliters of 0.1M aqueous sodium bicarbonate solution, would be sufficient to lower the pH of the solution to no higher than 5.5.

According to aspects illustrated herein, there is disclosed a method for enhancing the bioavailability of tigecycline delivered orally that includes selectively releasing a therapeutically effective amount of tigecycline, together with a sufficient amount of citric acid and lauroyl carnitine, into a patient's intestine following passage of the tigecycline, citric acid, and lauroyl carnitine through the patient's mouth and stomach.

The simultaneous use of absorption enhancers together with a chelating agent, in accordance with the present disclosure, provides a surprisingly synergistic effect on bioavailability relative to absorption enhancer alone, or chelating agent alone. Without intending to be bound by theory, an oral pharmaceutical composition of the present disclosure is believed to overcome a series of different and unrelated natural barriers to bioavailability. Various components of the pharmaceutical compositions act to overcome different barriers by mechanisms appropriate to each, and result in synergistic effects on the bioavailability of a Class II, III or IV drug. Some Class II, III or IV drugs, taken alone or in the presence of salts of cationic metals, have reduced bioavailability due to chelate formation in the gut. Without intending to be bound by theory, it is believed that when a sufficient amount of citric acid is used as a chelating agent in a composition of the present disclosure, the citric acid can act as a high affinity chelating agent. As used herein, the term "high affinity chelating agent" means a chelating agent that exhibits a low equilibrium dissociation constant, $K_d$ towards the respective metal salt in question. For example, the citric acid is believed to chelate the cationic metal salts, which are therefore not available to interfere with the body's ability to absorb the Class II, III or IV drug. Without intending to be bound by theory, it appears that, in accordance with the present disclosure, a Class II, III or IV drug administered in a pharmaceutical composition of the present disclosure is transported through the stomach along with the chelator (i.e., the dosage form is passed intact past the pylorus).

According to aspects illustrated herein, there is disclosed a method for treating a patient having a gram-positive or a gram-negative bacterial pathogen comprising oral administering to the patient a solid dosage form, wherein the solid dosage form comprises a therapeutically effective amount of tigecycline, at least one chelating agent and at least one absorption enhancer. In an aspect, there is disclosed a method for treating a patient having complicated skin and skin structure infections (cSSSI) comprising oral administering to the patient a solid dosage form, wherein the solid dosage form comprises a therapeutically effective amount of tigecycline, at least one chelating agent and at least one absorption enhancer. In an aspect, there is disclosed a method for treating a patient having complicated intra-abdominal infections (cIAI) comprising oral administering to the patient a solid dosage form, wherein the solid dosage form comprises a therapeutically effective amount of tigecycline, at least one chelating agent and at least one absorption enhancer. In an aspect, at least one of the chelating agents is citric acid in a sufficient amount.

In accordance with the present disclosure, patients in need of treatment with Class II, III or IV drugs are provided with a pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a drug. For example, antibiotics in accordance with the present disclosure may be used to treat patients with bacterial infection, protozoan infection and immunomodulation. In addition, antibiotics in accordance with the present disclosure may be used to prevent infection in a surgical wound, as a dental antibiotic prophylaxis and for conditions of neutropenia. For example, vitamins in accordance with the present disclosure may be used to treat patients with a vitamin deficiency. Well-known human vitamin deficiencies involve thiamine (beriberi), niacin (pellagra), vitamin C (scurvy), and vitamin D (rickets).

By definition, Class II, III or IV drugs, taken alone, have reduced bioavailability due to precipitation in gastrointestinal media, their physicochemical properties preclude membrane permeation (either an inherent function of the molecule due to physicochemical properties, or through transport mechanisms, membrane deposition, protein-drug interactions, metabolism, etc.), or a combination thereof. With respect to a number of BCS class II, III or IV drugs, precipitation or insolubility can be an inherent property of the molecule in question, or can occur through ionic interactions, such as in the presence of inorganic, or organic salts, hydrophobic interactions, etc. In an aspect, a carboxylic acid acts as a high affinity chelating agent of the present disclosure. Without intending to be bound by theory, it appears that, in accordance with the present disclosure, a Class II, III or IV drug administered by a pharmaceutical composition of the present disclosure is transported through the gastrointestinal epithelium. The acid is believed to chelate cationic metals, thereby inhibiting salt-induced precipitation, while also acting as an enhancer of paracellular absorption.

In an aspect, the acid is multifunctional and acts as a calcium chelator, a pH lowering agent, a bioavailability enhancer, a permeation enhancer and a membrane wetting/charge dispersal agent. By chelating calcium, the acid may act as a permeation enhancer by opening tight junctions. Moreover, a chelator that is a pH lowering agent can further enhance paracellular permeation by inducing intracellular acidosis, resulting in actomyosin contraction through a PKC mediated event. By sequestering free metals, it is no longer available to inhibit drug solubility, or induce precipitation through complex formation, or salt-induced precipitate formation, or maintain the tight junctional integrity through cadherin interactions. For example, different types of antibiotics have been shown to interact with calcium. Further, citric acid can also act as a pH lowering agent, thereby enhancing paracellular absorption through induction of intracellular acidosis, resulting in actomyosin contraction and increased paracellular flux.

Further, without being bound by theory, through its ability to modify membrane charge dispersal, carboxylic acids can modify the action of membrane bound transporter proteins, thereby increasing absorptive flux.

The mechanism by which the present disclosure is believed to accomplish the goal of enhanced bioavailability of the Class II, III or IV drug is aided by having active components of the pharmaceutical composition released together as simultaneously as possible. The absorption enhancer, which may be a solubility enhancer and/or transport enhancer (as described in more detail below), aids transport of the drug from the gastrointestinal tract to the blood. Many surface active agents may act as both solubility enhancers and transport (uptake) enhancers. Again without intending to be bound by theory, it is believed that enhancing solubility provides (1) a more simultaneous release of the active components of the present disclosure into the aqueous portion of the intestine, (2) better solubility of the drug in, and transport through, a mucous layer along the intestinal walls. Once the drug reaches the intestinal walls, an uptake enhancer provides better transport through the brush border membrane of the intestine into the blood, via either transcellular or paracellular transport. As discussed in more detail below, many preferred compounds may provide both functions. In those instances, preferred aspects utilizing both of these functions may do so by adding only one additional compound to the pharmaceutical composition. In other aspects, separate absorption enhancers may provide the two functions separately.

In an aspect, a single solid dosage form is used at each administration. Near simultaneous release is best achieved by administering all components of the present invention as a single tablet, pill or capsule. However, the present invention also includes, for example, dividing the required amount of acid and enhancers among two or more capsules which may be administered together such that they together provide the necessary amount of all ingredients.

EXAMPLE 1

Administration of Tigecyline in rats

Materials
Animals and Test Article

Naïve, female Sprague-Dawley Rats (Taconic Farms, Germantown, NY) housed in groups of three were maintained in a climate-controlled room on a 12:12 h light-dark cycle with food and water available ad libitum. Animals weighed approximately 250 g at the time of testing. Rats were fasted overnight (with water available), prior to dosing. Information on the test article, tigecycline, is listed in Table 1. Tigecycline stock was prepared fresh on the day of each study in water and diluted in the indicated formulations.

TABLE 1

Test Article Information

| Item | Compound Name | Catalog Number | Batch/Lot Number | Supplier |
|---|---|---|---|---|
| Test Article | Tigecycline | S-1403 | S140301 | Selleck Chemical Co. |

Methods
Doses and Route of Administration

Intravenous (IV) doses were administered as a bolus injection into the left carotid artery at a dose volume of 1.6 mL/kg. Intraduodenal doses were administered as bolus injections into the duodenum at a dose volume of 1.2 mL/kg. Details of dosing and formulation composition for the primary feasibility assessments are summarized in Table 2.

TABLE 2

Target Dosing and Formulations for Primary Feasibility Studies

| Formulation | Route | Dose mg/kg | Dose Volume Tigecycline mL/kg | Dose Concentration Tigecycline mg/mL | Formulation Composition LLC[2] mM | CA[3]-Sodium Citrate[4] pH 3.5 mM |
|---|---|---|---|---|---|---|
| Study RA851 | | | | | | |
| PBS[1] | IV | 0.6 | 1.6 | 0.4 | — | — |
| A[1] | ID | 4.8 | 1.2 | 4.0 | — | — |
| B | ID | 4.8 | 1.2 | 4.0 | 26 | 100 |
| C | ID | 4.8 | 1.2 | 4.0 | 26 | 400 |
| Study RA853 | | | | | | |
| PBS[1] | IV | 12 | 1.6 | 7.5 | — | — |
| A[1] | ID | 9.0 | 1.2 | 7.5 | — | — |
| B | ID | 9.0 | 1.2 | 7.5 | 26 | 100 |
| C | ID | 9.0 | 1.2 | 7.5 | 26 | 400 |

[1]Dulbecco's Phosphate Buffered Saline, Invitrogen (137 mM NaCl, 2.7 mM KCl, 10 mM Na2HPO4, 2 mM KH2PO4)
[2]Lauroyl-L-Carnitine, custom synthesis, Lonza
[3]Coated CA (DC F20), Jungbunzlauer
[4]Sodium citrate, dihydrate, J T Baker, Reagent Additional studies were conducted comparing the % F and PK profiles of tigecycline formulated in one of each active excipient (RA861 and RA869), comparative to the highest % F formulation from the primary feasibility studies (400 mM CA and 26 mM LLC, pH 3.5, from studies RA851 and RA853). An additional study was conducted exploring the effect of formulation pH at constant CA and LLC concentrations (RA867).

TABLE 3

Target Dosing and Formulations for Secondary Mechanistic Studies

| Formulation | Route | Dose mg/kg | Dose Volume Tigecycline mL/kg | Dose Concentration Tigecycline mg/mL | Formulation Composition LLC[2] mM | CA[3]-Sodium Citrate[4] mM[5] |
|---|---|---|---|---|---|---|
| Study RA861 | | | | | | |
| A | ID | 4.8 | 1.2 | 4.0 | 26 | 400 |
| B | ID | 4.8 | 1.2 | 4.0 | — | 400 |
| C | ID | 4.8 | 1.2 | 4.0 | 26 | — |
| Study RA867 | | | | | | |
| A | ID | 4.8 | 1.2 | 4.0 | 26 | 400 |
| B | ID | 4.8 | 1.2 | 4.0 | 26 | 400 (pH 6.0) |
| Study RA869 | | | | | | |
| A[1] | IV | 0.6 | 1.6 | 0.4 | — | — |
| B | ID | 4.8 | 1.2 | 4.0 | 26 | 400 |
| C | ID | 4.8 | 1.2 | 4.0 | 26 | — |

[1]Dulbecco's Phosphate Buffered Saline, Invitrogen (137 mM NaCl, 2.7 mM KCl, 10 mM Na2HPO4, 2 mM KH2PO4)
[2]Lauroyl-L-Carnitine, custom synthesis, Lonza
[3]Coated CA (DC F20), Jungbunzlauer
[4]Sodium citrate, dihydrate, J T Baker, Reagent
[5]Citrate buffer formulated at pH 3.5 unless otherwise noted Anesthesia and Catheterization Female rats were maintained in groups of 3 per polycarbonate (or equivalent) shoebox cage with fresh wood chip bedding at 20-22° C. under a 12 hour on/off light:dark cycle. The rats were fasted overnight prior to surgery and anesthetized by intramuscular injection of 0.3 mL fresh ketamine (67 mg/mL)/xylazine (42 mg/mL) in 0.9% saline into the hind flank. After the rats went limp they were injected intraperitoneally (IP) with 0.1 mL ketamine/xylazine. The anesthetic state was maintained by IP injection of ketamine/xylazine on an as needed basis. Animal weights were determined post-anesthesia induction.

An indwelling catheter for blood sampling was inserted into the right carotid artery by exposing the trachea with Mayo scissors, clamping the bottom of the artery and tying off the top with surgical suture. The area between was nicked with small sharp scissors and Intramedic polyethylene tubing was inserted into the nicked area. The artery with the tubing was sealed with suture to prevent leakage. A 23-gauge Intramedic Luer Stub Adapter was inserted into the cannula and attached to a 3 way valve which was connected to a 3 cc syringe filled with 0.9% normal saline and a 1 cc syringe filled with 5 U/mL sodium heparin for blood sampling.

IV Studies

In the IV phases, tigecycline was administered to groups of 3 naive anesthetized female rats as a bolus injection away from the brain via the left carotid artery that was constricted in the direction of the brain. Blood samples (~0.5 mL) for plasma tigecycline concentration analysis were collected from a surgically implanted cannula in the right carotid artery prior to dosing and at pre-determined time points post-dose up to either 120 or 240 minutes depending on the study. Blood samples were collected in tubes containing 20 µL 180 mM EDTA. The tubes were maintained on ice and then centrifuged at approximately 3000 rpm at 4° C. for 5 minutes. Plasma was harvested immediately after centrifugation of the samples and stored at −20° C. pending analysis.

Intraduodenal Studies

An intraduodenal injection was utilized to mimic oral delivery of an enterically coated capsule or tablet formulation. In the ID phase of the study, naive female rats were administered tigecycline into the duodenum through a 1 mL syringe attached to a 27-gauge needle. Mayo scissors were used to expose the duodenum and the site of administration was identified by measuring 5 cm from the junction of the stomach and the duodenum towards the jejunum. The measured site was identified by inserting a small piece of surgical suture underneath the site for injection. After the formulation was injected, the abdominal cavity was closed with surgical clips. Blood samples (~0.5 mL) were collected from a surgically implanted cannula in the right carotid artery for plasma tigecycline concentration analysis prior to dosing and at pre-determined time points post-dose up to either 120 or 240 minutes depending on the study.

Blood samples were collected in tubes containing 20 µL 180 mM EDTA. The tubes were maintained on ice and then centrifuged at approximately 3000 rpm at 4° C. for 5 minutes. Plasma was harvested immediately after centrifugation of the samples and stored at −20° C. pending analysis.

Analytical Procedure for Tigecycline

The quantitative determination of tigecycline in rat plasma was performed using an HPLC assay with UV detection at 350 nm. Minocycline (VWR international) was used as an internal standard. Sample processing/clean-up of plasma samples was carried out offline by protein precipitation with acidified acetonitrile.

The HPLC system consisted of Shimadzu SIL-HTc HPLC system equipped with dual Shimadzu LC-10ADvp isopumps, a Shimadzu CTO-10ASvp column temperature controller and a Shimadzu SPD-10Avp variable wavelength detector. The chromatographic separation was based on Li et al. with some notable differences (See Li et al., 2004, Quantitation of tigecycline, a novel glycylcycline, by liquid chromatography. *J. Chromatography B.* 811:225-229). HPLC separation was achieved on a reversed phase column (Phenomenex Luna C18(2), 5 µm, 150×4.6 mm, part number: 00F-4252-E0), using an initial isocratic phase, followed by gradient elution of tigecycline. Mobile phase A consisted of 23 mM phosphate buffer pH 2.5 with 6 mM 1-octanesulfonic acid, while mobile phase B consisting of pure acetonitrile. The time program started isocratic at 25% mobile phase B for 6 minutes, followed by a linear increase in mobile phase B to 35% over the next 10 minutes (16 minutes). The system was equilibrated to 25% mobile phase B for an additional 2 minutes, resulting in a total runtime of 18 minutes per sample. The mobile phase flow rate was 1.2 mL/min. Detection was performed using the SPD-10Avp variable wavelength detector set at 350 nm, with a sensitivity of 0.001 aufs.

Both unknown samples and calibration standards (tigecycline in pooled rat plasma) were treated by protein precipitation with acetonitrile spiked with internal standard. The samples were then centrifuged under refrigeration at 13k rpm for 30 minutes. The supernatant was taken and the liquid was removed to dryness in a turbovap. The samples were then reconstituted in 55 µL 0.1M phosphate buffer, pH 3.8. Samples were maintained at 10° C. while on the autoinjector during sequence. The injection volume was 50 µL. The unknown concentration in rat plasma samples was determined by interpolation of the peak area ratios of analyte : internal standard versus the ratio of their nominal concentrations into the regression line obtained from calibration standards spiked in pooled rat plasma. No regression weighting was used for the calculations. The method was demonstrated to be linear to 0.05 µg/mL (defined LOQ). The calibration curve covered the range of 0.05 µg/mL to 5.0 µg/mL.

Due to analytical issues observed in the analyses of earlier study samples, the analytical method was changed slightly for later samples. Mobile phase A was changed to 23 mM phosphate buffer pH 2.5 with 4 mM 1-octanesulfonic acid, while mobile phase B was changed to 90% acetonitrile, 10% water, with 2 mM 1-octanesulfonic acid. The time program started isocratic at 25% mobile phase B for 6 minutes, followed by a linear increase in mobile phase B to 35% over the next 8 minutes (14 minutes), followed by re-equilibration to 25% mobile phase B for an additional 4 minutes, resulting in a total runtime of 18 minutes. The total runtime, detection wavelength, flow rate, injection volume, column and column temperature all remained unchanged. Further, to assist in sample cleanup, the protein precipitation reagent was acidified with 0.5% v/v TFA. The resulting precipitate was centrifuged at 13k rpm for 5 minutes and the dried extract was reconstituted in 60 µL of mobile phase A. The reconstituted pellet was further centrifuged at 5k rpm to pellet any insoluble matter and the supernatant was injected. These changes, presented side-by-side in Table 4 below, resulted in a more robust analytical method, which exhibited better resolution between tigecycline and minocycline, a better signal to noise ratio and eliminated the precipitation problems observed with earlier runs. It should be noted however, that when the method was transferred to an older HPLC system (equipped with a Shimadzu SCT-10Avp system controller and SIL-10A autoinjector), the time program was further altered such that the gradient went to 38% mobile phase B to account to system design changes. All other parameters remained unchanged.

TABLE 4

RP-HPLC Analytical Methods Comparison for Tigecycline

| Parameter | Initial Method | Revised Method |
|---|---|---|
| Column | Phenomenex LUNA ™ C18(2) 5 μm, 150 × 4.6 mm Part number: 00F-4252-E0 | Phenomenex LUNA ™ C18(2) 5 μm, 150 × 4.6 mm Part number: 00F-4252-E0 |
| Column Temperature | 40° C. | 40° C. |
| Flow Rate | 1.2 mL/min | 1.2 mL/min |
| Detection Wavelength | 350 nm | 350 nm |
| Injection Volume | 50 μL | 50 μL |
| Mobile Phase A | 23 mM phosphate buffer pH 2.5 6 mM 1-octanesulfonic acid | 23 mM phosphate buffer pH 2.5 4 mM 1-octanesulfonic acid |
| Mobile Phase B | 100% Acetonitrile | 90% Acetonitrile (v/v) 10% Water (v/v) 2 mM 1-octanesulfonic acid |
| Time Program | 0-6 min: 25% B 6-16 min: linear to 35% B 16-18 min: 25% B | 0-6 min: 25% B 6-14 min: linear to 35% B 14-18 min: 25% B |
| Total Runtime | 18 minutes | 18 minutes |
| Standard Curve | 0.05-5.0 μg/mL | 0.05-5.0 μg/mL |
| Sample Preparation | PPT: Acetonitrile Spin: 13k rpm 30 min Evaporate to dryness Reconstitute in 55 μL 0.1M phosphate buffer, pH 3.8 Inject Reconstitution Solution | PPT: 0.5% TFA (v/v) in Acetonitrile Spin: 13k rpm 5 min Evaporate to dryness Reconstitute in 60 μL MP A Spin: 5k rpm 5 min Inject Supernatant |
| Internal Standard Prep (Minocycline) | 0.4 μg/mL in ppt solution | 0.4 μg/mL in ppt solution |

Pharmacokinetic Data Handling

Tigecycline PK parameters for individual rats were calculated using non-compartmental analysis with PK Functions for Microsoft Excel.

Results: Primary Feasibility Studies (RA851, RA853)

Plasma Tigecycline Following IV Administration

The mean $C_{max}$ for plasma tigecycline at a target dose of 0.64 mg/kg was 1.79 μg/mL and was observed at a mean time ($T_{max}$) of 5 minutes (0.08 hrs; Table 5. Tigecycline was measurable through 4 hours as expected based on a reported single dose half-life of approximately 20 hours. The mean $AUC_{(0-t)}$ was 58.20 μg*min/mL.

Figure 2:
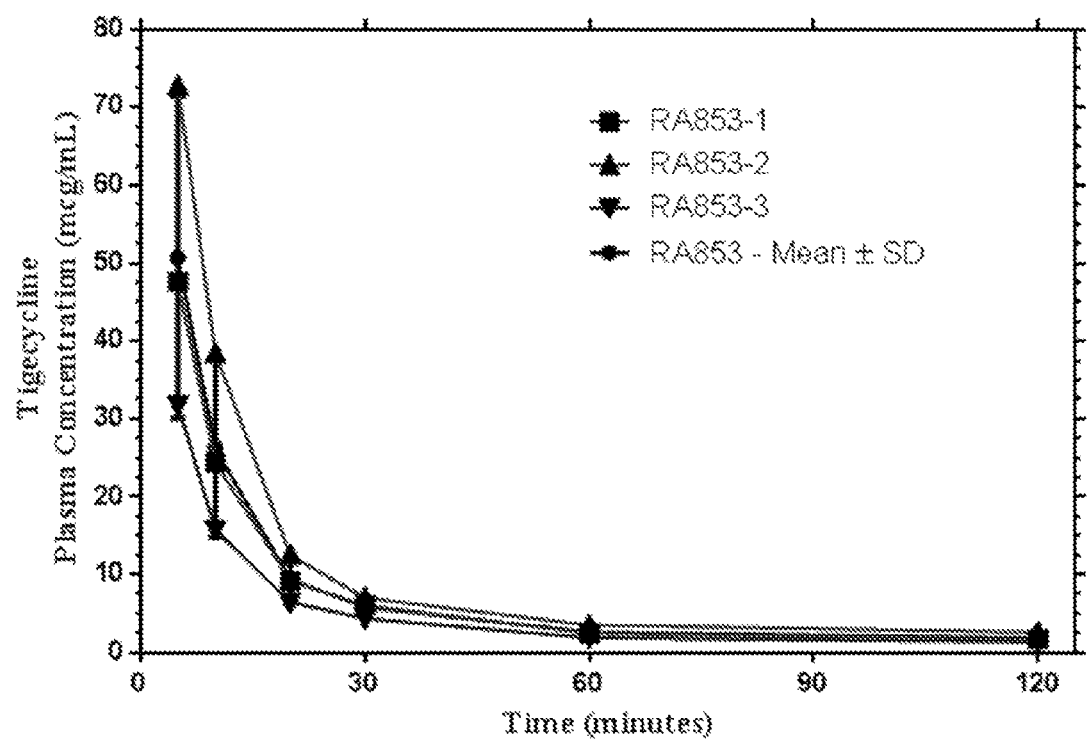
FIG. 2 is a graph showing Individual and Mean (±SD) Plasma Tigecycline Concentration in Sprague-Dawley Rats Following a Single Dose IV Bolus Injection of 12 mg/kg.
Figure 3:
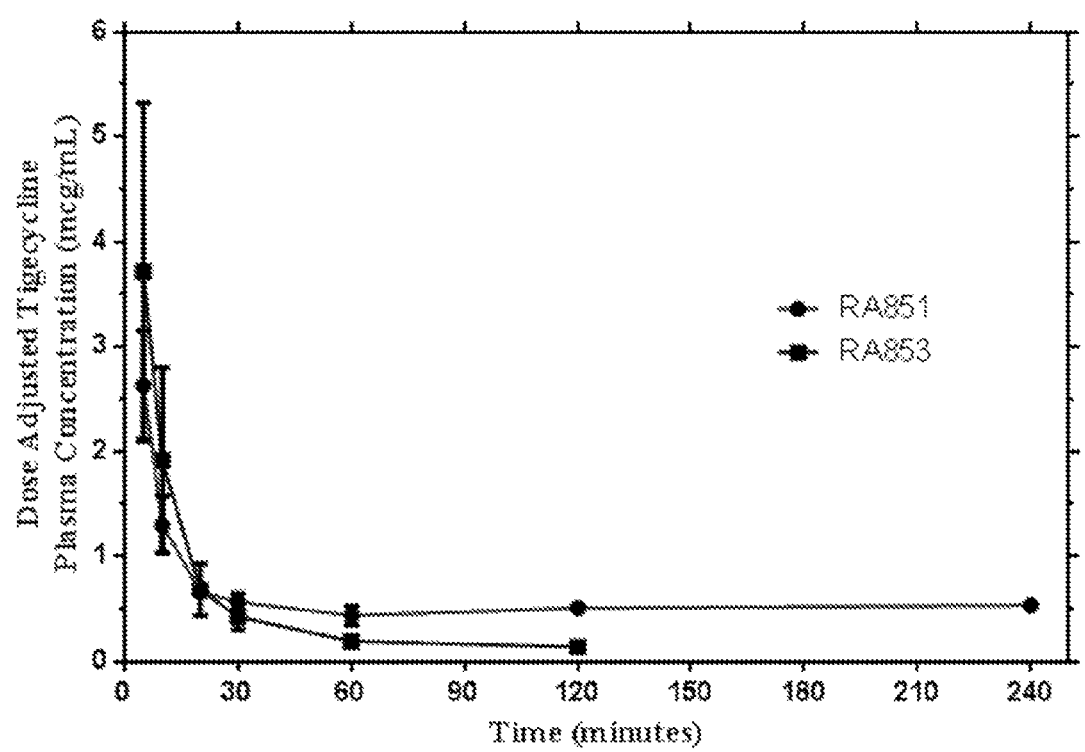
FIG. 3 is a graph showing Dose Adjusted Mean Plasma Tigecycline Concentration in Sprague-Dawley Rats Following a Single Dose IV Bolus Injection of 0.64 mg/kg or 12 mg/kg.
Figure 4:
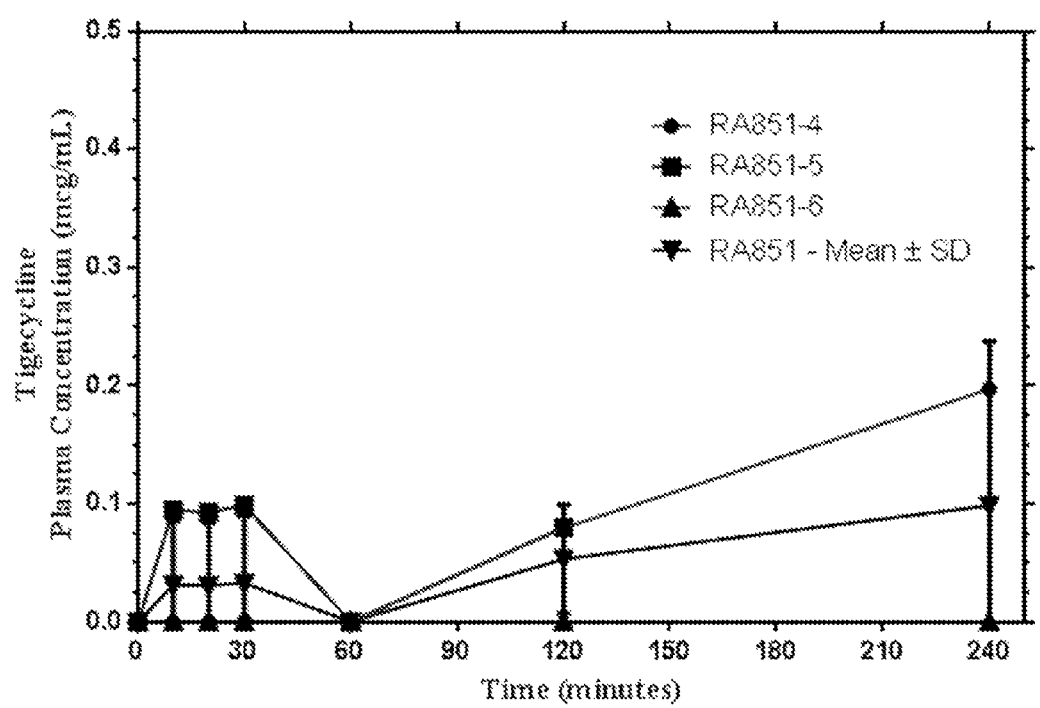
FIG. 4 is a graph showing Individual and Mean (±SD) Plasma Tigecycline Concentration in Sprague-Dawley Rats Following a Single Intraduodenal (ID) Injection formulated in PBS at 4.8 mg/kg.
Figure 5:
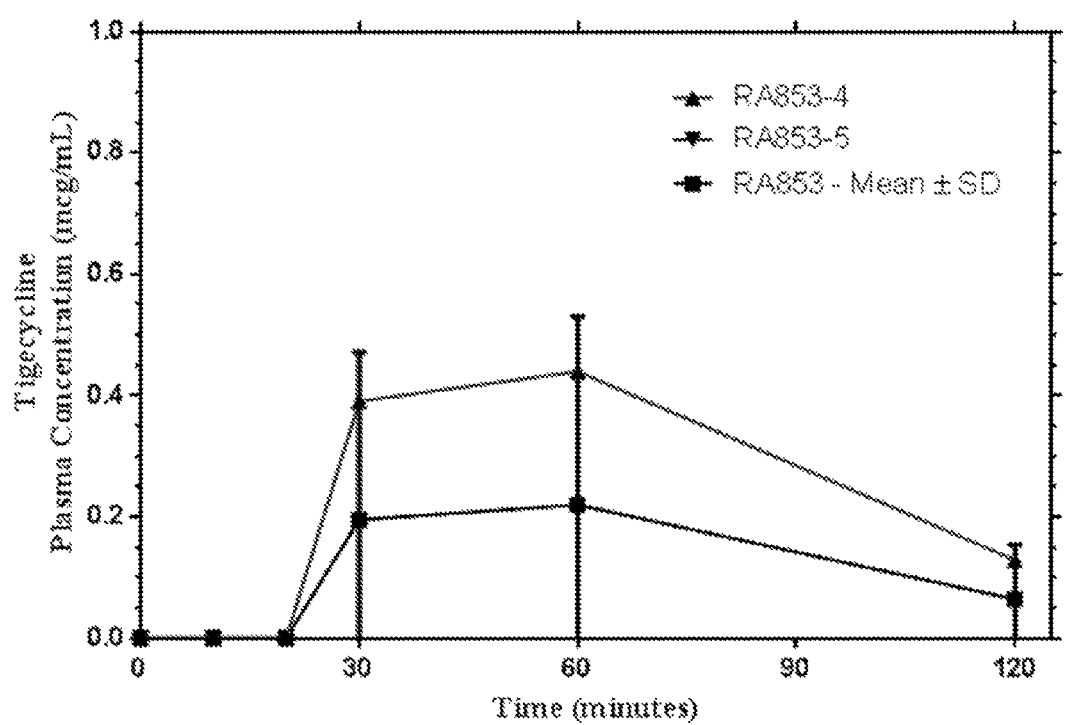
FIG. 5 is a graph showing Individual and Mean (±SD) Plasma Tigecycline Concentration in Sprague-Dawley Rats Following a Single ID Injection formulated in PBS at 9.0 mg/kg.
Figure 6:
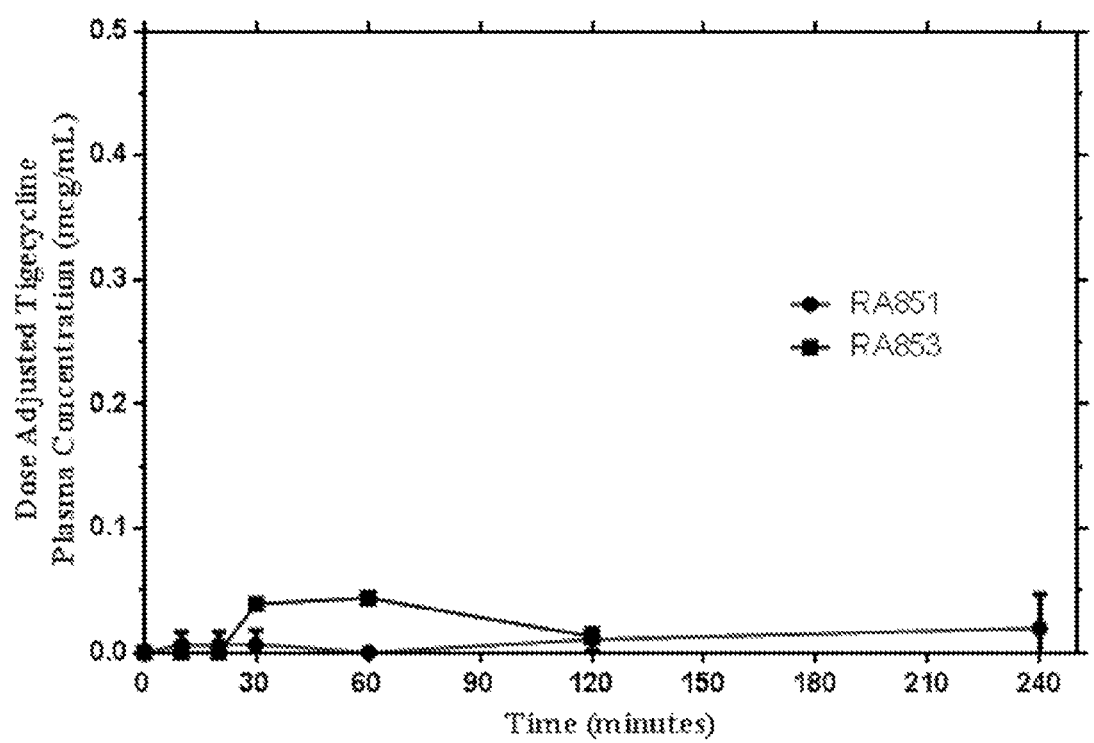
FIG. 6 is a graph showing Dose Adjusted Mean Plasma Tigecycline Concentration in Sprague-Dawley Rats Following a Single ID Injection formulated in PBS.

When the target dose was increased to 12 mg/kg (RA853), the mean C. increased to 50.7 μg/mL, which was also observed at $T_{max}$ of 5 minutes (Table 5). In both studies (RA851 and RA853), there is a clear biphasic disposition of tigecycline, which is initially extremely fast, which reaches a steady state by approximately 30 minutes (FIG. 1, FIG. 2, FIG. 3). The mean $AUC_{(0-t)}$ in study RA853 was 791 μg*min/mL.

TABLE 5

Plasma Concentrations and Pharmacokinetics of Tigecycline in Sprague-Dawley Rats Following a Single Dose IV Bolus Injection of 0.64 mg/kg or 12 mg/kg

| | Plasma Concentration (μg/mL) | | | |
|---|---|---|---|---|
| | Target Dose 0.64 mg/kg (RA851) | | Target Dose 12 mg/kg (RA853) | |
| | Mean | SEM | Mean | SEM |
| Time (min) | | | | |
| 0 | 0 | 0 | 0 | 0 |
| 5 | 1.790 | 0.268 | 50.691 | 11.954 |
| 10 | 0.888 | 0.152 | 26.194 | 6.615 |
| 20 | 0.447 | 0.026 | 9.313 | 1.749 |
| 30 | 0.376 | 0.028 | 5.758 | 0.762 |
| 60 | 0.290 | 0.025 | 2.612 | 0.481 |
| 120 | 0.216 | 0.108 | 1.866 | 0.359 |
| 240 | 0.116 | 0.116 | | |
| Parameters | | | | |
| $C_{max}$ (μg/mL) | 1.79 | 0.27 | 50.7 | 11.9 |
| $T_{max}$ (min) | 5 | 0 | 5 | 0 |
| $AUC_{(0-t)}$ (μg · min/mL) | 58.2 | 31.4 | 791 | 183 |
| Animal Weight (kg) | 0.238 | 0.018 | 0.217 | 0.012 |
| Actual Dose (mg/kg) | 0.67 | 0.053 | 13.9 | 0.751 |

Plasma Tigecycline Following ID Administration

Tigecycline was administered by ID formulated in PBS, or in 26 mM LLC with either 100 mM CA, pH 3.5, or 400 mM CA, pH 3.5. At either 4.8 or 9.0 mg/kg target doses, tigecycline administered in PBS demonstrated little to no absorption (Table 6). In RA851 (4.8 mg/kg), the mean $C_{max}$ was 0.10 μg/mL, which occurred at a mean $T_{max}$ 90 minutes, while at the higher dose, the mean $C_{max}$ was 0.22 μg/mL, occurring at a mean $T_{max}$ of 30 minutes. This last result does not include one animal which demonstrated fairly significant absorption, with a $C_{max}$ of 1.11 μg/mL at 10 minutes. The high degree of absorption, coupled with the early $T_{max}$ is uncharacteristic of the other 5 animals dosed with tigecycline formulated in PBS, indicating administration error through inadvertent ID injection site leakage (resulting in IP administration). The mean % F based on $AUC_{(0-t)}$ when dosed at 4.8 mg/kg was 1.6%, comparative to the 0.64 mg/kg IV profile. When dosed at 9.0 mg/kg, the mean % F was 2.8%.

In the presence of 26 mM LLC and 100 mM citrate, pH 3.5, the tigecycline plasma concentrations increased significantly (7-9x), PK data are summarized in Table 7. When dosed at 4.8 mg/kg (RA851), the mean tigecycline $C_{max}$ was 0.71 μg/mL, occurring at a mean $T_{max}$ of 20 minutes. The mean $AUC_{(0-t)}$ was 49.4 μg*min/mL, resulting in a calculated mean % F of 10.9% (CV 52.1% compared to 0.64 mg/kg IV). Increasing the dose to 9.0 mg/kg in the presence of 100 mM CA, 26 mM LLC also showed a significant increase in tigecycline plasma concentrations, with a mean $C_{max}$ of 2.06 μg/mL at mean $T_{max}$ of 17 minutes. The mean $AUC_{(0-t)}$ was 76.9 μg*min/mL, resulting in a mean % F of 11.4% (CV, 59.3%). In short, the mean % F increased 4-7-fold when formulated in 100 mM CA, pH 3.5, 26 mM LLC.

Increasing the citrate concentration to 400 mM, pH 3.5, in the presence of 26 mM LLC resulted in additional increases in plasma tigecycline concentrations. Chromatograms demonstrate a secondary tigecycline-related peak with a longer retention time than the parent tigecycline peak, PK data are summarized in Table 8 and Table 9. When dosed at 4.8 mg/kg, the mean C. increased to 0.79 μg/mL (1.11 μg/mL when including the secondary peak) at a mean $T_{max}$ of 17 minutes. The mean $AUC_{(0-t)}$ was 85.6 μg*min/mL (117.63 μg*min/mL including peak 2), resulting in a mean % F of 20.3% (CV, 96.6%; % F 27.9% including peak 2).

Similar to the 100 mM CA experiments, increasing the dose to 9.0 mg/kg resulted in a significant increase in plasma tigecycline. The appearance of the tigecycline-related peak was noted in this experiment as well, but it was not nearly as high comparative to the lower-dose experiment. When dosed at 9.0 mg/kg in 400 mM CA, pH 3.5, and 26 mM LLC, the mean $C_{max}$ was 2.49 μg/mL (2.88[Lg/mL when including peak 2), occurring at a mean $T_{max}$ of 10 minutes. The mean $AUC_{(0-t)}$ was 138 μg*min/mL (153 μg*min/mL including peak 2), resulting in a mean % F of 21.8% (CV, 40.8%; % F 24.13% including peak 2). FIG. 3 compares the compiled mean dose adjusted data from studies RA851 and RA853 for the different formulations studied.

TABLE 6

Plasma Concentrations and Pharmacokinetics of Tigecycline in Sprague-Dawley Rats Following a Single Dose ID Injection formulated in PBS

| | Plasma Concentration (μg/mL) | | | |
| --- | --- | --- | --- | --- |
| | Target Dose 4.8 mg/kg (RA851) | | Target Dose 9.0 mg/kg (RA853) | |
| | Mean | SEM | Mean* | SEM |
| Time (min) | | | | |
| 0 | 0 | 0 | 0 | 0 |
| 10 | 0.031 | 0.031 | 0 | 0 |
| 20 | 0.031 | 0.031 | 0 | 0 |
| 30 | 0.033 | 0.033 | 0.391 | 0 |
| 60 | 0 | 0 | 0.440 | 0 |
| 120 | 0.053 | 0.027 | 0.129 | 0 |
| 240 | 0.066 | 0.066 | | |

TABLE 6-continued

Plasma Concentrations and Pharmacokinetics of Tigecycline in Sprague-Dawley Rats Following a Single Dose ID Injection formulated in PBS

| | Plasma Concentration (μg/mL) | | | |
| --- | --- | --- | --- | --- |
| | Target Dose 4.8 mg/kg (RA851) | | Target Dose 9.0 mg/kg (RA853) | |
| | Mean | SEM | Mean* | SEM |
| Parameters | | | | |
| $C_{max}$ (μg/mL) | 0.10 | 0.06 | 0.22 | 0.22 |
| $T_{max}$ (min) | 90 | 75.5 | 30 | 30 |
| $AUC_{(0-t)}$ (μg · min/mL) | 6.96 | 6.04 | 15.74 | 15.74 |
| Animal Weight (kg) | 0.237 | 0.001 | 0.215 | 0.011 |
| Actual Dose (mg/kg) | 5.06 | 0.03 | 10.5 | 0.51 |
| % F[†] | 1.60 | 1.39 | 2.76 | 2.76 |

*Mean PK parameters do not include animal RA853-6, while mean reported plasma concentrations are representative of animal RA853-4 only due to death of RA853-5.

[†]% F for 4.8 mg/kg dose calculated relative to 0.64 mg/kg IV data, while that of 9.0 mg/kg calculated relative to 12 mg/kg IV data as those surgeries were performed on the same respective days.

TABLE 7

Plasma Concentrations and Pharmacokinetics of Tigecycline in Sprague-Dawley Rats Following a Single Dose ID Injection formulated in 100 mM CA (pH 3.5), 26 mM LLC

| | Plasma Concentration (μg/mL) | | | |
| --- | --- | --- | --- | --- |
| | Target Dose 4.8 mg/kg (RA851) | | Target Dose 9.0 mg/kg (RA853) | |
| | Mean | SEM | Mean* | SEM |
| Time (min) | | | | |
| 0 | 0 | 0 | 0 | 0 |
| 10 | 0.710 | 0.232 | 1.769 | 0.803 |
| 20 | 0.672 | 0.219 | 1.979 | 1.069 |
| 30 | 0.601 | 0.231 | 1.346 | 0.703 |
| 60 | 0.398 | 0.137 | 0.608 | 0.287 |
| 120 | 0.306 | 0.074 | 0.273 | 0.185 |
| 240 | | | | |
| Parameters | | | | |
| $C_{max}$ (μg/mL) | 0.714 | 0.234 | 2.060 | 1.024 |
| $T_{max}$ (min) | 20 | 5.774 | 16.667 | 3.333 |
| $AUC_{(0-t)}$ (μg · min/mL) | 49.4 | 16.0 | 76.9 | 28.5 |
| Animal Weight (kg) | 0.231 | 0.006 | 0.193 | 0.006 |
| Actual Dose (mg/kg) | 5.20 | 0.13 | 11.7 | 0.38 |
| % F[†] | 10.85 | 3.26 | 11.36 | 3.89 |

[†]% F for 4.8 mg/kg dose calculated relative to 0.64 mg/kg IV data, while that of 9.0 mg/kg calculated relative to 12 mg/kg IV data as those surgeries were performed on the same respective days.

TABLE 8

Plasma Concentrations and Pharmacokinetics of Tigecycline in Sprague-Dawley Rats Following a Single Dose ID Injection formulated in 400 mM CA (pH 3.5), 26 mM LLC (using parent Tigecycline peak only)

| | Plasma Concentration (μg/mL) | | | |
|---|---|---|---|---|
| | Target Dose 4.8 mg/kg (RA851) | | Target Dose 9.0 mg/kg (RA853) | |
| | Mean | SEM | Mean* | SEM |
| Time (min) | | | | |
| 0 | 0 | 0 | 0 | 0 |
| 10 | 0.920 | 0.468 | 2.492 | 0.405 |
| 20 | 0.788 | 0.337 | 2.160 | 0.525 |
| 30 | 0.618 | 0.291 | 1.764 | 0.489 |
| 60 | 0.455 | 0.231 | 1.061 | 0.287 |
| 120 | 0.345 | 0.151 | 0.683 | 0.139 |
| 240 | 0.386 | 0.176 | | |
| Parameters | | | | |
| $C_{max}$ (μg/mL) | 0.792 | 0.335 | 2.492 | 0.405 |
| $T_{max}$ (min) | 16.7 | 3.33 | 10 | 0 |
| $AUC_{(0-t)}$ (μg · min/mL) | 85.6 | 47.3 | 137.6 | 33.6 |
| Animal Weight (kg) | 0.245 | 0.003 | 0.204 | 0.002 |
| Actual Dose (mg/kg) | 4.90 | 0.05 | 11.0 | 0.13 |
| % F† | 20.30 | 11.3 | 21.8 | 5.13 |

†% F for 4.8 mg/kg dose calculated relative to 0.64 mg/kg IV data, while that of 9.0 mg/kg calculated relative to 12 mg/kg IV data as those surgeries were performed on the same respective days.

TABLE 9

Plasma Concentrations and Pharmacokinetics of Tigecycline in Sprague-Dawley Rats Following a Single Dose ID Injection formulated in 400 mM CA (pH 3.5), 26 mM LLC (including Tigecycline-related Peak)

| | Plasma Concentration (μg/mL) | | | |
|---|---|---|---|---|
| | Target Dose 4.8 mg/kg | | Target Dose 9.0 mg/kg | |
| | Mean | SEM | Mean* | SEM |
| Time (min) | | | | |
| 0 | 0 | 0 | 0 | 0 |
| 10 | 1.257 | 0.603 | 2.877 | 0.429 |
| 20 | 1.076 | 0.463 | 2.496 | 0.581 |
| 30 | 0.869 | 0.414 | 2.057 | 0.556 |
| 60 | 0.625 | 0.328 | 1.222 | 0.371 |
| 120 | 0.485 | 0.225 | 0.782 | 0.191 |
| 240 | 0.511 | 0.200 | | |
| Parameters | | | | |
| $C_{max}$ (μg/mL) | 1.112 | 0.443 | 2.877 | 0.429 |
| $T_{max}$ (min) | 16.7 | 3.33 | 10 | 0 |
| $AUC_{(0-t)}$ (μg · min/mL) | 117.6 | 66.9 | 152.8 | 46.8 |
| Animal Weight (kg) | 0.245 | 0.003 | 0.204 | 0.002 |
| Actual Dose (mg/kg) | 4.90 | 0.05 | 11.1 | 0.13 |
| % F† | 27.90 | 16.01 | 24.13 | 7.22 |

†% F for 4.8 mg/kg dose calculated relative to 0.64 mg/kg IV data, while that of 9.0 mg/kg calculated relative to 12 mg/kg IV data as those surgeries were performed on the same respective days.

Mechanistic Feasibility Assessments (RA861, RA867, RA869)

The positive data from the primary feasibility studies necessitated investigation into the individual contributions of each active excipient (CA and LLC). Therefore, additional studies were conducted comparing the % F and PK profiles of tigecycline administered formulated in one of each of the active excipients (RA861 and RA869), comparative to the highest % F formulation from the primary feasibility studies (400 mM CA, pH 3.5, and 26 mM LLC from studies RA851 and RA853). An additional study was conducted exploring the effect of formulation pH at constant CA and LLC concentrations (RA867).

RA861 was designed with three ID injection arms, 400 mM CA, pH 3.5, with 26 mM LLC as a control, 400 mM CA, pH 3.5, alone and a third arm formulated with 26 mM LLC alone. Results demonstrated extremely low exposure comparative to the primary feasibility studies, an issue which was believed to have stemmed from the analytical method. These issues necessitated study RA869, which was essentially a repeat of RA861, but replacing the CA only arm with an IV comparator. In short, both studies demonstrate the utility of CA as an enabling excipient for tigecycline. While PK data from study RA869 replicated the approximately 22% % F when dosed in 400 mM CA, pH 3.5, and 26 mM LLC (RA851, RA853), dosing with only 26 mM LLC resulted in a mean 9% F.

Study RA867 compared tigecycline % F and PK when dosed in formulations at different pH. This study contained two formulation arms, where six rats each were ID dosed with 400 mM CA and 26 mM LLC at either pH 3.5, or pH 6.0. Data demonstrate that rats dosed with formulation at pH 3.5 demonstrate higher $C_{max}$, earlier $T_{max}$ and higher $AUC_{(0-t)}$. These data would suggest the import of pH, rather than calcium sequestration as the predominating mechanism underlying CA function as an enabling excipient for this small molecule.

TABLE 10

Summary of Mean Tigecycline Pharmacokinetic Parameters in Female Sprague-Dawley Rats With Varying pH, CA and/or LLC Content (% CV)

| Study | Study Arm | Mean Dose (mg/kg) | N | $C_{max}$ (ng/mL) | $T_{max}$ (min) | $AUC_{(0-t)}$ (ng * min/mL) | % F |
|---|---|---|---|---|---|---|---|
| RA861 | 400 mM CA/26 mM LLC | 4.6 | 4 | 30.6 (48.1) | 10 (0) | 8314 (61.5) | 2.1 (61.9) |

TABLE 10-continued

Summary of Mean Tigecycline Pharmacokinetic Parameters in Female Sprague-Dawley Rats With Varying pH, CA and/or LLC Content (% CV)

| Study | Study Arm | Mean Dose (mg/kg) | N | $C_{max}$ (ng/mL) | $T_{max}$ (min) | $AUC_{(0-t)}$ (ng * min/mL) | % F |
|---|---|---|---|---|---|---|---|
| | 400 mM CA | 4.8 | 4 | 11.7 (125) | 20 (173) | 1050 (195) | 0.3 (195) |
| | 26 mM 2LLC | 4.6 | 4 | 64.1 (62.9) | 18 (54.7) | 4082 (93.9) | 1.0 (92.3) |
| RA867 | 400 mM CA/26 mM LLC pH 3.5 | 4.8 | 6 | 488 (48.0) | 12 (35.0) | 32202 (48.8) | 7.7 (47.1) |
| | 400 mM CA/26 mM LLC pH 6.0 | 4.8 | 6 | 278 (35.1) | 43 (87.2) | 23127 (37.0) | 5.5 (37.2) |
| RA869 | IV | 0.6 | 2 | 369 (39.9) | 7.5 (47.1) | 7893 (23.3) | — |
| | 400 mM CA/26 mM LLC | 4.5 | 2 | 246 (17.9) | 15 (47.1) | 13339 (0.12) | 21.6 (5.47) |
| | 26 mM LLC | 4.5 | 2 | 105 (47.0) | 10 (0) | 5500 (60.3) | 8.9 (59.9) |

Primary Feasibility Studies (RA851, RA853)

These studies demonstrated the feasibility of improving the oral % F of tigecycline, a BCS Class III antibiotic, using the combination of citrate buffer (pH 3.5) and LLC in the anesthetized rat model. Intraduodenal administration was utilized to mimic administration of an enterically coated dosage form in larger mammals. Neither these primary feasibility studies, nor the mechanistic studies discussed below, were designed to explore whether or not enterically coating the dosage form is a necessity for small molecules. From a theoretical perspective, given the mechanism of permeation, enteric coating should be preferred from a variation point of view since it would limit potential food and dilution effects.

Figure 7:
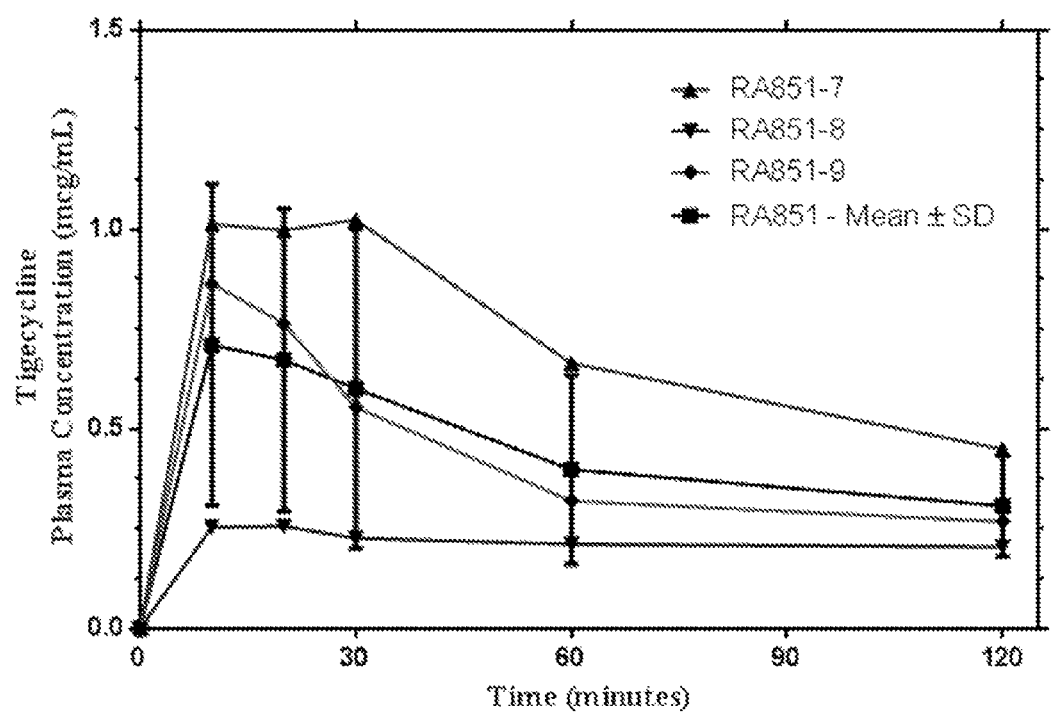
FIG. 7 is a graph showing Individual and Mean (±SD) Plasma Tigecycline Concentration in Sprague-Dawley Rats Following a Single ID Injection formulated in 100 mM citric acid (CA) (pH 3.5), 26 mM lauroyl-L-carnitine (LLC) at 4.8 mg/kg.
Figure 8:
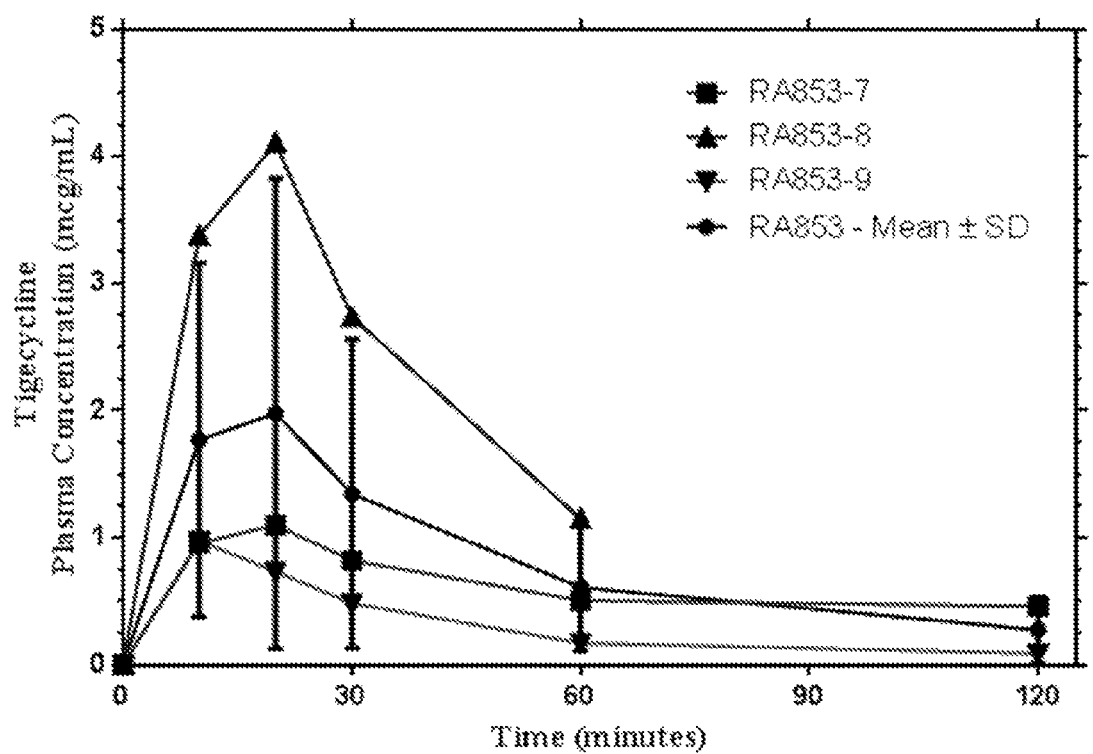
FIG. 8 is a graph showing Individual and Mean (±SD) Plasma Tigecycline Concentration in Sprague-Dawley Rats Following a Single ID Injection formulated in 100 mM CA (pH 3.5), 26 mM LLC at 9.0 mg/kg.
Figure 9:
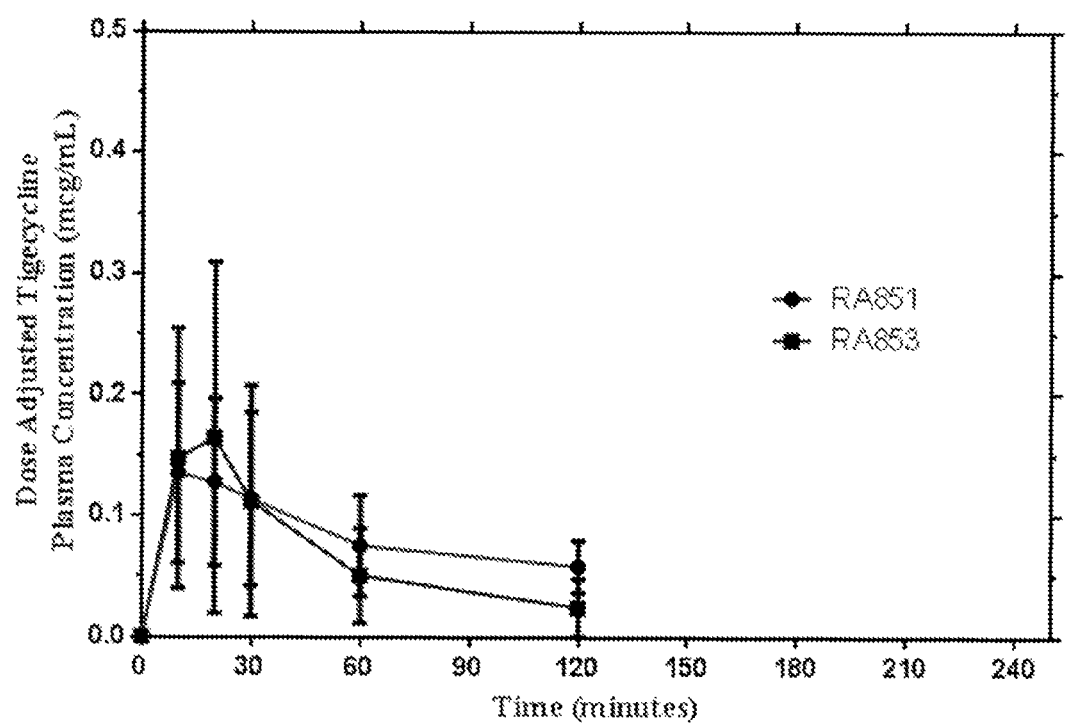
FIG. 9 is a graph showing Dose Adjusted Mean Plasma Tigecycline Concentration in Sprague-Dawley Rats Following a Single ID Injection Formulated in 100 mM CA (pH 3.5), 26 mM LLC.
Figure 10:
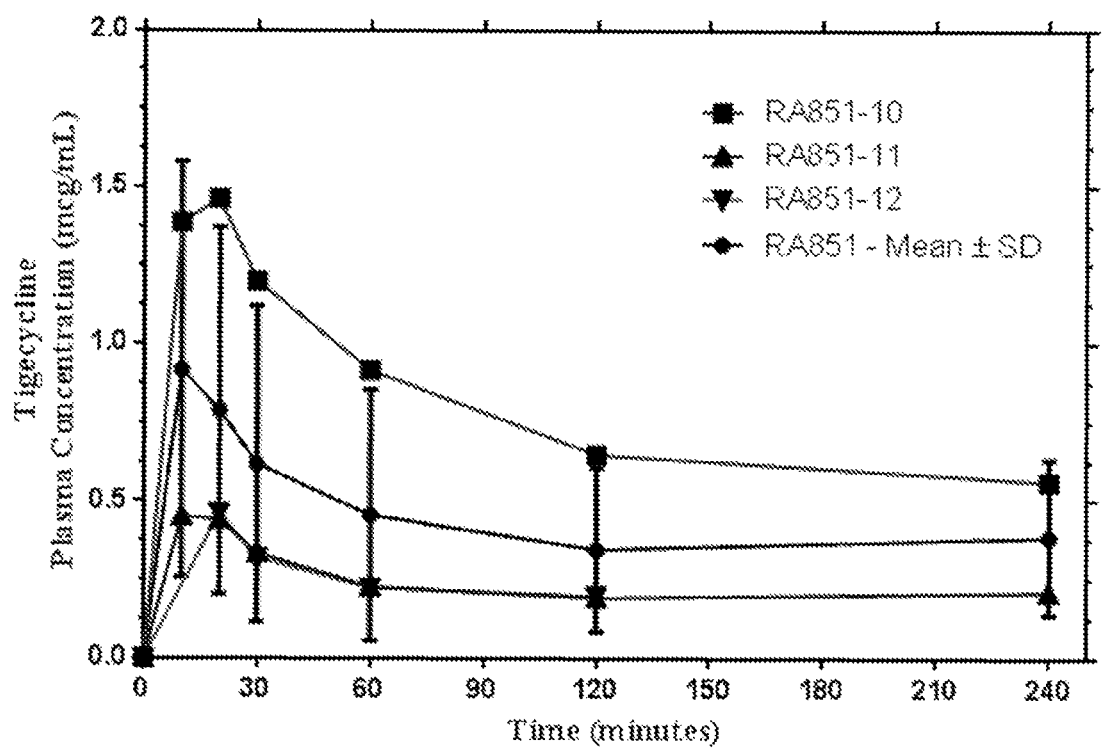
FIG. 10 is a graph showing Individual and Mean (±SD) Plasma Tigecycline Concentration in Sprague-Dawley Rats Following a Single ID Injection formulated in 400 mM CA (pH 3.5), 26 mM LLC at 4.8 mg/kg (using parent Tigecycline peak only).
Figure 11:
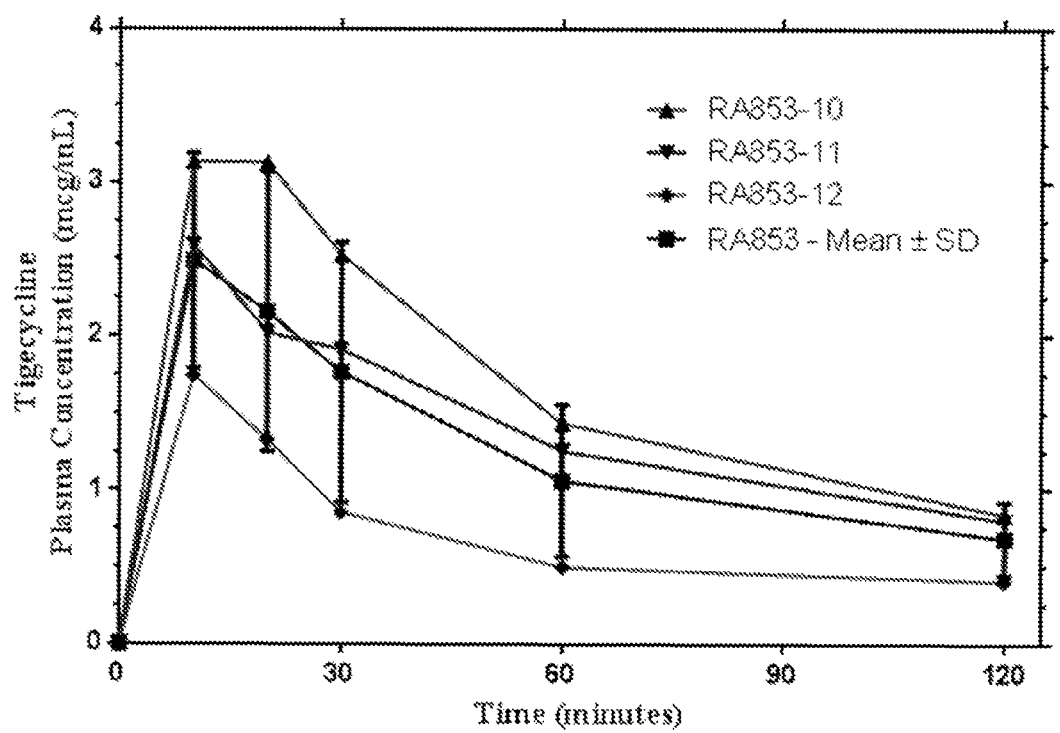
FIG. 11 is a graph showing Individual and Mean (±SD) Plasma Tigecycline Concentration in Sprague-Dawley Rats Following a Single ID Injection formulated in 400 mM CA (pH 3.5), 26 mM LLC at 9.0 mg/kg (using parent Tigecycline peak only).
Figure 12:
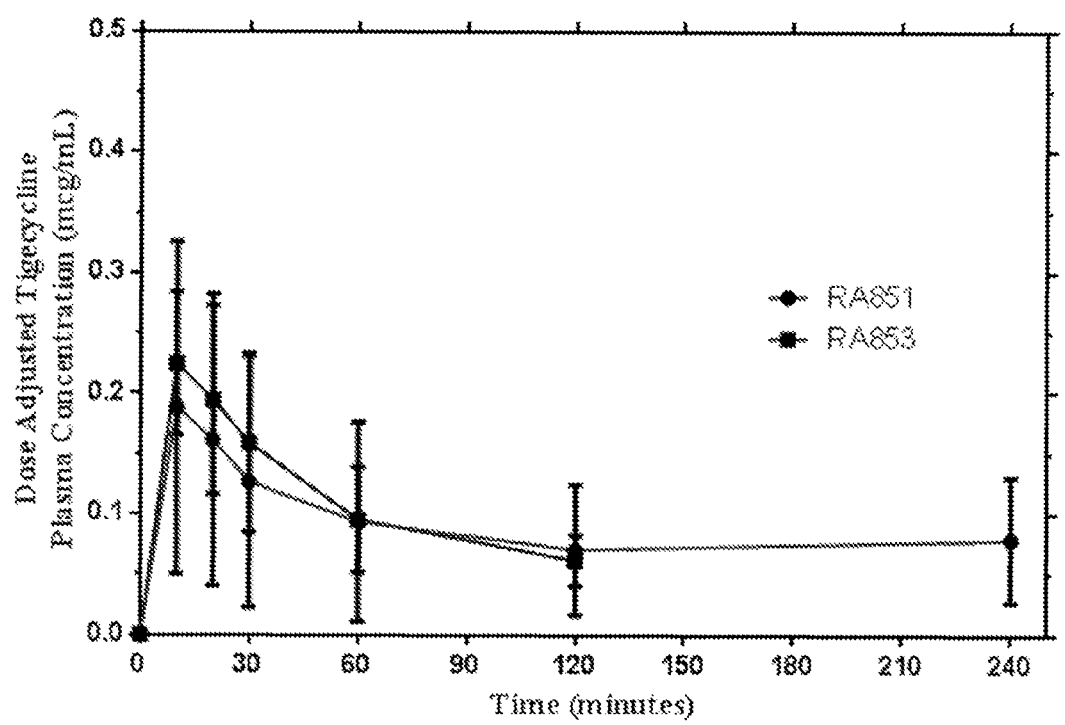
FIG. 12 is a graph showing Dose Adjusted Mean Plasma Tigecycline Concentration in Sprague-Dawley Rats Following a Single ID Injection Formulated in 400 mM CA (pH 3.5), 26 mM LLC (using parent Tigecycline peak only).
Figure 13:
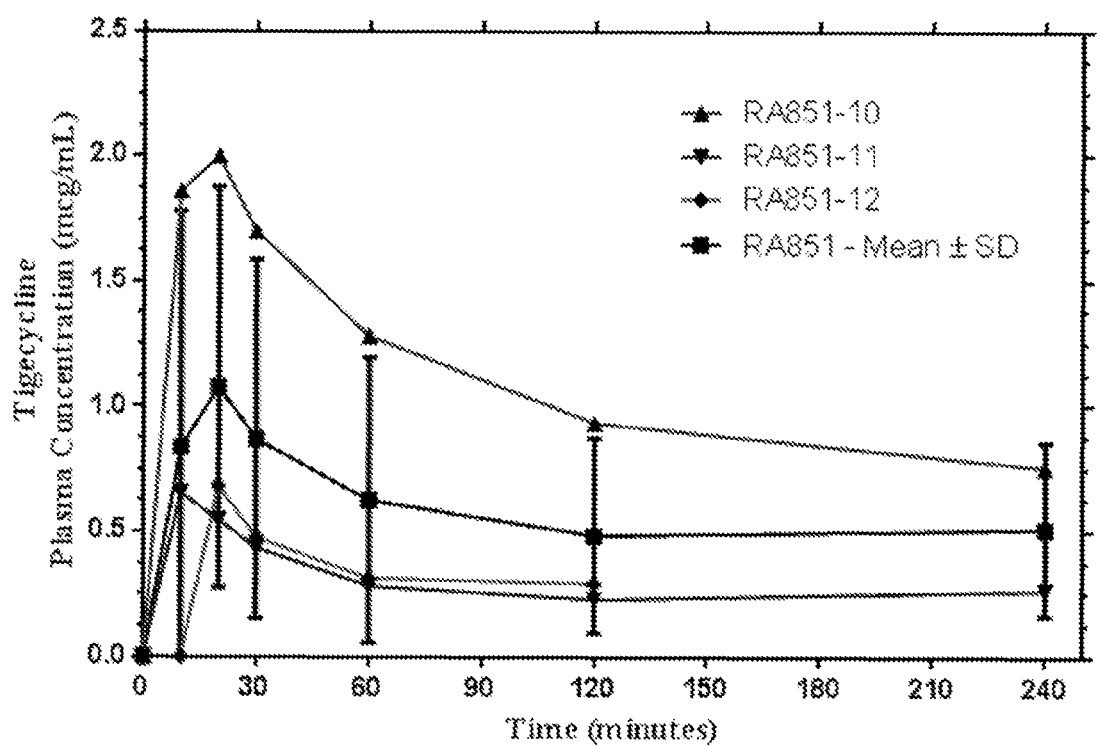
FIG. 13 is a graph showing Individual and Mean (±SD) Plasma Tigecycline Concentration in Sprague-Dawley Rats Following a Single ID Injection formulated in 400 mM CA (pH 3.5), 26 mM LLC at 4.8 mg/kg (including Tigecycline-related peak).
Figure 14:
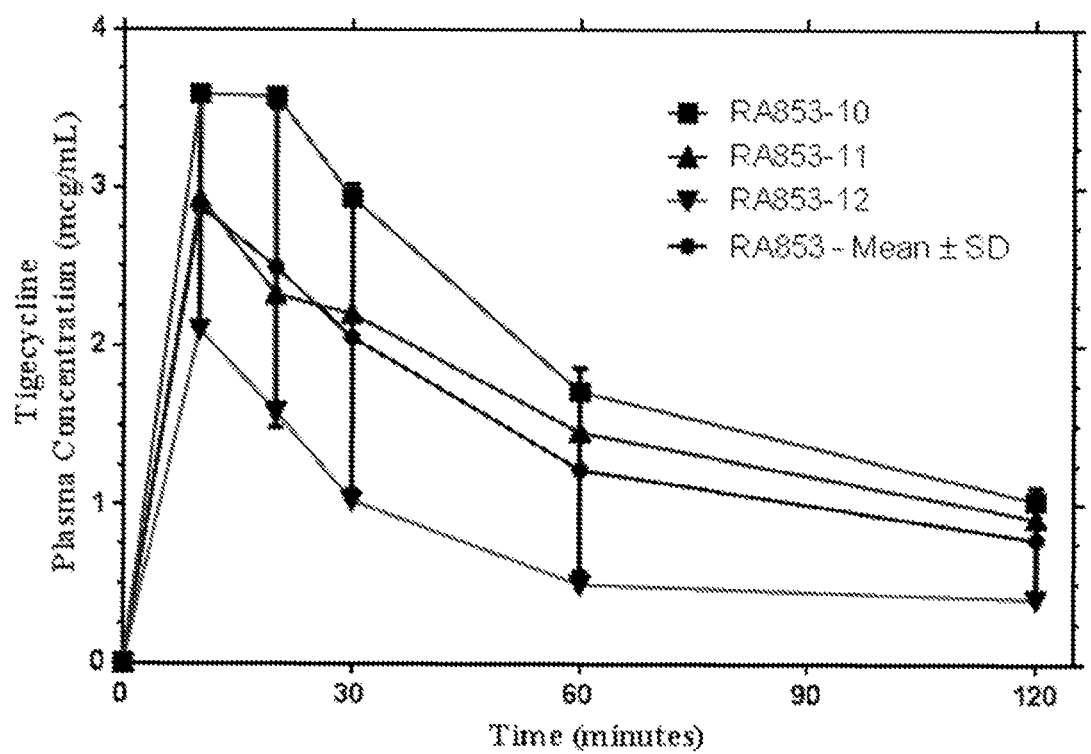
FIG. 14 is a graph showing Individual and Mean (±SD) Plasma Tigecycline Concentration in Sprague-Dawley Rats Following a Single ID Injection formulated in 400 mM CA (pH 3.5), 26 mM LLC at 9.0 mg/kg (including Tigecycline-related peak).
Figure 15:
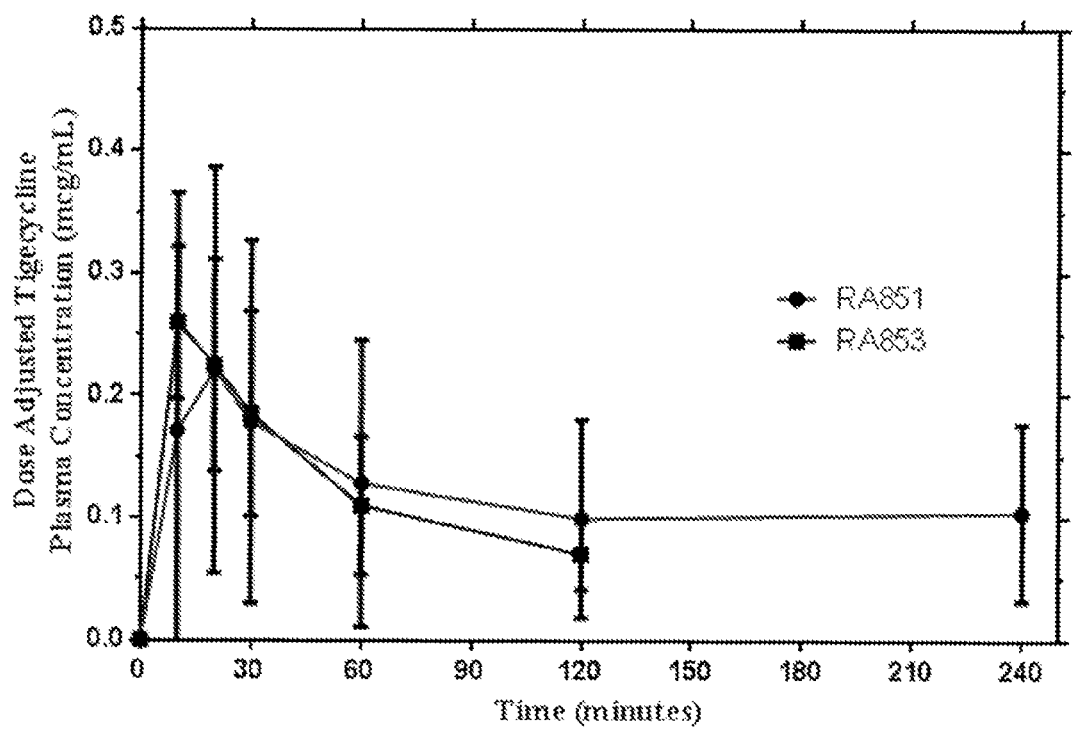
FIG. 15 is a graph showing Dose Adjusted Mean Plasma Tigecycline Concentration in Sprague-Dawley Rats Following a Single ID Injection Formulated in 400 mM CA (pH 3.5), 26 mM LLC (including Tigecycline-related Peak).

Intravenous administration of tigecycline resulted in an expected biphasic, first order plasma concentration curve. Given the variable and relatively low tigecycline plasma concentrations observed in the disposition phase of ID administered tigecycline in study RA851 (FIG. 7 and FIG. 10), the studies were repeated at higher dose (RA853). From a theoretical perspective, one way to overcome low exposure upon dosing a BCS Class III compound is by increasing the local concentration available for absorption (i.e., the dose). Commensurate with a passive absorption mechanism, while overall exposure was directly dependent on the dose, the dose adjusted PK curves were virtually superimposable (FIGS. 3, 9, 12 and 15).

Figure 16:
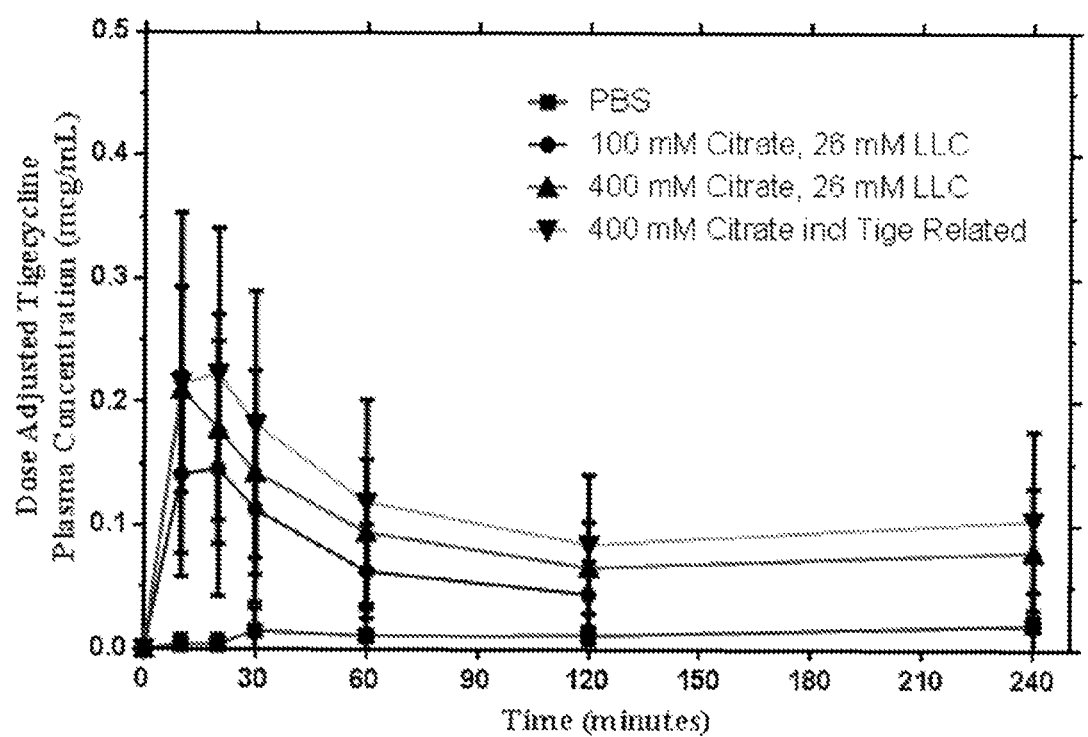
FIG. 16 is a graph showing Mean Dose Adjusted Plasma Tigecycline Concentrations in Sprague-Dawley Rats Following Single ID Injections of Various Formulations from Primary Feasibility Studies RA851 and RA853.
Figure 17:
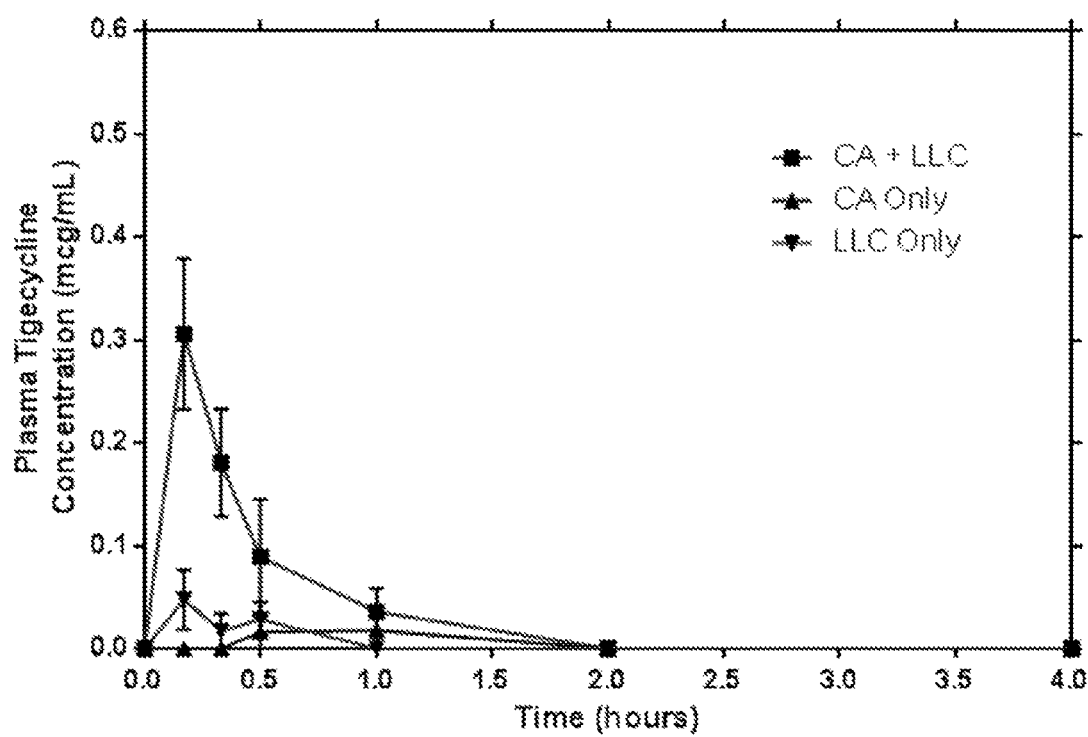
FIG. 17 is a graph showing Study RA861-Mean (±SD) Plasma Tigecycline Concentrations in Sprague-Dawley Rats Following a Single ID Injection.
Figure 18:
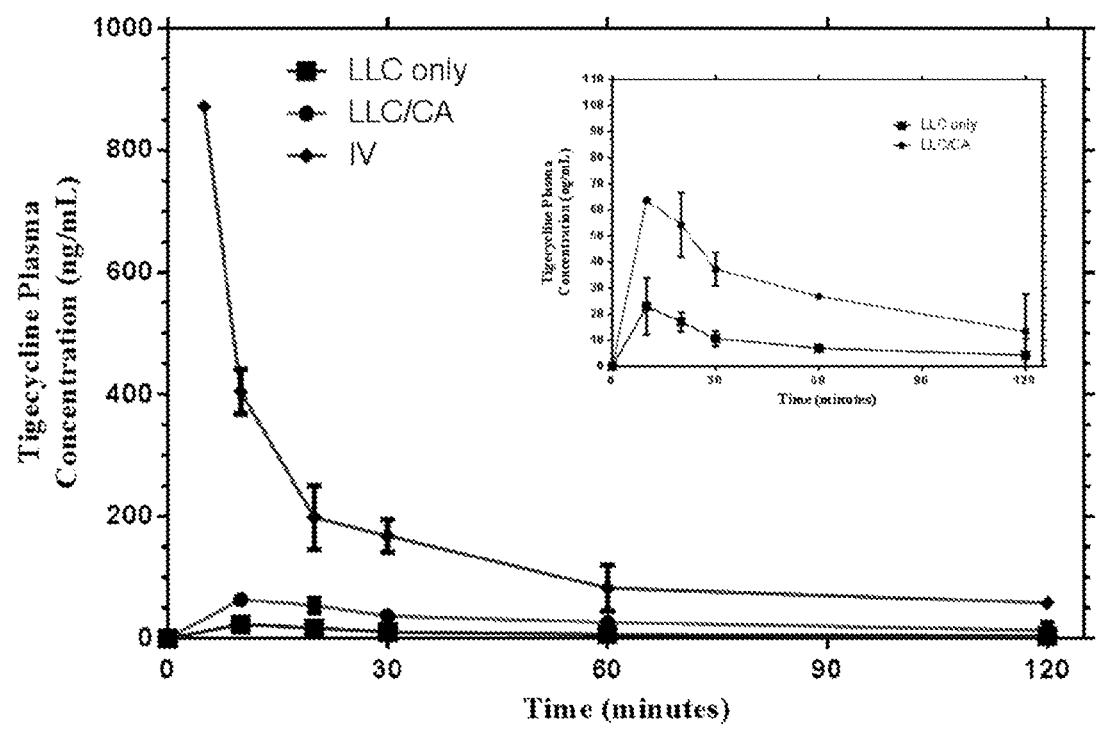
FIG. 18 is a graph showing Study RA869 -Dose Adjusted Mean (±SD) Plasma Tigecycline Concentrations in Sprague-Dawley Rats.
Figure 19:
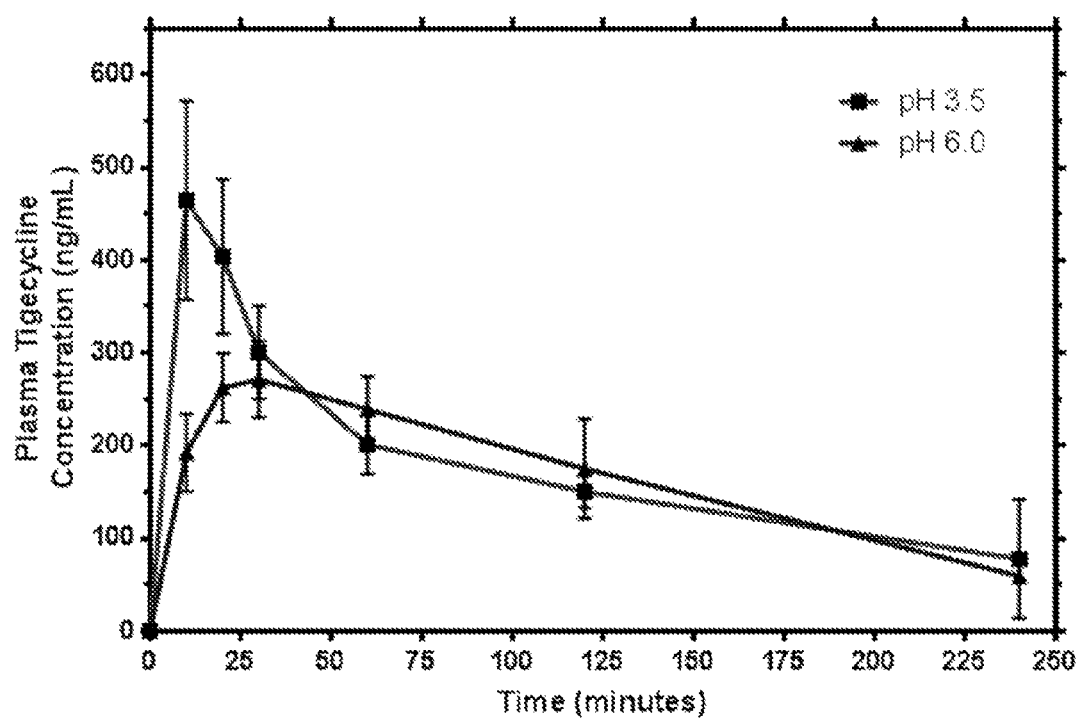
FIG. 19 is a graph showing Study RA867-Mean (±SD) Plasma Tigecycline Concentrations in Sprague-Dawley Rats Following Single ID Administration of Tigecycline Formulated in 400 mM CA, 26 mM LLC at pH 3.5 vs. pH 6.0.

For small molecule therapeutics, which in general, do not require the acidifying activity of CA to inhibit metabolic enzymes, we hypothesized that CA would still be beneficial as an enabling excipient for certain BCS compounds. Indeed, the absolute tigecycline % F was also dependent on CA concentration, demonstrating its potential utility as both a solubilizing excipient (in this specific case only), as well as a permeation enhancer. Tetracycline analogues are known to interact with bile salts in the presence of calcium ions, resulting in complex precipitation. Citric acid can disrupt these interactions by either chelating calcium, or by acidification of the milieu, thereby disrupting these bile salt interactions and making the active available for absorption. The absolute tigecycline % F was approximately 11% when formulated with 100 mM CA, pH 3.5, and 26 mM LLC, which increased to approximately 22% when formulated with 400 mM CA, pH 3.5, and 26 mM LLC (Table 11 and FIG. 16).

TABLE 11

Summary of Mean Tigecycline Pharmacokinetic Parameters in Female Sprague-Dawley Rats (% CV)

| Study | Study Arm | Mean Dose (mg/kg) | N | $C_{max}$ (µg/mL) | $T_{max}$ (min) | $AUC_{(0-t)}$ (µg * min/mL) | % F* |
|---|---|---|---|---|---|---|---|
| RA851 | IV | 0.7 | 3 | 1.79 (25.9) | 5 (0) | 58.2 (53.9) | — |
| | PBS | 5.1 | 3 | 0.10 (99.9) | 90 (145) | 6.96 (150) | 1.6 (150) |
| | 100 mM CA/26 mM LLC | 5.2 | 3 | 0.71 (56.7) | 20 (50) | 49.4 (56.0) | 10.9 (52.1) |
| | 400 mM CA/26 mM LLC | 4.9 | 3 | 0.79 (73.3) | 17 (34.5) | 85.6 (95.7) | 20.3 (96.6) |
| RA853 | IV | 13.9 | 3 | 50.7 (40.8) | 5 (0) | 791 (40.1) | — |
| | PBS | 11.1 | 2 | 0.22 (141) | 30 (141) | 15.7 (141) | 2.8 (141) |
| | 100 mM CA/26 mM LLC | 11.7 | 3 | 2.06 (86.1) | 17 (34.6) | 76.9 (64.3) | 11.4 (59.3) |

TABLE 11-continued

Summary of Mean Tigecycline Pharmacokinetic Parameters in Female Sprague-Dawley Rats (% CV)

| Study | Study Arm | Mean Dose (mg/kg) | N | $C_{max}$ (μg/mL) | $T_{max}$ (min) | $AUC_{(0-t)}$ (μg * min/mL) | % F* |
|---|---|---|---|---|---|---|---|
| | 400 mM CA/26 mM LLC | 11.0 | 3 | 2.49 (28.1) | 10 (0) | 138 (42.3) | 21.8 (40.8) |

*% F was calculated comparative to the respective IV arm of each study.

It should be stressed that the data for tigecycline formulated in 400 mM CA, pH 3.5, with 26 mM LLC presented in Table 11 are for tigecycline only. Upon analysis, it was noted that for both studies RA851 and RA853, chromatograms for plasma samples from this formulation exhibited a fairly significant peak with a longer retention time than the tigecycline peak. This unknown peak (termed tigecycline-related peak) was not observed in the time zero plasma samples for the individual animals, was observed in all subsequent time points and the level corresponded/followed the levels of tigecycline. It is hypothesized that this peak could potentially be a tigecycline degradation product, perhaps a citrate adduct, as there was some storage time between sample acquisition and subsequent analysis, however the peak has not been identified. Further supporting the degradation theory is that this peak was not observed in the mechanistic studies discussed below (specifically RA867 or RA869), where storage time was minimal. However, given that this peak has not been identified, it has not been included in the overall summaries. Including the peak would result in an absolute % F of approximately 28% in RA851 and 24% in RA853 (Table 9).

Figure 20:
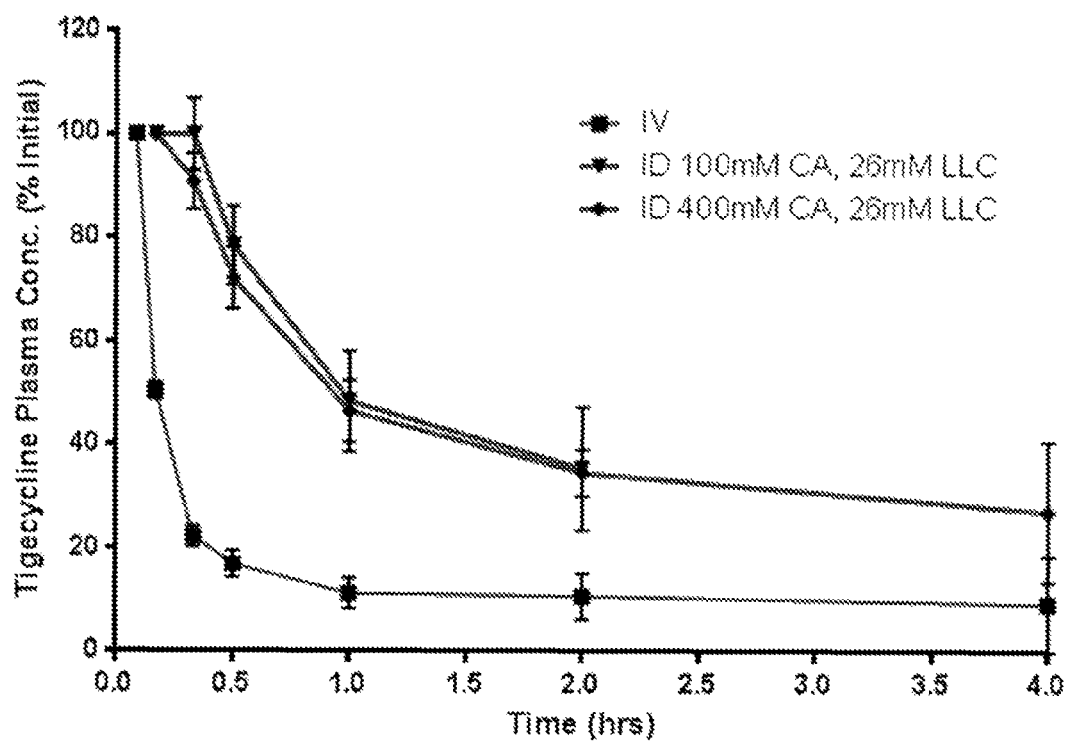
FIG. 20 is a graph showing Mean Plasma Tigecycline Clearance Defined as Percent of Initial in Sprague-Dawley Rats Following Single ID Administration (Studies RA851 and RA853).
Figure 21:
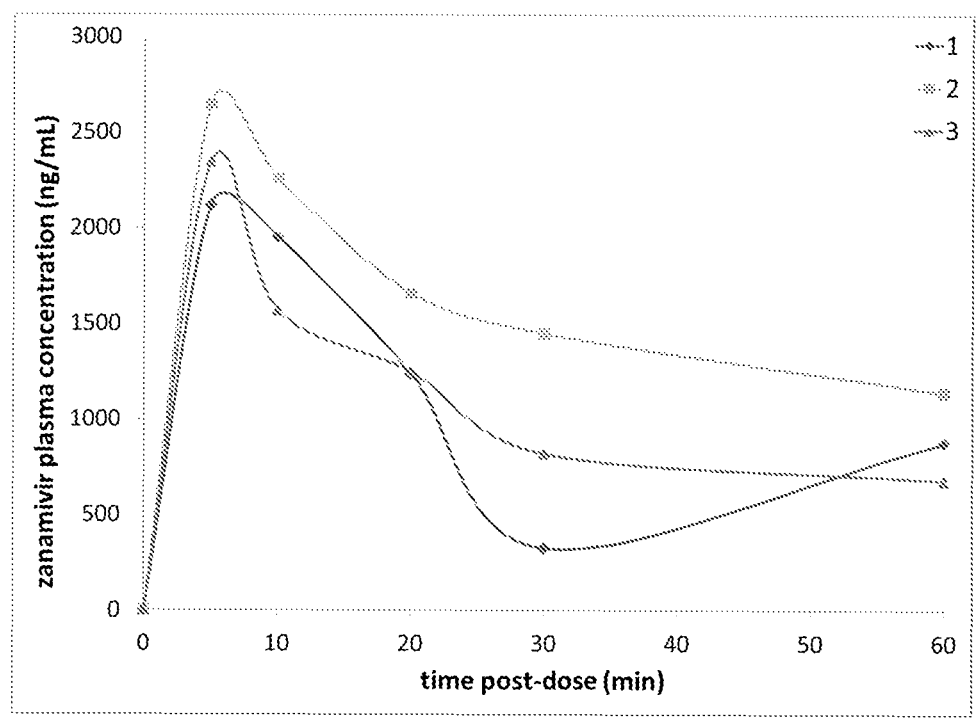
FIG. 21 is a graph showing Individual PK Profiles for IV Formulation.
Figure 22:
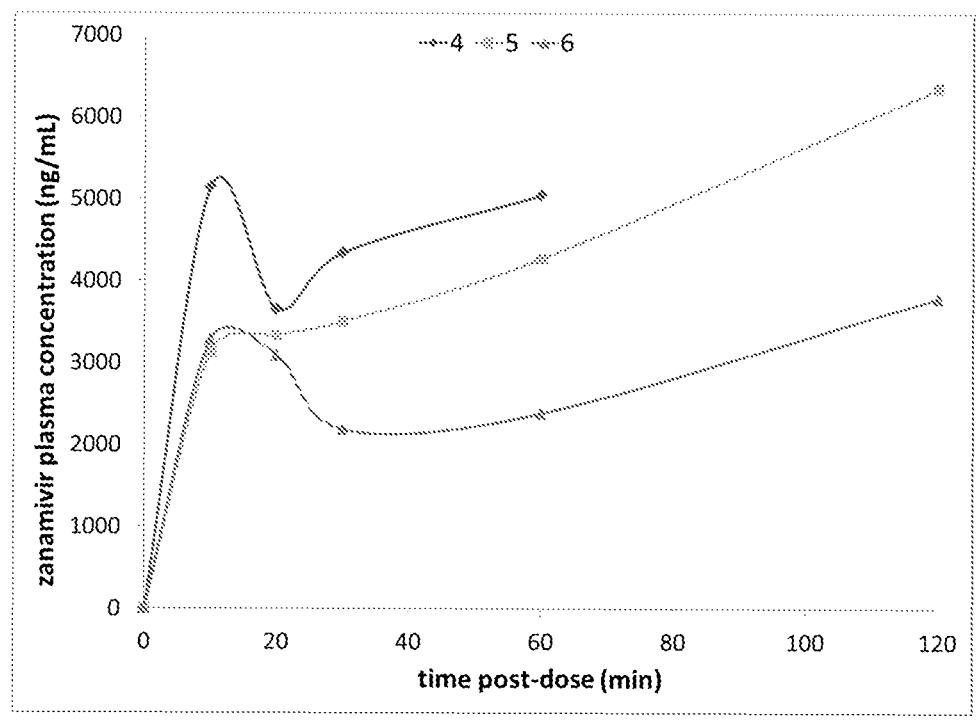
FIG. 22 is a graph showing Individual PK Profiles for Formulation A.
Figure 23:
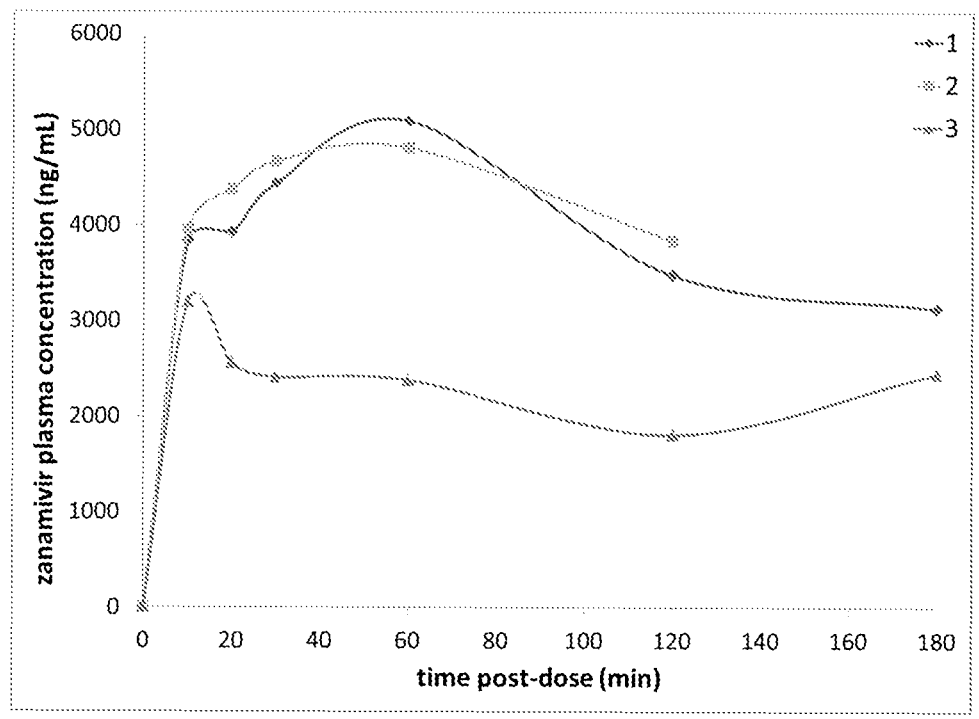
FIG. 23 is a graph showing Individual PK Profiles for Formulation PBS.
Figure 24:
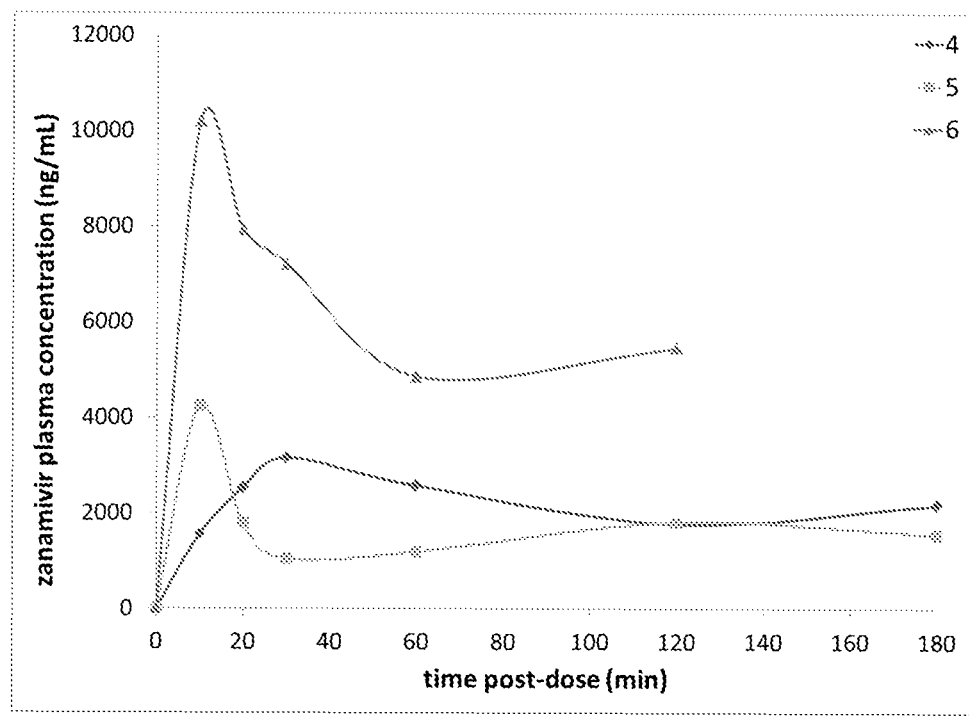
FIG. 24 is a graph showing Individual PK Profiles for Formulation B.
Figure 25:
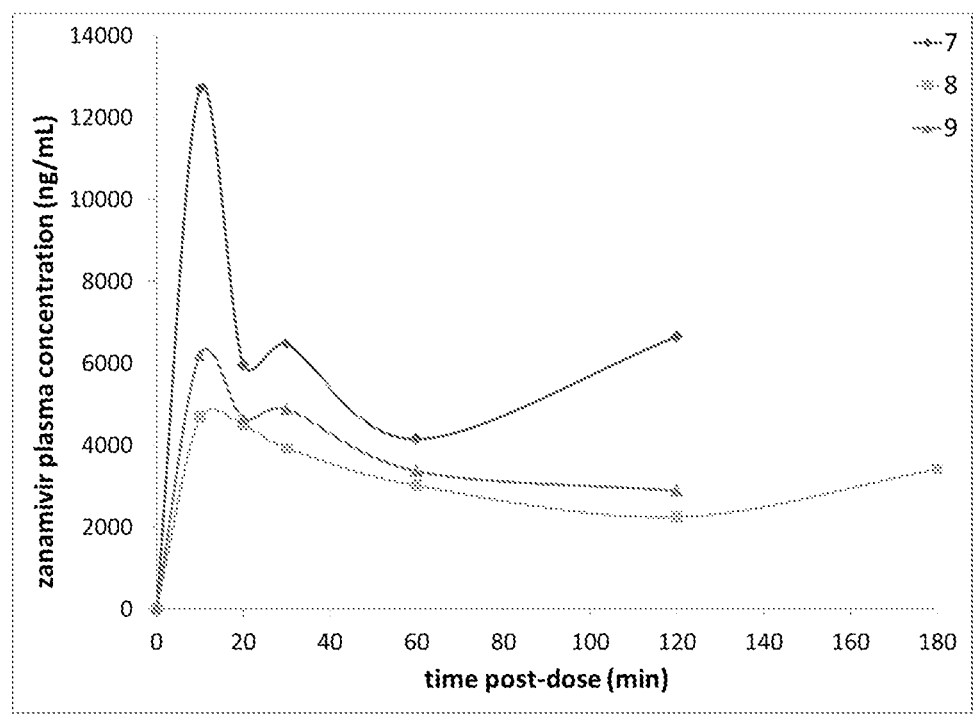
FIG. 25 is a graph showing Individual PK Profiles for Formulation C.
Figure 26:
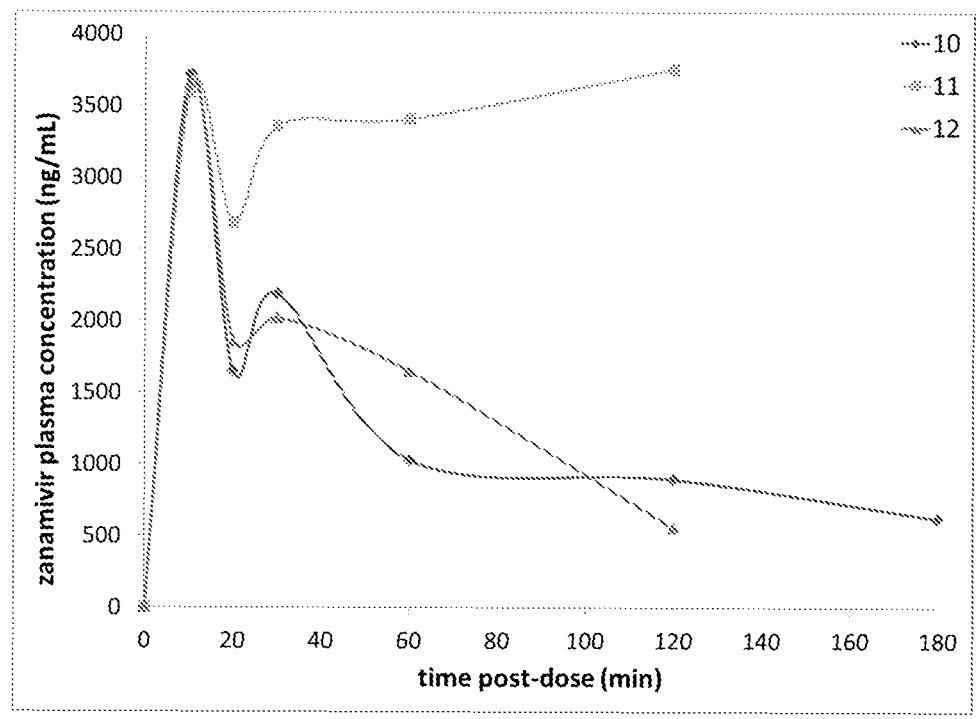
FIG. 26 is a graph showing Individual PK Profiles for Formulation D.

Interestingly, when comparing the IV to the ID PK profiles, the disposition phases of the curves are dramatically different (FIG. 20). Given the slower disposition (higher percent initial with respect to time), one can surmise that the bioavailabilities are underestimated by the limited time of sample collection. Further studies would be required to determine why the disposition of ID administered tigecycline is slower than IV. One can suggest preferential tissue deposition, given the reported high steady state volume of distribution of tigecycline, but this is clearly speculation. It will be interesting to see if this finding is replicated in the dog model, especially considering differences in hepatic and biliary anatomy and function in rat versus dog.

Mechanistic Feasibility Assessments (RA861, RA867, RA869)

The positive data from the primary feasibility studies necessitated investigation into the individual contributions of each active excipient (CA and LLC). Therefore, additional studies were conducted comparing the % F and PK profiles of tigecycline formulated in one of each active excipient (RA861 and RA869), compared to the highest % F formulation from the primary feasibilities (400 mM CA, pH 3.5, and 26 mM LLC from studies RA851 and RA853). An additional study was conducted exploring the effect of formulation pH at constant CA and LLC concentrations (RA867).

Studies designed to assess the relative individual contributions of CA and LLC (RA861 and RA869) demonstrate the utility of CA as an enabling excipient for an oral formulation of tigecycline. Potential analytical method issues aside, results from study RA869 replicate the relatively high absolute % F (22%) when formulated in 400 mM CA, pH 3.5, and 26 mM LLC, but also show 9% absolute tigecycline % F when dosed in only 26 mM LLC (no CA; Table 10). These studies not only support the concomitant use of CA and LLC together, but offer further avenues of study into the observed synergism of the combination.

To this end, study RA867 was conducted to determine if the effects of CA were indeed due to the physicochemical nature of citrate, or due to the low pH. This study compared tigecycline % F and PK when dosed in formulations of identical compositions (400 mM citrate, 26 mM LLC), at either pH 3.5, or pH 6.0. Data demonstrate that rats dosed with the formulation at pH 3.5 demonstrate higher $C_{max}$, earlier $T_{max}$ and higher $AUC_{(0-t)}$. These data would suggest the import of pH, rather than calcium sequestration as the predominating mechanism underlying the function of CA as an enabling excipient for this small molecule. Additional studies, which remove potential confounders, are required to fully elucidate the utility of acidic pH for this compound. For example, other studies to demonstrate the effects of milieu acidification on permeability enhancement, which is a known permeation enhancement mechanism. In this instance, acidification would have the added benefit of disrupting tigecycline-bile salt complexation. While higher pH citrate would be a better calcium chelator (reported pKa's at 3.1, 4.7 and 6.4), which would also disrupt the tigecycline-bile salt interactions and enhance permeation, it's unclear how effective calcium chelation would be in disrupting the bile salt interactions. In short, the observed difference in % F could simply be a function of insolubility.

Studies presented in Example 1 demonstrate an embodiment of a drug used in a pharmaceutical composition of the present invention, wherein pharmaceutical composition is for oral delivery of the BCS Class III small molecule. The absolute % F of tigecycline delivered by ID injection and formulated in PBS was 1.6% at low dose (RA851) and 2.8% at high dose (RA853). When tigecycline was formulated in 100 mM CA, pH 3.5, and 26 mM LLC, the absolute % F increased to approximately 11%. Increasing the CA content to 400 mM, pH 3.5, with 26 mM LLC resulted in an increase in absolute % F to approximately 22%. Additional mechanistic studies described in Example 1 demonstrated the synergism of the two functional excipients, as well as the importance of formulation pH in enabling oral % F of tigecycline.

EXAMPLE 2

Administration of Zanamavir in Rats

Materials
Animals

Naïve, female Sprague-Dawley rats (Taconic Farms, Germantown, N.Y.) were housed in groups of two with food and water available ad libitum. Animals were approximately 250 g at the time of testing. Rats were fasted overnight (with water available), prior to dosing.

Test Articles and Reference Substances

Information on the test article, zanamivir, is listed in Table 12.

TABLE 12

Test Article Information

| Item | Compound Name | Supplier | Lot Number |
|---|---|---|---|
| Test Article | zanamivir | MedChem Express | CS-0631-05684 |

Vehicle

A stock solution of zanamivir was prepared by dissolving zanamivir in 2 N HCl to a concentration of 40 mg/mL immediately before use. Aliquots of this stock solution were diluted into the indicated formulations.

METHODS

Formulation Preparation and Dosing

Rats (n=3) were dosed by IV via an in-dwelling catheter to the carotid artery with a volume of 400 µL at a dose of 0.16 mg zanamivir. Blood samples were collected from the carotid artery prior to dosing and at 5, 10, 20, 30, and 60 min post-administration of the test article.

Rats (n=3 per formulation) were dosed via ID injection, 5 cm from the pyloric junction, with a bolus of 300 µL of each formulation (1.2 mg zanamivir). Blood samples were collected from the carotid artery prior to dosing and at 10, 20, 30, 60, 120, and up to 180 min post-administration of the test article.

All blood samples were treated with 20 µL of 180 mM EDTA and then centrifuged at 3000 rpm for 5 min. The plasma was collected, stored frozen at −20° C., and then shipped to Absorption Systems on dry ice for analysis.

TABLE 13

Formulations of Zanamivir

| Components | IV[1] | PBS[1] | A[2] | B[2] | C[2] | D[2] |
|---|---|---|---|---|---|---|
| zanamivir (mg/mL)[3] | 0.4 | 4.0 | 4.0 | 4.0 | 4.0 | 4.0 |
| Capmul MCM (% v/v) | 0 | 0 | 70 | 0 | 0 | 0 |
| propylene glycol (% v/v) | 0 | 0 | 20 | 0 | 0 | 0 |
| buffered citrate (mM), pH 3.5[4] | 0 | 0 | 0 | 100 | 400 | 0 |
| LLC (% w/v)[5] | 0 | 0 | 0 | 1.0 | 1.0 | 1.0 |

[1]Solvent is phosphate buffered saline
[2]Solvent is deionized water
[3]Diluted from a stock solution of 40 mg/mL zanamivir in 2N HCl
[4]Diluted from a 2M citric acid stock solution, pH 3.5
[5]Diluted from a 20% w/v stock solution of LLC in water Animal Procedures for Zanamivir Plasma Concentrations Plasma samples were analyzed by Absorption Systems using a qualified LC-MS/MS assay to determine the plasma concentrations of zanamivir.

Calculation of Bioavailability

The AUC of the plasma zanamivir concentration vs. time curves was calculated using trapezoidal integration in Microsoft Excel. Absolute bioavailability was calculated according to the equation below:

$$\% \ F_{(0-1)h} = \frac{AUC^{ID}_{(0-1\ h)}}{AUC^{IV}_{(0-1\ h)}} \times \frac{D^{IV}}{D^{ID}} \times 100$$

where $D^{ID}$ is the ID dose (mg) divided by the weight (kg) of each individual rat, while $D^{IV}$ is the IV dose (mg) divided by the mean body weight (kg) of the rats in the IV arm.

Results

Figure 27:
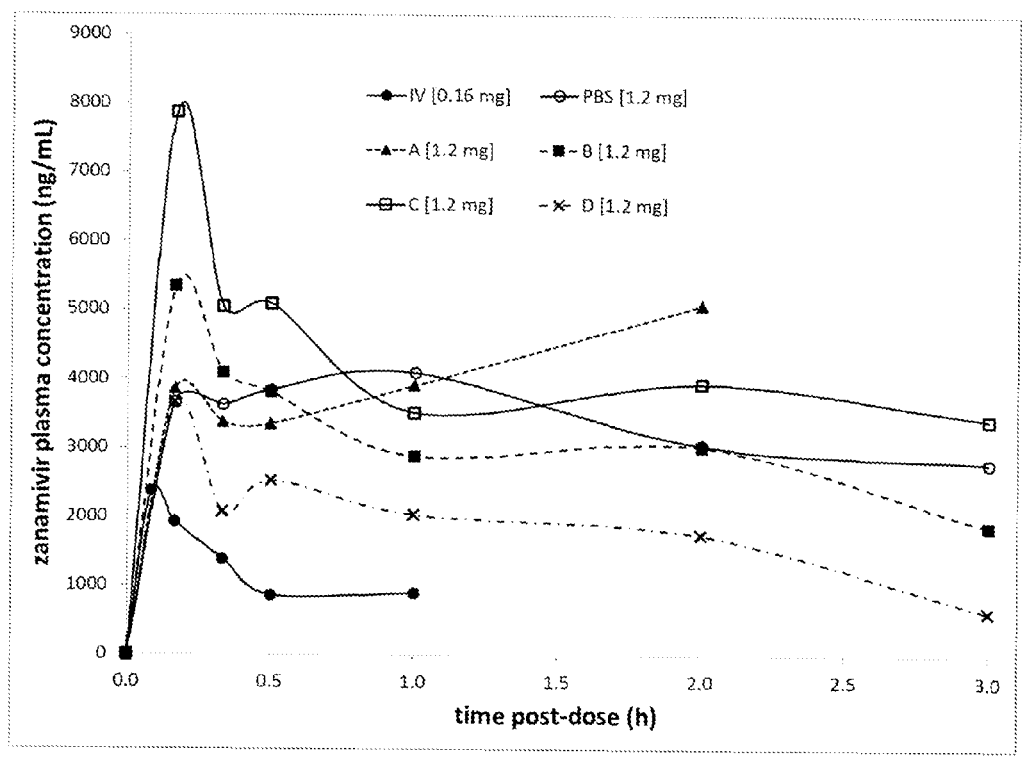
FIG. 27 is a graph showing Mean PK Profiles for Formulations of Zanamivir at the Indicated Dose.

Individual plasma concentrations of zanamivir for the six formulations investigated are listed below. The mean PK profiles are shown in FIG. 27 and the PK data for each formulation are summarized in Table 14.

TABLE 14

Summary of PK Data by Formulation

| | Formulation | | | | | |
|---|---|---|---|---|---|---|
| | IV | PBS | A | B | C | D |
| $AUC_{(0-1\ h)}$ (ng * h/mL), Mean Value (% CV) | 1183 (27.0) | 3297 (27.2) | 3518 (28.6) | 3559 (75.6) | 4726 (29.8) | 2302 (27.2) |
| % $F_{(0-1\ h)}$, Mean Values (% CV) | NA | 41.6 (28.4) | 35.7 (25.0) | 41.2 (70.3) | 57.9 (22.6) | 27.3 (26.6) |

Because the stock solution of zanamivir was prepared in 2 N HCl in order to solubilize the API, all of the vehicles were acidic. This resulted in enhanced absorption of zanamivir for all the formulations. However, relative to each other, the vehicle with the best bioavailability was formulation "C", containing 400 mM CA and 1.0% LLC.

TABLE 15

Plasma Concentrations (ng/mL) of Zanamivir: IV Formulation Study RA885

| | Animal # (weight, kg) | | | | |
|---|---|---|---|---|---|
| Time-point (mM) | 1 (0.213) | 2 (0.225) | 3 (0.223) | Mean | SD |
| 0 | 0 | 0 | 0 | 0 | 0 |
| 5 | 2120 | 2650 | 2350 | 2373 | 266 |
| 10 | 1950 | 2260 | 1570 | 1927 | 346 |
| 20 | 1240 | 1660 | 1250 | 1383 | 240 |
| 30 | 327 | 1450 | 821 | 866 | 563 |
| 60 | 877 | 1140 | 681 | 899 | 230 |

TABLE 16

Plasma Concentrations (ng/mL) of Zanamivir: Formulation A Study RA885

| | Animal # (weight, kg) | | | | |
|---|---|---|---|---|---|
| Time-point (min) | 4 (0.205) | 5 (0.218) | 6 (0.214) | Mean | SD |
| 0 | 0 | 0 | 0 | 0 | 0 |
| 10 | 5150 | 3140 | 3290 | 3860 | 1120 |
| 20 | 3660 | 3340 | 3090 | 3363 | 286 |
| 30 | 4350 | 3510 | 2190 | 3350 | 1089 |
| 60 | 5050 | 4280 | 2390 | 3907 | 1369 |
| 120 | NS | 6360 | 3800 | 5080 | NA |

TABLE 17

Plasma Concentrations (ng/mL) of Zanamivir: Formulation PBS Study RA886

| Time-point (min) | Animal # (weight, kg) | | | Mean | SD |
|---|---|---|---|---|---|
| | 1 (0.242) | 2 (0.220) | 3 (0.233) | | |
| 0 | 0 | 0 | 0 | 0 | 0 |
| 10 | 3840 | 3960 | 3200 | 3667 | 409 |
| 20 | 3930 | 4380 | 2560 | 3623 | 948 |
| 30 | 4440 | 4670 | 2410 | 3840 | 1244 |
| 60 | 5090 | 4810 | 2380 | 4093 | 1490 |
| 120 | 3480 | 3840 | 1810 | 3043 | 1083 |
| 180 | 3130 | NS | 2450 | 2790 | NA |

TABLE 18

Plasma Concentrations (ng/mL) of Zanamivir: Formulation B Study RA886

| Time-point (min) | Animal # (weight, kg) | | | Mean | SD |
|---|---|---|---|---|---|
| | 4 (0.237) | 5 (0.241) | 6 (0.219) | | |
| 0 | 0 | 0 | 0 | 0 | 0 |
| 10 | 1560 | 4260 | 10200 | 5340 | 4420 |
| 20 | 2540 | 1800 | 7920 | 4087 | 3340 |
| 30 | 3160 | 1050 | 7210 | 3807 | 3131 |
| 60 | 2580 | 1200 | 4860 | 2880 | 1848 |
| 120 | 1780 | 1820 | 5460 | 3020 | 2113 |
| 180 | 2180 | 1560 | NS | 1870 | NA |

TABLE 19

Plasma Concentrations (ng/mL) of Zanamivir: Formulation C Study RA886

| Time-point (min) | Animal # (weight, kg) | | | Mean | SD |
|---|---|---|---|---|---|
| | 7 (0.223) | 8 (0.250) | 9 (0.255) | | |
| 0 | 0 | 0 | 0 | 0 | 0 |
| 10 | 12700 | 4690 | 6190 | 7860 | 4258 |
| 20 | 5970 | 4500 | 4650 | 5040 | 809 |
| 30 | 6470 | 3940 | 4880 | 5097 | 1279 |
| 60 | 4150 | 3020 | 3370 | 3513 | 578 |
| 120 | 6660 | 2250 | 2890 | 3933 | 2383 |
| 180 | NS | 3420 | NS | 3420 | NA |

TABLE 20

Plasma Concentrations (ng/mL) of Zanamivir: Formulation D Study RA886

| Time-point (mM) | Animal # (weight, kg) | | | Mean | SD |
|---|---|---|---|---|---|
| | 10 (0.233) | 11 (0.231) | 12 (0.233) | | |
| 0 | 0 | 0 | 0 | 0 | 0 |
| 10 | 3720 | 3600 | 3650 | 3657 | 60.3 |
| 20 | 1650 | 2690 | 1860 | 2067 | 550 |
| 30 | 2190 | 3360 | 2020 | 2523 | 730 |
| 60 | 1030 | 3410 | 1650 | 2030 | 1235 |
| 120 | 898 | 3760 | 561 | 1740 | 1758 |
| 180 | 625 | NS | NS | 625 | NA |

TABLE 21

Summary of Example 2 Formulations Tested

| Components | Formulation | | | | | |
|---|---|---|---|---|---|---|
| | I.V.[1] | PBS[1] | A[2] | B[2] | C[2] | D[2] |
| zanamivir (mg/mL)[3] | 0.4 | 4.0 | 4.0 | 4.0 | 4.0 | 4.0 |
| Capmul MCM (% v/v) | 0 | 0 | 70 | 0 | 0 | 0 |
| propylene glycol (% v/v) | 0 | 0 | 20 | 0 | 0 | 0 |
| buffered citrate (mM), pH 3.5[4] | 0 | 0 | 0 | 100 | 400 | 0 |
| LLC (% w/v)[5] | 0 | 0 | 0 | 1.0 | 1.0 | 1.0 |

[1]Solvent is phosphate buffered saline
[2]Solvent is deionized water
[3]Diluted from a stock solution of 40 mg/mL zanamivir in 2N HCl
[4]Diluted from a 2M citric acid stock solution, pH 3.5
[5]Diluted from a 20% w/v stock solution of LLC in water Each of the five ID formulations was administered as a bolus injection directly into the duodenum of rats at a dose of 1.2 mg (4.8 mg/kg), while the IV formulation was injected via an in-dwelling catheter to the carotid artery at a dose of 0.16 mg (0.64 mg/kg). Blood samples were collected from the carotid artery prior to dosing and at predetermined time-points post-dosing to determine plasma concentrations of zanamivir by an LC-MS/MS assay.

TABLE 22

Summary of Bioavailability by Formulation
% $F_{(0-1\ h)}$, Mean Values (% CV)

| PBS | A | B | C | D |
|---|---|---|---|---|
| 41.6 (28.4) | 35.7 (25.0) | 41.2 (70.3) | 57.9 (22.6) | 27.3 (26.6) |

Because the stock solution of zanamivir was prepared in 2 N HCl in order to solubilize the API, all of the vehicles were acidified. This resulted in an enhancement of absorption of zanamivir for all the formulations. However, relative to each other, the vehicle with the best bioavailability was formulation "C", containing 400 mM CA and 1.0% LLC.

EXAMPLE 3

Aminoglycoside Administration in Dogs

Materials
Animals

Adult Beagle dogs weighing approximately 10 to 15 kg were used in the study. The animals were housed at Sinclair Research Center, Columbia, Mo. either individually or in pairs in over-sized dog runs. Primary enclosures were as specified in the USDA Animal Welfare Act (9 CFR Parts 1, 2 and 3) and as described in the Guide for the Care and Use of Laboratory Animals (National Academy Press, Washington, D.C., 1996). A 12-hour light/12-hour dark photoperiod was maintained. Room temperature was set to be maintained at 20±5° C. Relative humidity was monitored but not controlled. Animal room and pen cleaning were performed according to the testing facility (Sinclair) SOPs.

TEKLAD® Certified Canine Diet was provided once daily in amounts (~400 grams) appropriate for the size and age of the animals. Tap water was available ad libitum via automatic watering device or water bowls.

Animals were fasted overnight prior to drug administration and throughout the blood collection period.

TABLE 23

Test Article Information

| Test Item | Batch/Lot Number | Supplier |
|---|---|---|
| Kanamycin | 5023 | Spectrum, Amresco |
| Tobramycin | 110M1191V | Sigma Aldrich |

Vehicle

For the IV study, kanamycin and tobramycin were prepared as concentrated solutions in PBS and shipped frozen to Sinclair Research Center where it was diluted in PBS and filter sterilized prior to administration. For oral studies, kanamycin and tobramycin were blended with other excipients and transferred to capsules.

Methods

Doses and Route of Administration

An IV dose of kanamycin was administered as a bolus injection into each of three Beagle dogs at a dose of 0.1 mg/mL. An IV dose of tobramycin was administered as a bolus injection into each of three Beagle dogs at a dose of 0.1 mg/mL. Details of formulation composition and dosing are summarized in Table 24.

TABLE 24

IV Formulation and Dose

| Formulation | Test Article | Study No. | Dose Concentration (mg/mL) | Dose Volume (mL) | No. of Dogs |
|---|---|---|---|---|---|
| JSV-003-040 | Kanamycin | SC434 | 0.1 | 1.0 | 3 |
| JSV-003-044 | Tobramycin | SC435 | 0.1 | 1.0 | 3 |

Oral dosing of capsules was accomplished by administering the capsules to the back of each dog's mouth. Kanamycin was delivered in either DRCAPS™ or VCAP PLUS™ capsules, both from Capsugel. The DRCAPS™ offer acid resistant properties and do not require coating. The VCAP PLUS™ capsules are vegetarian HPMC capsules. Details of formulation composition and dosing for kanamycin capsules are summarized in Table 25.

TABLE 25

Kanamycin Capsule Composition, Coating and Number of Dogs

| Formulation | Study No. | Kanamycin (mg) | CA (mg) | LLC (mg) | PROSOLV™ (mg) | Capsule Type | Coated[1] | No. of Dogs |
|---|---|---|---|---|---|---|---|---|
| JSV-003-010 | SC426 | 10 | 500 | 100 | 67 | DRCAPS™ | no | 4 |
| JSV-003-041 | SC433 | 10 | 250 | 100 | 240 | DRCAPS™ | no | 5 |
| JSV-003-005 | SC426 | 10 | 500 | 100 | 67 | VCAP PLUS™ | yes | 4 |
| JSV-003-038 | SC432 | 10 | 0 | 0 | 525 | VCAP PLUS™ | no | 6 |
| JSV-003-039 | SC432 | 10 | 500 | 100 | 67 | VCAP PLUS™ | no | 6 |
| JSV-003-052 | SC438 | 10 | 250 | 100 | 247 | VCAP PLUS™ | yes | 3 |
| JSV-003-053 | SC438 | 10 | 100 | 100 | 361 | VCAP PLUS™ | yes | 3 |
| JSV-003-054 | SC438 | 10 | 50 | 100 | 393 | VCAP PLUS™ | yes | 3 |

[1]To 6% weight gain with Eudragit 7 L30-D55.

Tobramycin was delivered in enteric-coated VCAP PLUS™ capsules and the details of formulation composition and dosing are summarized in Table 26.

TABLE 26

Tobramycin Capsule Composition, Coating and Number of Dogs

| Formulation | Study No. | Tobramycin (mg) | CA (mg) | LLC (mg) | PROSOLV™ (mg) | Capsule Type | Coated[1] | No. of Dogs |
|---|---|---|---|---|---|---|---|---|
| JSV-003-050 | SC436 | 10 | 0 | 0 | 525 | VCAP PLUS™ | yes | 8 |
| JSV-003-051 | SC436 | 10 | 500 | 100 | 67 | VCAP PLUS™ | yes | 8 |

[1]To 6% weight gain with Eudragit 7 L30-D55.

Study Design and Plasma Sample Collection

Adult female Beagle dogs, weighing 9-15 kg were used in the oral and IV studies. Dogs were fasted overnight before the beginning of each study but were allowed free access to water. On the day of the study, one pre-dose blood sample of 3 mL was collected from each animal. Subsequently, each group of animals was given a single capsule containing either kanamycin or tobramycin blended in a specified formulation.

After administration of the drug, 3 mL blood samples were collected from the brachial vein at various time-points up to 240 minutes (4 hours) post-administration. Blood samples were collected into new heparinized monovette sampling syringes. The samples were placed on ice before being centrifuged for 10 minutes at approximately 2750 rpm at 2-8° C. Each tube was labeled with the dog ID # and time-point, and they were stored at −20° C. pending shipment.

Analytical Procedure for Kanamycin and Tobramycin

Plasma kanamycin and tobramycin concentrations were determined with a competitive ELISA kit from UC Biodevices (Fremont, Calif.) according to "ELISA for Detection of Kanamycin". For determination of kanamycin blood levels, the kit kanamycin standards were used for the standard curve. For determination of tobramycin blood levels, tobramycin from Sigma-Aldrich was diluted and used for the standard curve. The standard curve range for kanamycin was 0.2 ng/mL to 3.0 ng/mL. The standard curve range for tobramycin was 0.1 ng/mL to 5.0 ng/mL. Plasma samples were diluted appropriately with the kit assay buffer.

Kanamycin and Tobramycin ELISA Calculations

Mean plasma concentrations of kanamycin and tobramycin were calculated using a 5-parameter curve fit in SOFT-MAX™ Pro software, Version 5.0.1 (Molecular Devices).

Pharmacokinetic Data Handling

Kanamycin and tobramycin concentration-time data for each animal were analyzed by non-compartmental methods using PK functions for Microsoft Excel. The maximum plasma concentration ($C_{max}$) values and their times of occurrence ($T_{max}$) were obtained directly from the plasma concentration vs. time profiles. The areas under the plasma concentration-time curves ($AUC_{last}$) were estimated by the linear trapezoidal rule from time zero to the time of the last observed plasma concentration.

Results

Figure 28:
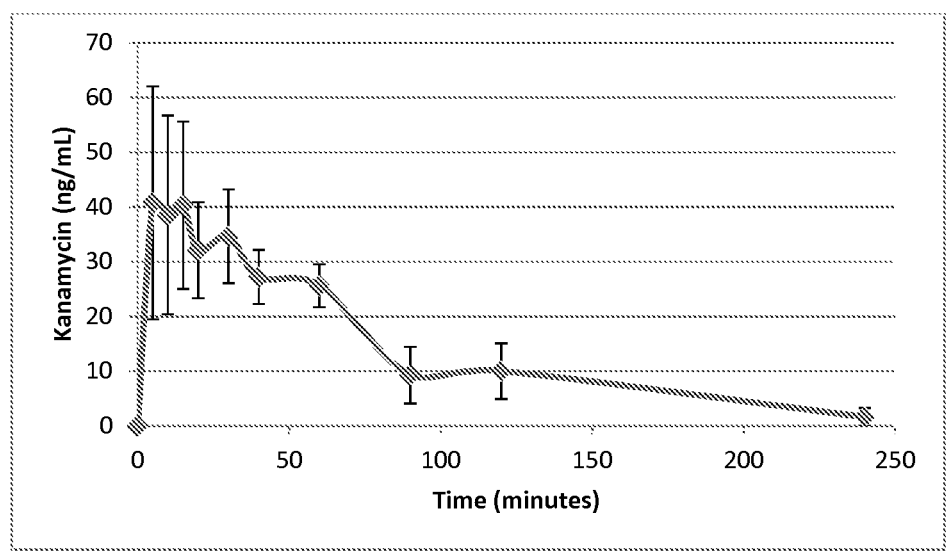
FIG. 28 is a graph showing Mean Concentration (±SEM) Profiles vs Time Following Bolus IV Injection of Kanamycin.
Figure 29:
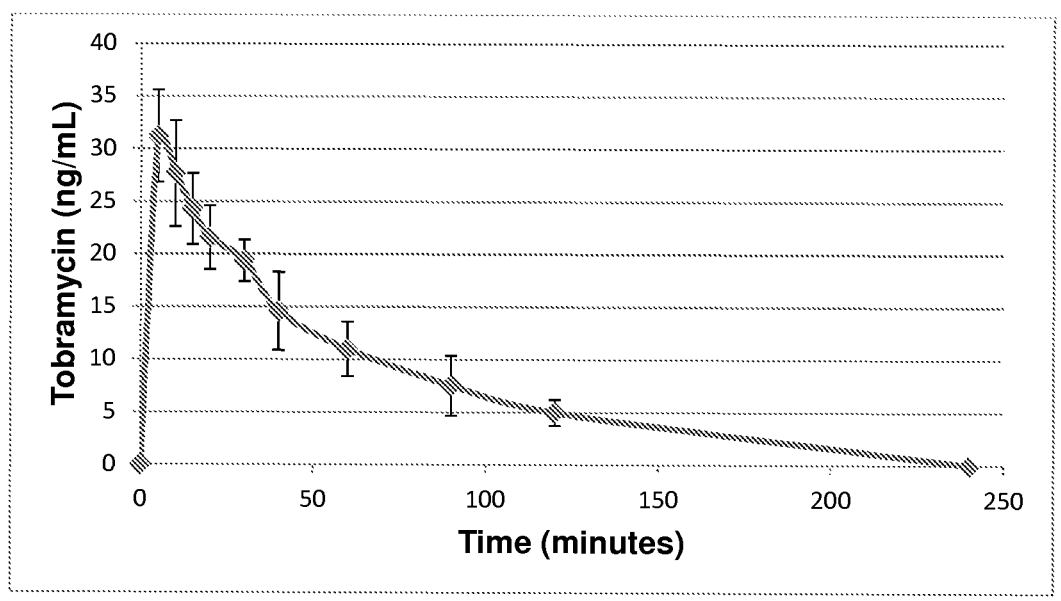
FIG. 29 is a graph showing Mean Concentration (±SEM) Profiles vs Time Following Bolus IV Injection of Tobramycin.

Individual plasma concentration of kanamycin and tobramycin at each sampling time, as well as the corresponding PK parameter, are presented in Table 27 through Table 38. Mean concentration time profiles for kanamycin and tobramycin after IV administration is shown in FIG. 28 and FIG. 29, respectively.

Plasma Kanamycin Following IV Administration

The $C_{max}$ for plasma kanamycin following IV administration (SC434) was 50 ng/mL and was observed at a mean time ($T_{max}$) of 5 minutes (Table 27). The mean concentration profiles for kanamycin after IV administration are shown in FIG. 28.

TABLE 27

Plasma Concentrations and Pharmacokinetics of Kanamycin in Beagle Dogs Following a Single Dose IV Bolus Injection

| | Dog Number | | | | | |
|---|---|---|---|---|---|---|
| | 5296 | 5297 | 5298 | Mean | SD | % CV |
| | Kanamycin Plasma Concentration (ng/mL) | | | | | |
| Time (min) | | | | | | |
| 0 | 0 | 0 | 0 | 0 | 0 | NA |
| 5 | 77.73 | 40.56 | 3.97 | 40.75 | 36.88 | 91 |
| 10 | 70.40 | 37.75 | 7.52 | 38.56 | 31.45 | 82 |
| 15 | 56.24 | 54.88 | 9.70 | 40.27 | 26.49 | 66 |
| 20 | 39.87 | 41.85 | 14.59 | 32.10 | 15.20 | 47 |
| 30 | 43.81 | 42.52 | 17.48 | 34.60 | 14.84 | 43 |
| 40 | 29.91 | 34.08 | 17.58 | 27.19 | 8.58 | 32 |
| 60 | 30.96 | 27.79 | 18.01 | 25.59 | 6.75 | 26 |
| 90 | 0 | 9.81 | 17.91 | 9.24 | 8.97 | 97 |
| 120 | 0 | 13.36 | 16.63 | 10.00 | 8.81 | 88 |
| 240 | 0 | 0 | 4.84 | 1.61 | 2.79 | 173 |
| Parameters | | | | | | |
| Dose (mg) | 0.10 | 0.10 | 0.10 | 0.10 | | |
| $C_{max}$ (ng/mL) | 77.73 | 54.88 | 18.01 | 50.21 | 30.13 | 60 |
| $T_{max}$ (min) | 5 | 15 | 60 | 27 | 29 | 110 |
| AUC (min * ng/mL) | 2787 | 3806 | 3169 | 3254 | 514 | 16 |

Plasma Tobramycin Following IV Administration

The $C_{max}$ for plasma tobramycin following IV administration (SC435) was 31 ng/mL and observed at a mean $T_{max}$ of 5 minutes (Table 28). The mean concentration profiles for tobramycin after IV administration are shown in FIG. 29.

TABLE 28

Plasma Concentrations and Pharmacokinetics of Tobramycin in Beagle Dogs Following a Single Dose IV Bolus Injection

| | Dog Number | | | | | |
|---|---|---|---|---|---|---|
| | 5299 | 5300 | 5301 | Mean | SD | % CV |
| | Tobramycin Plasma Concentration (ng/mL) | | | | | |
| Time (min) | | | | | | |
| 0 | 0 | 0 | 0 | 0 | 0 | NA |
| 5 | 38.41 | 31.97 | 23.29 | 31.22 | 7.59 | 24 |
| 10 | 34.59 | 30.47 | 17.89 | 27.65 | 8.70 | 31 |
| 15 | 29.03 | 26.11 | 17.74 | 24.29 | 5.86 | 24 |
| 20 | 23.21 | 25.78 | 15.71 | 21.57 | 5.23 | 24 |
| 30 | 20.31 | 22.23 | 15.58 | 19.37 | 3.42 | 18 |
| 40 | 15.89 | 20.25 | 7.60 | 14.58 | 6.43 | 44 |
| 60 | 11.01 | 15.45 | 6.52 | 10.99 | 4.47 | 41 |
| 90 | 5.83 | 13.10 | 3.72 | 7.55 | 4.92 | 65 |
| 120 | 6.09 | 6.26 | 2.49 | 4.95 | 2.13 | 43 |
| 240 | 0 | 0 | 0 | 0 | 0 | NA |
| Parameters | | | | | | |
| Dose (mg) | 0.10 | 0.10 | 0.10 | 0.10 | | |
| $C_{max}$ (ng/mL) | 38.41 | 31.97 | 23.29 | 31.22 | 7.59 | 24 |
| $T_{max}$ (min) | 5 | 5 | 5 | 5 | 0 | 0 |
| AUC (min * ng/mL) | 1937 | 2331 | 1085 | 1784 | 637 | 36 |

Plasma Kanamycin Following Oral Administration

Figure 30:
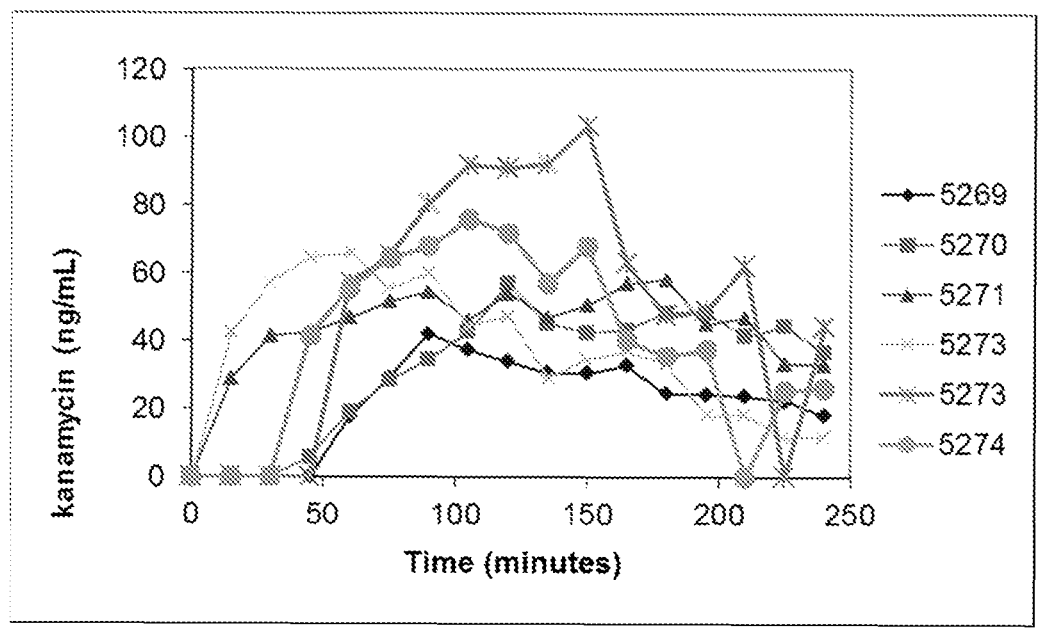
FIG. 30 is a graph showing Individual Plasma Kanamycin Absorption Profiles for Dogs Following a Single Oral Dose in PROSOLV™ of Uncoated Capsules (Formulation JSV-003-038).

The results for orally administered kanamycin in unformulated, uncoated VCAP PLUS™ capsules (SC432) containing only PROSOLV™ (formulation JSV-003-038) are shown in Table 29. All dogs showed low levels of bioavailability with a mean of 2.8%. Individual dog profiles are shown in FIG. 30.

TABLE 29

Plasma Concentrations and Pharmacokinetics of Kanamycin in Beagle Dogs Following a Single Oral Dose in PROSOLV ™ of Uncoated Capsules (Formulation JSV-003-038)

| Time (min) | 5269 | 5270 | 5271 | 5272 | 5273 | 5274 | Mean | SD |
|---|---|---|---|---|---|---|---|---|
| | \multicolumn{6}{c}{Plasma Concentration of Kanamycin (ng/mL)} | | |
| 0 | 0 | 0 | 0 | 0 | 0 | 0 | 0 | 0 |
| 15 | 0 | 0 | 28.85 | 42.19 | 0 | 0 | 11.84 | 18.82 |
| 30 | 0 | 0 | 41.29 | 57.37 | 0 | 0 | 16.44 | 25.98 |
| 45 | 0 | 5.77 | 42.43 | 64.79 | 0 | 41.75 | 25.79 | 27.51 |
| 60 | 17.71 | 19.14 | 46.83 | 66.07 | 57.00 | 55.55 | 43.72 | 20.52 |
| 75 | 29.24 | 28.29 | 51.73 | 55.37 | 65.10 | 64.52 | 49.04 | 16.54 |
| 90 | 42.04 | 34.59 | 54.47 | 60.16 | 80.59 | 67.86 | 56.62 | 16.83 |
| 105 | 37.34 | 42.76 | 46.18 | 44.25 | 91.84 | 76.02 | 56.40 | 22.10 |
| 120 | 34.01 | 57.00 | 54.10 | 47.26 | 90.94 | 71.81 | 59.19 | 19.87 |
| 135 | 30.61 | 45.13 | 46.91 | 28.84 | 92.20 | 57.10 | 50.13 | 23.19 |
| 150 | 30.62 | 42.34 | 50.50 | 34.72 | 103.40 | 67.80 | 54.90 | 27.18 |
| 165 | 32.82 | 43.09 | 56.87 | 37.01 | 62.95 | 40.27 | 45.50 | 11.83 |
| 180 | 24.49 | 48.42 | 58.35 | 33.32 | 47.60 | 35.45 | 41.27 | 12.34 |
| 195 | 24.40 | 48.39 | 44.96 | 18.11 | 49.01 | 37.34 | 37.04 | 13.06 |
| 210 | 23.75 | 41.52 | 46.94 | 18.29 | 62.18 | 0.00 | 32.11 | 22.38 |
| 225 | 22.39 | 44.58 | 33.32 | 11.69 | 0.00 | 25.20 | 22.86 | 15.71 |
| 240 | 18.14 | 36.62 | 32.92 | 12.25 | 44.40 | 26.29 | 28.44 | 11.95 |
| Parameters | | | | | | | | |
| $C_{max}$ (ng/mL) | 42.04 | 57.00 | 58.35 | 66.07 | 103.40 | 76.02 | 67.15 | 21.00 |
| $T_{max}$ (min) | 90 | 120 | 180 | 60 | 150 | 105 | 118 | 43 |
| AUC (min * ng/mL) | 5377 | 7790 | 10586 | 9067 | 12375 | 9807 | 9167 | 2408 |
| F (%) | 1.7 | 2.4 | 3.3 | 2.8 | 3.8 | 3.0 | 2.8 | 0.7 |

Figure 31:
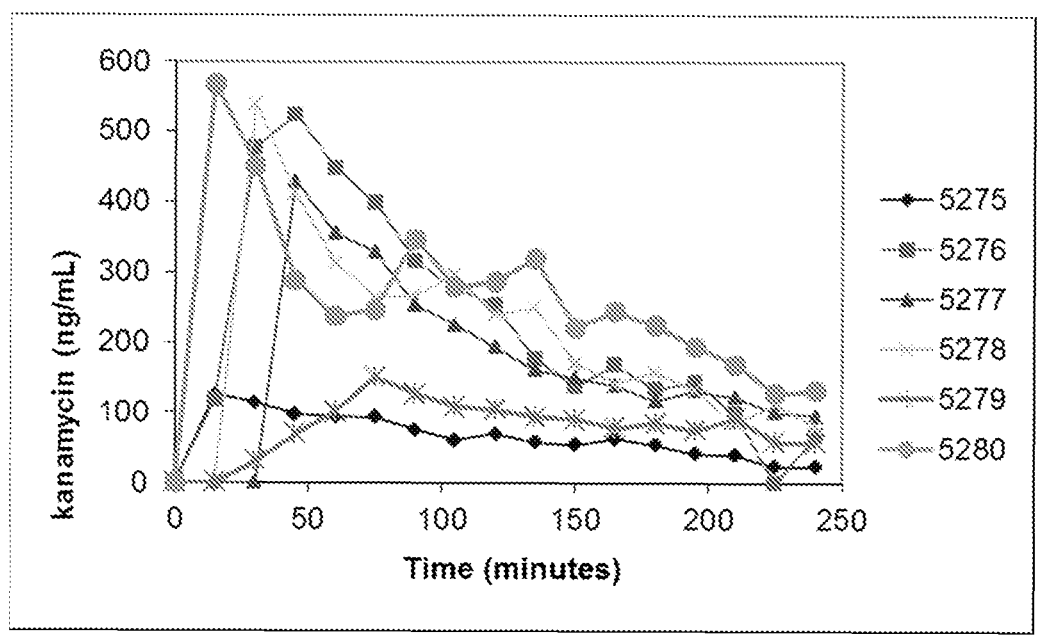
FIG. 31 is a graph showing Individual Plasma Kanamycin Absorption Profiles for Dogs Following a Single Oral Dose in Uncoated Capsules Formulated with CA and LLC (Formulation JSV-003-039).

The addition of CA and LLC to the uncoated capsules resulted in a significantly higher mean bioavailability of 12.4% (SC432). The individual dog results are shown in Table 30 Individual dog profiles are shown in FIG. 31.

TABLE 30

Plasma Concentrations and Pharmacokinetics of Kanamycin in Beagle Dogs Following a Single Oral Dose in Uncoated Capsules Formulated with CA and LLC (Formulation JSV-003-039)

| Time (min) | 5275 | 5276 | 5277 | 5278 | 5279 | 5280 | Mean | SD |
|---|---|---|---|---|---|---|---|---|
| | \multicolumn{6}{c}{Plasma Concentration of Kanamycin (ng/mL)} | | |
| 0 | 0 | 0 | 0 | 0 | 0 | 0 | 0 | 0 |
| 15 | 125.18 | 117.18 | 0 | 0 | 0 | 568.01 | 135.06 | 220.27 |
| 30 | 113.44 | 476.63 | 0 | 540.77 | 30.91 | 451.15 | 268.82 | 246.33 |
| 45 | 97.42 | 524.01 | 429.31 | 411.43 | 69.50 | 288.62 | 303.38 | 186.31 |
| 60 | 93.91 | 448.02 | 355.26 | 314.58 | 100.89 | 236.67 | 258.22 | 142.01 |
| 75 | 93.17 | 398.77 | 328.84 | 263.23 | 149.84 | 246.59 | 246.74 | 112.34 |
| 90 | 75.41 | 315.50 | 253.03 | 267.73 | 126.44 | 347.77 | 230.98 | 107.47 |
| 105 | 60.57 | 276.76 | 225.11 | 295.92 | 107.98 | 278.55 | 207.48 | 99.46 |
| 120 | 70.25 | 254.06 | 192.94 | 240.75 | 103.69 | 287.13 | 191.47 | 87.06 |
| 135 | 58.47 | 175.69 | 160.35 | 250.12 | 93.71 | 319.33 | 176.28 | 96.82 |
| 150 | 54.76 | 137.56 | 149.16 | 170.54 | 90.54 | 221.72 | 137.38 | 58.94 |
| 165 | 62.69 | 167.66 | 138.70 | 141.50 | 78.66 | 243.87 | 138.85 | 65.25 |
| 180 | 54.56 | 133.03 | 116.16 | 157.23 | 84.22 | 224.03 | 128.21 | 59.25 |
| 195 | 41.53 | 142.78 | 131.61 | 131.22 | 74.51 | 193.81 | 119.24 | 53.76 |
| 210 | 39.51 | 98.54 | 122.41 | 84.51 | 92.27 | 168.90 | 101.02 | 42.90 |
| 225 | 23.88 | 0 | 99.89 | 112.16 | 58.57 | 127.65 | 70.36 | 51.29 |
| 240 | 23.53 | 67.00 | 96.00 | 79.73 | 56.86 | 131.24 | 75.73 | 36.51 |
| Parameters | | | | | | | | |
| $C_{max}$ (ng/mL) | 125.18 | 524.01 | 429.31 | 540.77 | 149.84 | 568.01 | 389.52 | 200.86 |
| $T_{max}$ (min) | 15 | 45 | 45 | 30 | 75 | 15 | 38 | 23 |

TABLE 30-continued

Plasma Concentrations and Pharmacokinetics of Kanamycin in Beagle Dogs Following a Single Oral Dose in Uncoated Capsules Formulated with CA and LLC (Formulation JSV-003-039)

| | Dog Number | | | | | | | |
|---|---|---|---|---|---|---|---|---|
| | 5275 | 5276 | 5277 | 5278 | 5279 | 5280 | Mean | SD |
| | Plasma Concentration of Kanamycin (ng/mL) | | | | | | | |
| AUC (min * ng/mL) | 15209 | 54617 | 41262 | 51323 | 19352 | 59781 | 40257 | 18843 |
| F (%) | 4.7 | 16.8 | 12.7 | 15.8 | 5.9 | 18.4 | 12.4 | 5.8 |

Figure 32:
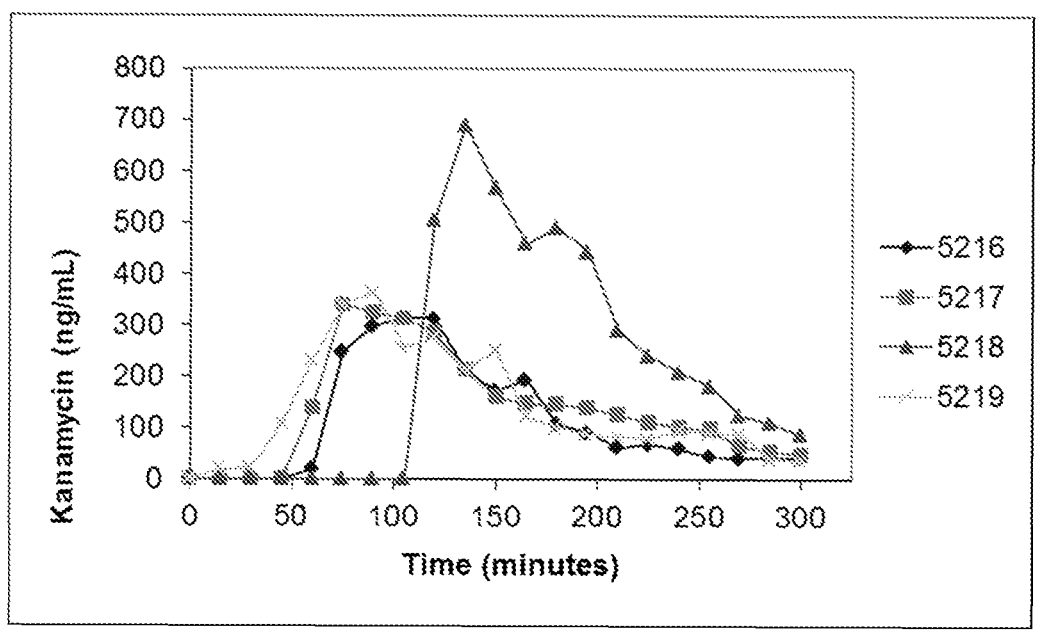
FIG. 32 is a graph showing Individual Plasma Profiles for Dogs Following a Single Oral Dose of Capsules Containing 500 mg CA (Formulation JSV-003-005).

Enteric-coated VCAP PLUS™ capsules containing 100 mg LLC were prepared with varying concentrations of CA to test the effect of CA content on the bioavailability of kanamycin. Formulation JSV-003-005 (SC426) contained 500 mg of CA and gave a mean bioavailability of 14.2%. The individual dog plasma results are shown in Table 31 and the individual dog absorption profiles are shown in FIG. 32.

TABLE 31

Plasma Concentrations and Pharmacokinetics of Kanamycin in Beagle Dogs Following a Single Oral Dose of Capsules Containing 500 mg CA (Formulation JSV-003-005)

| | Dog Number | | | | | |
|---|---|---|---|---|---|---|
| | 5216 | 5217 | 5218 | 5219 | Mean | SD |
| | Plasma Concentration of Kanamycin (ng/mL) | | | | | |
| Time (min) | | | | | | |
| 0 | 0 | 0 | 0 | 0 | 0 | |
| 15 | 0 | 0 | 0 | 20.24 | 5.06 | 10.12 |
| 30 | 0 | 0 | 0 | 22.52 | 5.63 | 11.26 |
| 45 | 0 | 0 | 0 | 107.91 | 26.98 | 53.96 |
| 60 | 20.40 | 138.68 | 0 | 229.76 | 97.21 | 107.45 |
| 75 | 248.33 | 340.76 | 0 | 341.61 | 232.68 | 161.17 |
| 90 | 298.03 | 324.25 | 0 | 365.94 | 247.06 | 167.06 |
| 105 | 314.82 | 312.88 | 0 | 255.86 | 220.89 | 149.78 |
| 120 | 313.20 | 284.70 | 504.25 | 274.29 | 344.11 | 108.02 |
| 135 | 213.70 | 213.15 | 689.95 | 212.17 | 332.24 | 238.47 |
| 150 | 172.90 | 159.47 | 566.06 | 250.95 | 287.35 | 190.14 |
| 165 | 193.60 | 147.50 | 458.86 | 121.18 | 230.28 | 155.29 |
| 180 | 107.90 | 145.20 | 490.18 | 101.57 | 211.21 | 186.97 |
| 195 | 90.58 | 139.00 | 442.56 | 87.48 | 189.91 | 170.08 |
| 210 | 61.89 | 124.80 | 289.09 | 84.07 | 139.96 | 102.78 |
| 225 | 69.09 | 111.70 | 241.48 | 78.41 | 125.17 | 79.67 |
| 240 | 59.82 | 100.70 | 208.15 | 94.21 | 115.72 | 64.18 |
| 255 | 45.01 | 97.00 | 180.94 | 91.60 | 103.64 | 56.57 |
| 270 | 41.85 | 65.50 | 123.28 | 88.77 | 79.85 | 34.72 |
| 285 | 44.64 | 55.50 | 109.43 | 38.75 | 62.08 | 32.32 |
| 300 | 42.27 | 49.00 | 86.88 | 34.67 | 53.21 | 23.20 |
| Parameters | | | | | | |
| $C_{max}$ (ng/mL) | 314.82 | 340.76 | 689.95 | 365.94 | 427.87 | 175.96 |
| $T_{max}$ (min) | 105 | 75 | 135 | 90 | 101 | 26 |
| AUC (min * ng/mL) | 34753 | 41779 | 65215 | 43118 | 46216 | 13186 |
| F (%) | 10.7 | 12.8 | 20.0 | 13.3 | 14.2 | 4.1 |

Figure 33:
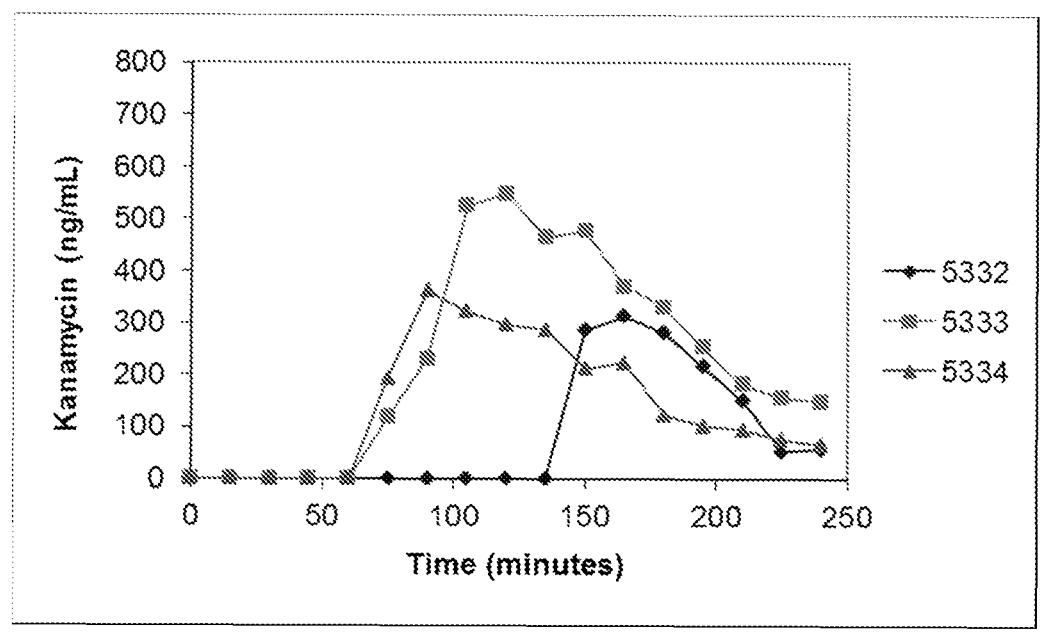
FIG. 33 is a graph showing Individual Plasma Profiles for Dogs Following a Single Oral Dose of Capsules Containing 250 mg CA (Formulation JSV-003-052).

Formulation JSV-003-052 (SC438) contained 250 mg of CA and gave a mean bioavailability of 11.4%. The individual dog plasma results are shown in Table 32 and the individual dog absorption profiles are shown in FIG. 33.

TABLE 32

Plasma Concentrations and Pharmacokinetics of Kanamycin in Beagle Dogs Following a Single Oral Dose of Capsules Containing 250 mg CA (Formulation JSV-003-052)

| | Dog Number | | | | |
|---|---|---|---|---|---|
| | 5332 | 5333 | 5334 | Mean | |
| | Plasma Concentration of Kanamycin (ng/mL) | | | | SD |
| Time (min) | | | | | |
| 0 | 0 | 0 | 0 | 0 | |
| 15 | 0 | 0 | 0 | 0 | |
| 30 | 0 | 0 | 0 | 0 | |
| 45 | 0 | 0 | 0 | 0 | |
| 60 | 0 | 0 | 0 | 0 | |
| 75 | 0 | 117.92 | 193.31 | 103.74 | 97.43 |
| 90 | 0 | 230.56 | 362.97 | 197.84 | 183.68 |
| 105 | 0 | 525.55 | 323.03 | 282.86 | 265.07 |
| 120 | 0 | 548.56 | 296.40 | 281.65 | 274.58 |
| 135 | 0 | 466.00 | 287.00 | 251.00 | 235.08 |
| 150 | 285.66 | 477.72 | 212.42 | 325.27 | 137.01 |
| 165 | 312.68 | 371.57 | 223.29 | 302.51 | 74.66 |
| 180 | 281.71 | 331.32 | 121.99 | 245.01 | 109.39 |
| 195 | 217.49 | 254.00 | 102.52 | 191.34 | 79.05 |
| 210 | 150.35 | 182.29 | 95.36 | 142.67 | 43.97 |
| 225 | 53.33 | 155.56 | 76.96 | 95.28 | 53.52 |
| 240 | 58.18 | 148.76 | 66.18 | 91.04 | 50.15 |
| Parameters | | | | | |
| $C_{max}$ (ng/mL) | 312.68 | 548.56 | 362.97 | 408.07 | 124.24 |
| $T_{max}$ (min) | 165 | 120 | 90 | 125 | 38 |
| AUC (min * ng/mL) | 19955 | 56031 | 34925 | 36970 | 18125 |
| F (%) | 6.1 | 17.2 | 10.7 | 11.4 | 5.6 |

Figure 34:
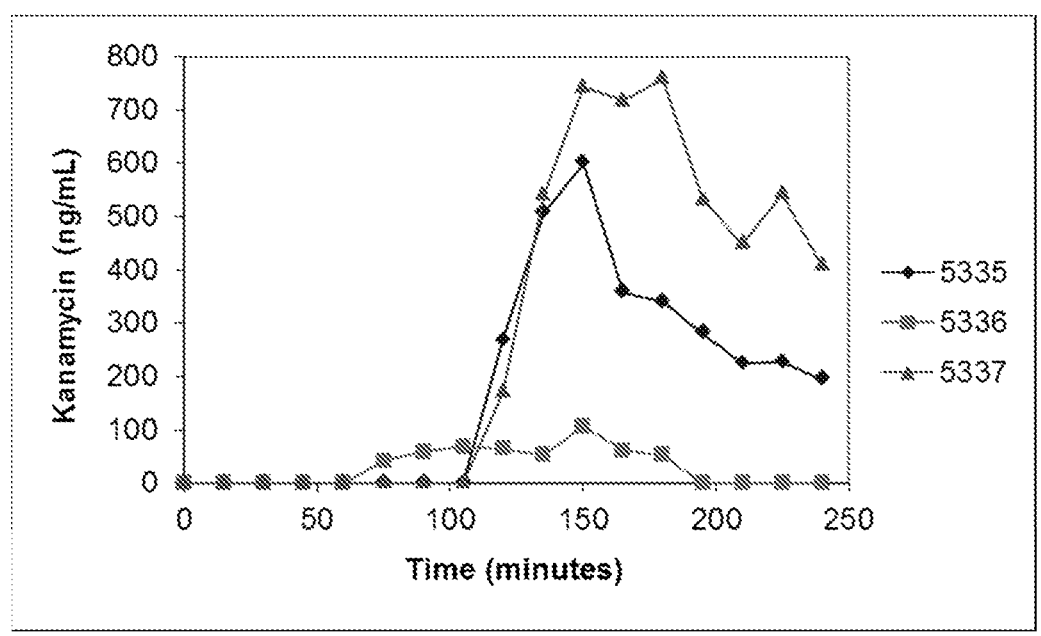
FIG. 34 is a graph showing Individual Plasma Profiles for Dogs Following a Single Oral Dose of Capsules Containing 100 mg CA (Formulation JSV-003-053).

Formulation JSV-003-053 (SC438) contained 100 mg of CA and gave a mean bioavailability of 12.4%. The individual dog plasma results are shown in Table 33 and the individual absorption profiles are shown in FIG. 34.

TABLE 33

Plasma Concentrations and Pharmacokinetics of Kanamycin in Beagle Dogs Following a Single Oral Dose of Capsules Containing 100 mg CA (Formulation JSV-003-053)

| | Dog Number | | | | |
|---|---|---|---|---|---|
| | 5335 | 5336 | 5337 | Mean | |
| | Plasma Concentration of Kanamycin (ng/mL) | | | | SD |
| Time (min) | | | | | |
| 0 | 0 | 0 | 0 | 0 | |
| 15 | 0 | 0 | 0 | 0 | |
| 30 | 0 | 0 | 0 | 0 | |
| 45 | 0 | 0 | 0 | 0 | |
| 60 | 0 | 0 | 0 | 0 | |
| 75 | 0 | 42.07 | 0 | 14.02 | 24.29 |
| 90 | 0 | 58.50 | 0 | 19.50 | 33.77 |
| 105 | 0 | 68.20 | 0 | 22.73 | 39.38 |
| 120 | 267.56 | 64.99 | 170.59 | 167.71 | 101.32 |
| 135 | 506.08 | 53.04 | 539.93 | 366.35 | 271.86 |
| 150 | 600.77 | 106.61 | 743.62 | 483.67 | 334.26 |
| 165 | 357.58 | 61.39 | 716.79 | 378.59 | 328.20 |
| 180 | 340.01 | 53.18 | 759.07 | 384.09 | 355.00 |
| 195 | 280.92 | 0.00 | 531.86 | 270.93 | 266.07 |
| 210 | 224.47 | 0.00 | 448.64 | 224.37 | 224.32 |
| 225 | 227.25 | 0.00 | 542.74 | 256.66 | 272.56 |
| 240 | 194.29 | 0.00 | 408.40 | 200.90 | 204.28 |

TABLE 33-continued

Plasma Concentrations and Pharmacokinetics of Kanamycin in Beagle Dogs Following a Single Oral Dose of Capsules Containing 100 mg CA (Formulation JSV-003-053)

| | Dog Number | | | | |
|---|---|---|---|---|---|
| | 5335 | 5336 | 5337 | Mean | |
| | Plasma Concentration of Kanamycin (ng/mL) | | | | SD |
| Parameters | | | | | |
| $C_{max}$ (ng/mL) | 600.77 | 106.61 | 759.07 | 488.82 | 340.33 |
| $T_{max}$ (min) | 150 | 150 | 180 | 160 | 17 |
| AUC (min * ng/mL) | 43527 | 7620 | 69862 | 40336 | 31243 |
| F (%) | 13.4 | 2.3 | 21.5 | 12.4 | 9.6 |

Figure 35:
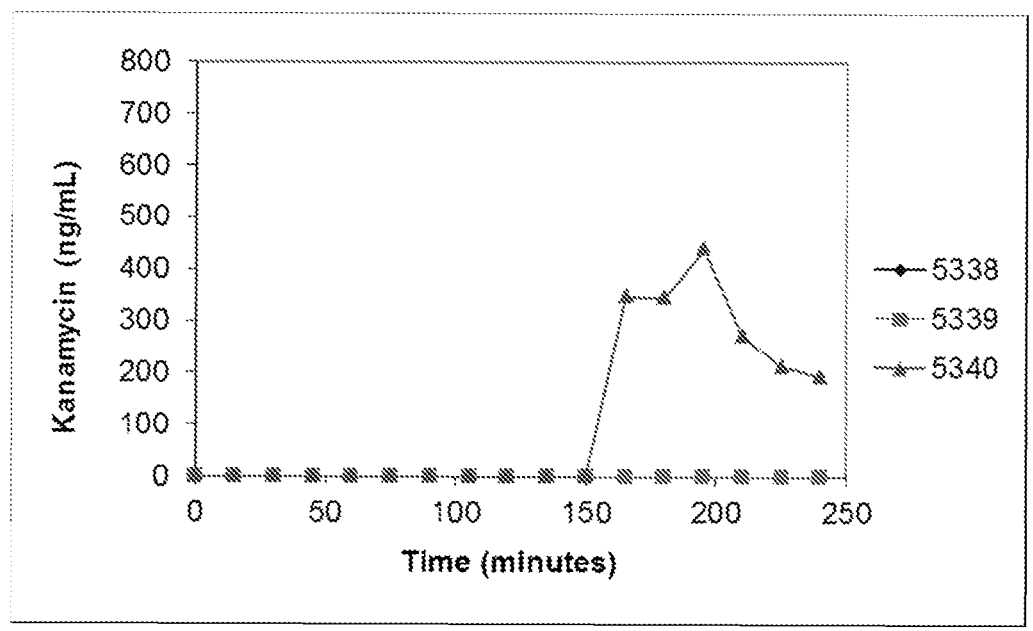
FIG. 35 is a graph showing Individual Plasma Profiles for Dogs Following a Single Oral Dose of Capsules Containing 50 mg CA (Formulation JSV-003-054).

Formulation JSV-003-054 (SC438) contained 50 mg of CA. Only one out of three dogs dosed showed detectable blood levels for kanamycin with a mean bioavailability of 2.6%. The individual dog plasma results are shown in Table 34 and individual plasma absorption profiles are shown in FIG. 35.

TABLE 34

Plasma Concentrations and Pharmacokinetics of Kanamycin in Beagle Dogs Following a Single Oral Dose of Capsules Containing 50 mg CA (Formulation JSV-003-054)

| | Dog Number | | | | |
|---|---|---|---|---|---|
| | 5338 | 5339 | 5340 | Mean | |
| | Plasma Concentration of Kanamycin (ng/mL) | | | | SD |
| Time (min) | | | | | |
| 0 | 0 | 0 | 0 | 0 | |
| 15 | 0 | 0 | 0 | 0 | |
| 30 | 0 | 0 | 0 | 0 | |
| 45 | 0 | 0 | 0 | 0 | |
| 60 | 0 | 0 | 0 | 0 | |
| 75 | 0 | 0 | 0 | 0 | |
| 90 | 0 | 0 | 0 | 0 | |
| 105 | 0 | 0 | 0 | 0 | |
| 120 | 0 | 0 | 0 | 0 | |
| 135 | 0 | 0 | 0 | 0 | |
| 150 | 0 | 0 | 0 | 0 | |
| 165 | 0 | 0 | 347.67 | 115.89 | 200.73 |
| 180 | 0 | 0 | 344.80 | 114.93 | 199.07 |
| 195 | 0 | 0 | 440.51 | 146.84 | 254.33 |
| 210 | 0 | 0 | 271.48 | 90.49 | 156.74 |
| 225 | 0 | 0 | 213.69 | 71.23 | 123.37 |
| 240 | 0 | 0 | 193.05 | 64.35 | 111.46 |
| Parameters | | | | | |
| $C_{max}$ (ng/mL) | 0 | 0 | 440.51 | 146.84 | 254.33 |
| $T_{max}$ (min) | NA | NA | 195 | 195 | |
| AUC (min * ng/mL) | 0 | 0 | 25720 | 8573 | 14850 |
| F (%) | 0 | 0 | 7.9 | 2.6 | 4.6 |

Figure 36:
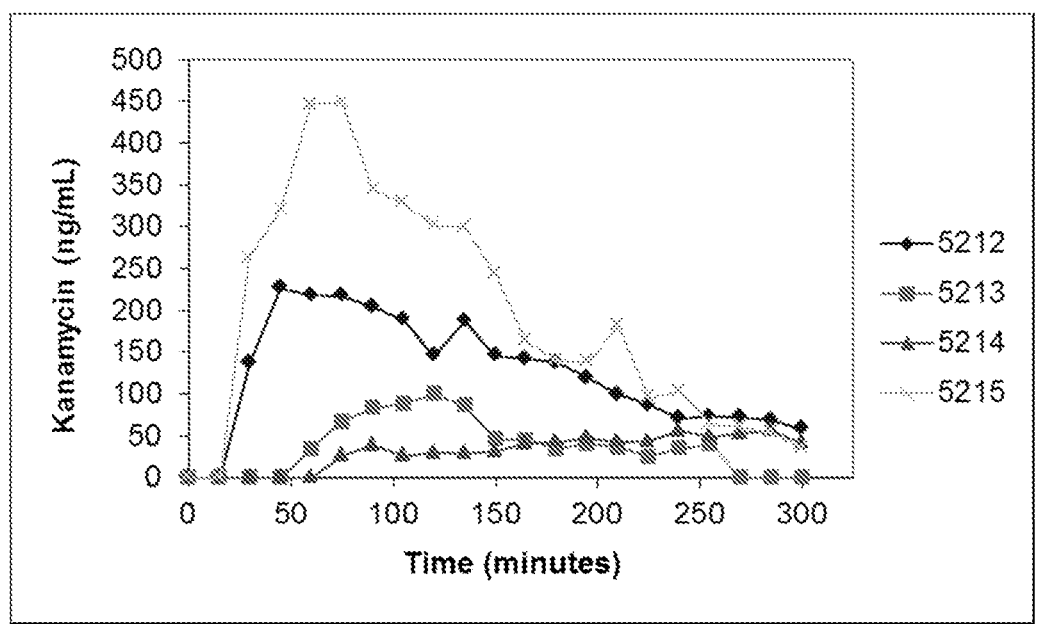
FIG. 36 is a graph showing Individual Plasma Profiles for Dogs Following a Single Oral Dose of Capsules Containing 500 mg CA in DRCAPS™ (Formulation JSV-003-010).

The use of DRCAPS™ instead of enteric-coated VCAP PLUS™ on the bioavailability of kanamycin was investigated. Two studies were undertaken with DRCAPS™, SC426 and SC433, respectively. In the first study (formulation JSV-003-010) DRCAPS™ contained 500 mg of CA and 100 mg LLC. The mean bioavailability was 9.2% and the individual plasma kanamycin concentrations are shown in Table 35. The individual plasma absorption profiles are shown in FIG. 36.

TABLE 35

Plasma Concentrations and Pharmacokinetics of Kanamycin in Beagle Dogs Following a Single Oral Dose of Capsules Containing 500 mg CA and 100 mg LLC in DRCAPS ™ (Formulation JSV-003-010)

| | Dog Number | | | | | |
|---|---|---|---|---|---|---|
| | 5212 | 5213 | 5214 | 5215 | Mean | SD |
| | Plasma Concentration of Kanamycin (ng/mL) | | | | | |
| Time (min) | | | | | | |
| 0 | 0 | 0 | 0 | 0 | 0 | |
| 15 | 0 | 0 | 0 | 0 | 0 | |
| 30 | 136.50 | 0 | 0 | 264.04 | 100.14 | 126.81 |
| 45 | 227.00 | 0 | 0 | 319.54 | 136.64 | 162.23 |
| 60 | 218.50 | 34.64 | 0 | 446.62 | 174.94 | 204.94 |
| 75 | 217.80 | 66.31 | 26.46 | 449.11 | 189.92 | 191.45 |
| 90 | 204.20 | 83.07 | 39.36 | 343.42 | 167.51 | 136.43 |
| 105 | 188.20 | 88.13 | 25.87 | 327.70 | 157.48 | 131.72 |
| 120 | 145.76 | 99.26 | 29.69 | 302.01 | 144.18 | 115.53 |
| 135 | 186.50 | 85.78 | 29.11 | 299.80 | 150.30 | 119.04 |
| 150 | 145.60 | 45.72 | 31.26 | 243.24 | 116.46 | 98.63 |
| 165 | 141.70 | 44.99 | 40.41 | 162.11 | 97.30 | 63.63 |
| 180 | 136.90 | 34.39 | 42.75 | 140.19 | 88.56 | 57.84 |
| 195 | 118.80 | 40.46 | 47.90 | 137.69 | 86.21 | 49.24 |
| 210 | 98.60 | 36.03 | 42.57 | 180.66 | 89.47 | 66.97 |
| 225 | 86.60 | 25.30 | 43.66 | 94.69 | 62.56 | 33.45 |
| 240 | 70.40 | 35.39 | 56.18 | 103.46 | 66.36 | 28.61 |
| 255 | 73.00 | 40.14 | 49.18 | 63.42 | 56.44 | 14.62 |
| 270 | 71.80 | 0.00 | 52.77 | 60.42 | 46.25 | 31.81 |
| 285 | 68.20 | 0.00 | 56.41 | 53.28 | 44.47 | 30.34 |
| 300 | 58.30 | 0.00 | 41.10 | 34.64 | 33.51 | 24.47 |
| Parameters | | | | | | |
| $C_{max}$ (ng/mL) | 227.00 | 99.26 | 56.41 | 449.11 | 208 | 176 |
| $T_{max}$ (min) | 45 | 120 | 285 | 75 | 131 | 107 |
| AUC (min * ng/mL) | 38478 | 11394 | 9512 | 60131 | 29879 | 24122 |
| F (%) | 11.8 | 3.5 | 2.9 | 18.5 | 9.2 | 7.4 |

Figure 37:
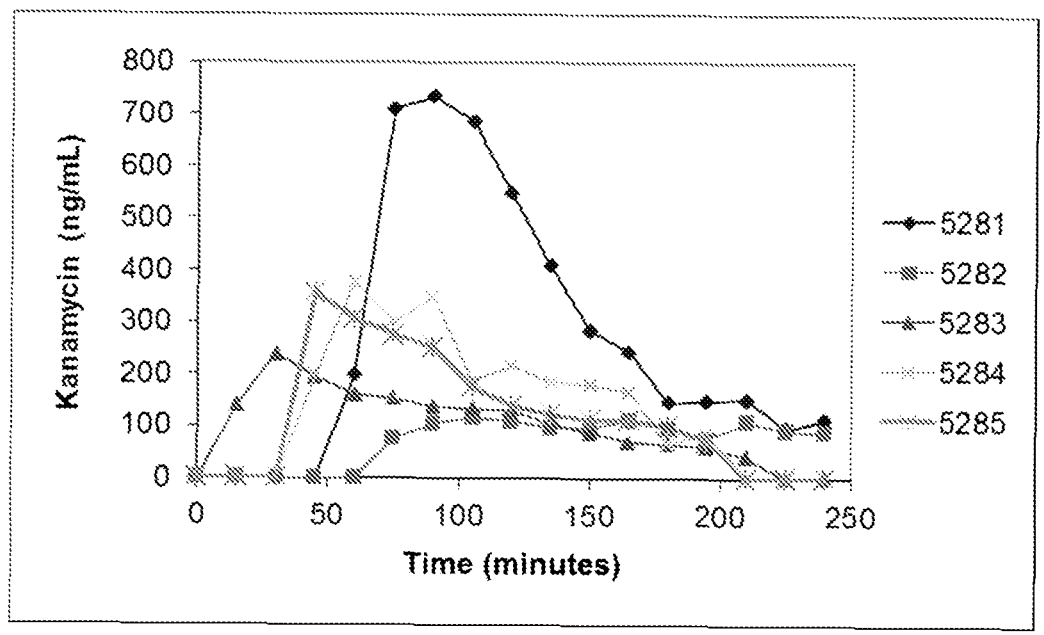
FIG. 37 is a graph showing Individual Plasma Profiles for Dogs Following a Single Oral Dose of Capsules Containing 250 mg CA in DRCAPS™ (Formulation JSV-003-041).

The second study with DRCAPS™ (formulation JSV-003-041) contained 250 mg of CA and 100 mg LLC. The mean bioavailability was 10.6% and the individual plasma kanamycin concentrations are shown in Table 36. The individual plasma absorption profiles are shown in FIG. 37.

TABLE 36

Plasma Concentrations and Pharmacokinetics of Kanamycin in Beagle Dogs Following a Single Oral Dose of Capsules Containing 250 mg CA and 100 mg LLC in DRCAPS ™ (Formulation JSV-003-041)

| | Dog Number | | | | | | |
|---|---|---|---|---|---|---|---|
| | 5281 | 5282 | 5283 | 5284 | 5285 | Mean | SD |
| | Plasma Concentration of Kanamycin (ng/mL) | | | | | | |
| Time (min) | | | | | | | |
| 0 | 0 | 0 | 0 | 0 | 0 | 0 | |
| 15 | 0 | 0 | 138.40 | 0 | 0 | 27.68 | 61.89 |
| 30 | 0 | 0 | 238.54 | 0 | 0 | 47.71 | 106.68 |
| 45 | 0 | 0 | 194.13 | 199.20 | 355.77 | 149.82 | 151.42 |
| 60 | 197.89 | 0 | 159.40 | 374.52 | 306.43 | 207.65 | 144.17 |
| 75 | 711.54 | 76.02 | 152.98 | 299.22 | 274.63 | 302.88 | 245.84 |
| 90 | 735.06 | 105.37 | 137.31 | 348.87 | 251.22 | 315.57 | 253.57 |
| 105 | 686.58 | 115.45 | 133.58 | 186.53 | 175.35 | 259.50 | 240.53 |
| 120 | 547.75 | 109.89 | 130.51 | 217.06 | 139.54 | 228.95 | 182.78 |
| 135 | 408.86 | 97.42 | 105.46 | 183.32 | 123.33 | 183.68 | 130.30 |
| 150 | 285.29 | 97.00 | 88.12 | 181.08 | 113.70 | 153.04 | 82.43 |
| 165 | 242.83 | 110.48 | 70.80 | 165.34 | 111.31 | 140.15 | 66.52 |
| 180 | 145.29 | 97.16 | 66.58 | 66.68 | 102.74 | 95.69 | 32.41 |
| 195 | 149.45 | 77.36 | 59.94 | 87.04 | 70.94 | 88.95 | 35.23 |
| 210 | 151.28 | 108.38 | 41.67 | 0.00 | 0.00 | 60.27 | 67.47 |
| 225 | 95.78 | 92.33 | 0.00 | 0.00 | 0.00 | 37.62 | 51.53 |
| 240 | 113.14 | 88.44 | 0.00 | 0.00 | 0.00 | 40.32 | 55.89 |

TABLE 36-continued

Plasma Concentrations and Pharmacokinetics of Kanamycin in Beagle Dogs Following a Single Oral Dose of Capsules Containing 250 mg CA and 100 mg LLC in DRCAPS ™ (Formulation JSV-003-041)

| | Dog Number | | | | | | |
|---|---|---|---|---|---|---|---|
| | 5281 | 5282 | 5283 | 5284 | 5285 | Mean | |
| | Plasma Concentration of Kanamycin (ng/mL) | | | | | | SD |
| Parameters | | | | | | | |
| $C_{max}$ (ng/mL) | 735.06 | 115.45 | 238.54 | 374.52 | 355.77 | 363.87 | 232.05 |
| $T_{max}$ (min) | 90 | 105 | 30 | 60 | 45 | 66 | 31 |
| AUC (min * ng/mL) | 66213 | 16966 | 24723 | 34633 | 30374 | 34582 | 18879 |
| F (%) | 20.3 | 5.2 | 7.6 | 10.6 | 9.3 | 10.6 | 5.8 |

Plasma Tobramycin Following Oral Administration

Figure 38:
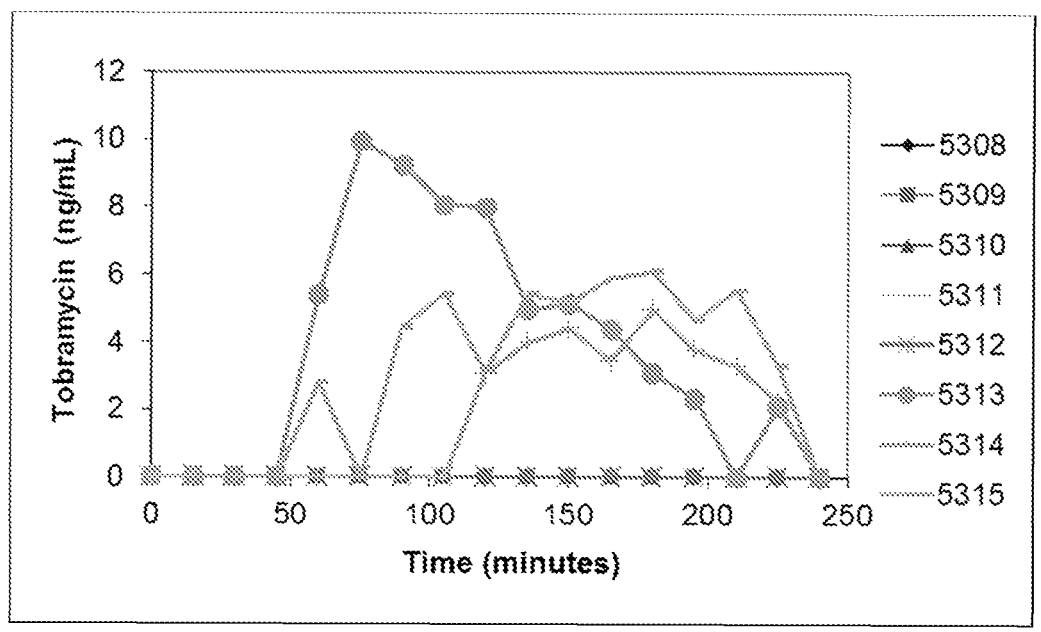
FIG. 38 is a graph showing Individual Plasma Profiles for Beagle Dogs Following a Single Oral Dose in PROSOLV™ (Formulation JSV-003-050).

The results for orally administered tobramycin in unformulated, VCAP PLUS™ capsules containing only PROSOLV™ (formulation JSV-003-050) are shown in Table 37. The mean bioavailability was 0.2%; only three out of eight dogs showed detectable blood levels of tobramycin. Individual plasma profiles are shown in FIG. 38.

Figure 39:
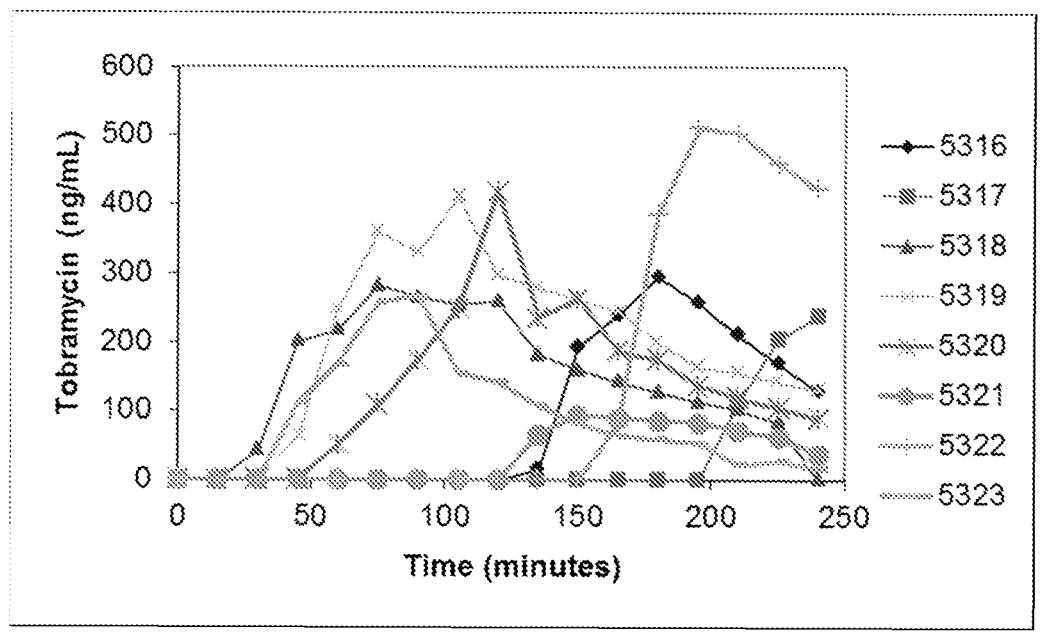
FIG. 39 is a graph showing Individual Plasma Profiles for Beagle Dogs Following a Single Oral Dose with CA and LLC (Formulation JSV-003-051).

With the addition of CA and LLC, the mean bioavailability for the 8 dogs increased to 15%. All dogs given formulation JSV-003-051 showed blood levels of tobramycin. The PK results are shown in Table 38 and the individual plasma profiles are shown in FIG. 39.

TABLE 37

Plasma Concentrations and Pharmacokinetics of Tobramycin in Beagle Dogs Following a Single Oral Dose in PROSOLV ™ (Formulation JSV-003-050)

| | Dog Number | | | | | | | | | |
|---|---|---|---|---|---|---|---|---|---|---|
| | 5308 | 5309 | 5310 | 5311 | 5312 | 5313 | 5314 | 5315 | Mean | |
| | Plasma Concentration of Kanamycin (ng/mL) | | | | | | | | | SD |
| Time (min) | | | | | | | | | | |
| 0 | 0 | 0 | 0 | 0 | 0 | 0 | 0 | 0 | 0 | |
| 15 | 0 | 0 | 0 | 0 | 0 | 0 | 0 | 0 | 0 | |
| 30 | 0 | 0 | 0 | 0 | 0 | 0 | 0 | 0 | 0 | |
| 45 | 0 | 0 | 0 | 0 | 0 | 0 | 0 | 0 | 0 | |
| 60 | 0 | 0 | 0 | 0 | 0 | 5.41 | 0 | 2.81 | 1.03 | 2.03 |
| 75 | 0 | 0 | 0 | 0 | 0 | 9.94 | 0 | 0.00 | 1.24 | 3.51 |
| 90 | 0 | 0 | 0 | 0 | 0 | 9.24 | 0 | 4.45 | 1.71 | 3.42 |
| 105 | 0 | 0 | 0 | 0 | 0 | 8.07 | 0 | 5.45 | 1.69 | 3.21 |
| 120 | 0 | 0 | 0 | 0 | 0 | 7.99 | 3.05 | 3.12 | 1.77 | 2.87 |
| 135 | 0 | 0 | 0 | 0 | 0 | 4.97 | 3.99 | 5.42 | 1.80 | 2.51 |
| 150 | 0 | 0 | 0 | 0 | 0 | 5.14 | 4.40 | 5.21 | 1.84 | 2.56 |
| 165 | 0 | 0 | 0 | 0 | 0 | 4.39 | 3.43 | 5.92 | 1.72 | 2.46 |
| 180 | 0 | 0 | 0 | 0 | 0 | 3.08 | 4.98 | 6.12 | 1.77 | 2.58 |
| 195 | 0 | 0 | 0 | 0 | 0 | 2.33 | 3.75 | 4.65 | 1.34 | 1.95 |
| 210 | 0 | 0 | 0 | 0 | 0 | 0 | 3.31 | 5.57 | 1.11 | 2.14 |
| 225 | 0 | 0 | 0 | 0 | 0 | 2.10 | 2.22 | 3.31 | 0.95 | 1.36 |
| 240 | 0 | 0 | 0 | 0 | 0 | 0 | 0 | 0 | 0 | |
| Parameters | | | | | | | | | | |
| $C_{max}$ (ng/mL) | 0 | 0 | 0 | 0 | 0 | 9.94 | 4.98 | 6.12 | 2.63 | 3.89 |
| $T_{max}$ (min) | NA | NA | NA | NA | NA | 75 | 180 | 180 | 145 | 61 |
| AUC (min * ng/mL) | 0 | 0 | 0 | 0 | 0 | 940 | 437 | 780 | 270 | 397 |
| F (%) | 0.0 | 0.0 | 0.0 | 0.0 | 0.0 | 0.5 | 0.2 | 0.4 | 0.2 | 0.2 |

TABLE 38

Plasma Concentrations and Pharmacokinetics of Tobramycin in Beagle Dogs Following a Single Oral Dose with CA and LLC (Formulation JSV-003-051)

| | Dog Number | | | | | | | | | |
|---|---|---|---|---|---|---|---|---|---|---|
| | 5316 | 5317 | 5318 | 5319 | 5320 | 5321 | 5322 | 5323 | Mean | SD |
| | Plasma Concentration of Tobramycin (ng/mL) | | | | | | | | | |
| Time (min) | | | | | | | | | | |
| 0 | 0 | 0 | 0 | 0 | 0 | 0 | 0 | 0 | 0 | |
| 15 | 0 | 0 | 0 | 0 | 0 | 0 | 0 | 0 | 0 | |
| 30 | 0 | 0 | 42.66 | 0 | 0 | 0 | 0 | 0 | 5.33 | 15.08 |
| 45 | 0 | 0 | 200.28 | 60.76 | 0 | 0 | 0 | 111.78 | 46.60 | 74.57 |
| 60 | 0 | 0 | 217.26 | 247.28 | 50.93 | 0 | 0 | 168.53 | 85.50 | 107.48 |
| 75 | 0 | 0 | 281.13 | 360.49 | 109.20 | 0 | 0 | 258.73 | 126.19 | 151.40 |
| 90 | 0 | 0 | 264.55 | 328.17 | 174.06 | 0 | 0 | 266.34 | 129.14 | 144.17 |
| 105 | 0 | 0 | 253.75 | 411.29 | 248.33 | 0 | 0 | 155.24 | 133.58 | 158.82 |
| 120 | 0 | 0 | 259.62 | 296.63 | 419.60 | 0 | 0 | 142.60 | 139.81 | 167.09 |
| 135 | 14.99 | 0 | 180.86 | 277.83 | 235.47 | 65.64 | 0 | 108.01 | 110.35 | 109.63 |
| 150 | 192.55 | 0 | 158.89 | 0.00 | 263.00 | 94.04 | 0 | 81.19 | 98.71 | 99.27 |
| 165 | 238.77 | 0 | 143.39 | 244.02 | 187.52 | 90.04 | 81.32 | 64.12 | 131.15 | 87.44 |
| 180 | 294.34 | 0 | 126.93 | 200.20 | 175.01 | 86.65 | 384.60 | 59.47 | 165.90 | 126.62 |
| 195 | 256.81 | 0 | 112.71 | 163.21 | 136.25 | 82.81 | 511.32 | 52.72 | 164.48 | 159.69 |
| 210 | 209.64 | 112.49 | 101.78 | 155.59 | 118.59 | 71.71 | 503.29 | 22.30 | 161.92 | 148.53 |
| 225 | 169.12 | 204.40 | 83.39 | 142.60 | 104.87 | 62.34 | 459.58 | 27.90 | 156.78 | 135.18 |
| 240 | 129.03 | 237.67 | 0.00 | 129.69 | 89.35 | 38.33 | 423.36 | 16.42 | 132.98 | 140.12 |
| Parameters | | | | | | | | | | |
| Cmax (ng/mL) | 294.34 | 237.67 | 281.13 | 411.29 | 419.60 | 94.04 | 511.32 | 266.34 | 314.47 | 12 |
| Tmax (min) | 180 | 240 | 75 | 105 | 120 | 150 | 195 | 90 | 144 | 57 |
| AUC (min * ng/mL) | 21611 | 6536 | 36408 | 44294 | 34013 | 8586 | 32277 | 22907 | 25829 | 13402 |
| F (%) | 12.1 | 3.7 | 20.4 | 24.8 | 19.1 | 4.8 | 18.1 | 12.8 | 14.5 | 7.5 |

Mean Oral Absorption Profiles of Kanamycin

Figure 40:
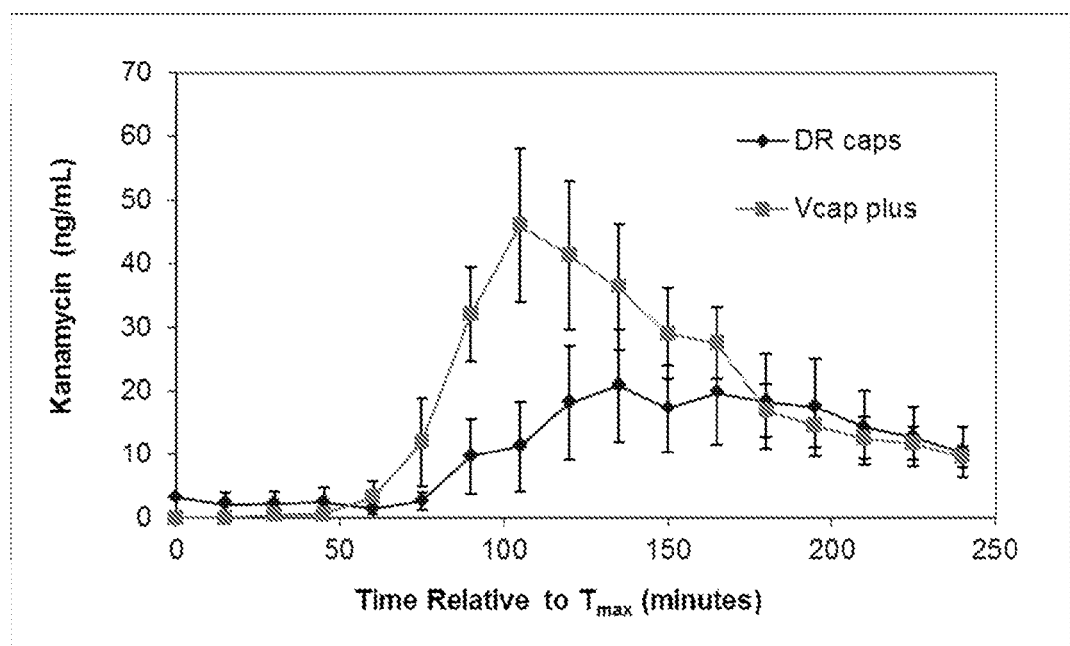
FIG. 40 is a graph showing Mean Absorption Profiles for Dogs Administered Kanamycin Formulated with 500 mg CA and 100 mg LLC in DRCAPS™ and Enteric-Coated VCAP PLUS™ Capsules.

A comparison for the mean absorption profiles for dogs administered kanamycin in DRCAPS™ (JSV-003-010) and VCAP PLUS™ (JSV-003-005) capsules are shown in FIG. 40. Both sets of capsules contained the same key excipients (500 mg CA and 100 mg LLC) and the only difference was the capsules themselves. The data for each set of capsules were adjusted for the mean $T_{max}$. The error bars represent the standard error of the mean (SEM).

Figure 41:
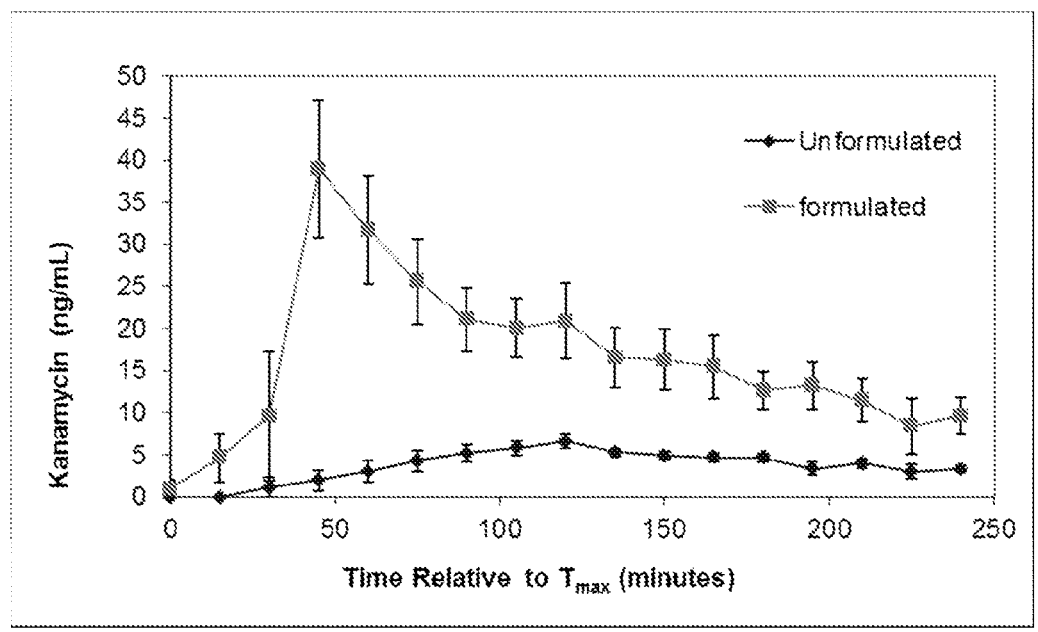
FIG. 41 is a graph showing Mean Absorption Profiles for Dogs Administered Kanamycin in Unformulated and Formulated with CA and LLC in Uncoated VCAP PLUS™ Capsules.

A comparison for the mean absorption profiles for dogs administered kanamycin in unformulated (0 mg CA and 0 mg LLC) VCAP PLUS™ (JSV-003-038) and formulated (500 mg CA and 100 mg LLC) VCAP PLUS (JSV-003-039) capsules are shown in FIG. 41. Both sets of capsules were uncoated. The data for each set of capsules were adjusted for the mean T.. The error bars represent the SEM.

Figure 42:
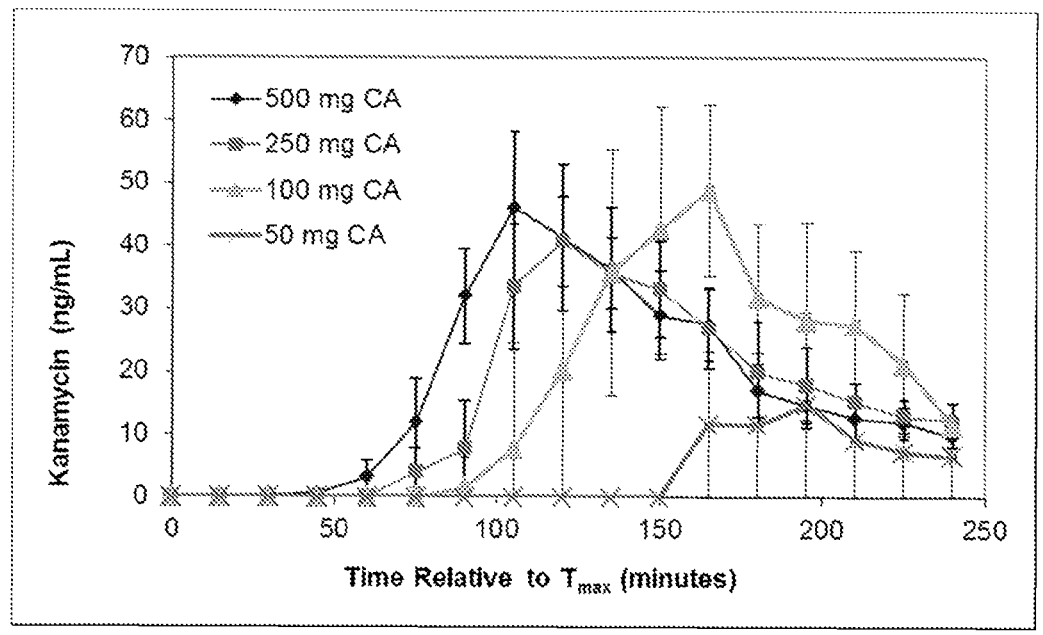
FIG. 42 is a graph showing Mean Absorption Profiles for Dogs Administered Kanamycin Formulated with 100 mg LLC and with Various Concentrations of CA.

A comparison for the mean absorption profiles for dogs administered kanamycin in VCAP PLUS™ capsules with 100 mg of LLC and various concentrations of CA (500 mg CA, JSV-003-005; 250 mg CA, JSV-003-052; 100 mg CA, JSV-003-053; 50 mg CA, JSV-003-054) are shown in FIG. 42. The data for each set of capsules were adjusted for the mean $T_{max}$. The error bars represent the SEM.

Mean Oral Absorption Profiles of Tobramycin

Figure 43:
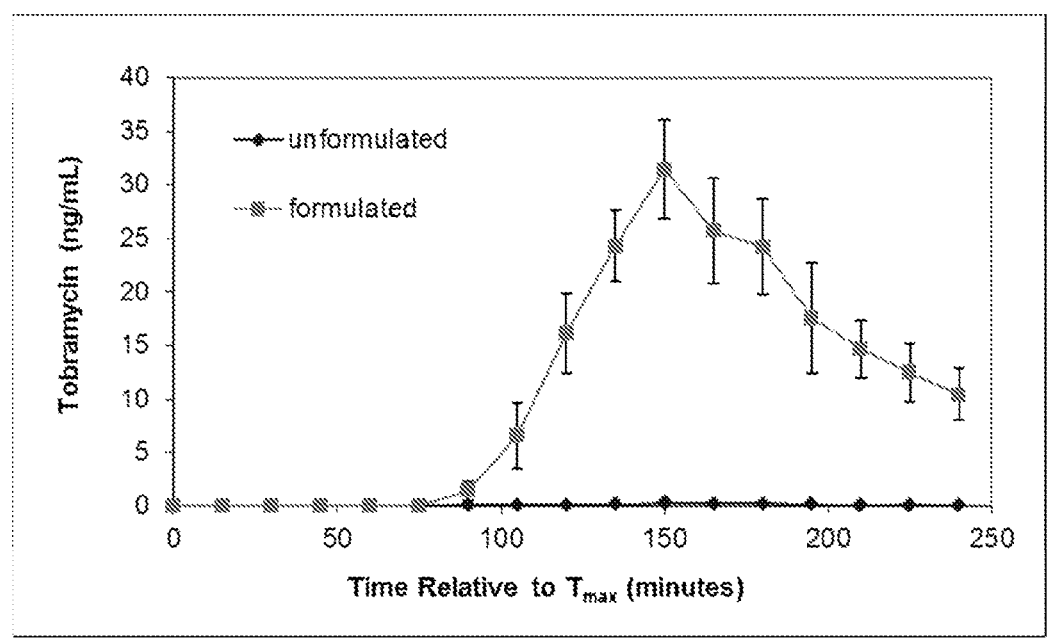
FIG. 43 is a graph showing Mean Absorption Profiles for Dogs Administered Unformulated and Formulated with CA and LLC Capsules Containing Tobramycin.

A comparison for the mean absorption profiles for dogs administered tobramycin in VCAP PLUS™ unformulated (0 mg CA and 0 mg LLC, JSV-003-050) capsules and formulated (500 mg CA and 100 mg LLC, JSV-003-051) are shown in FIG. 43. The data for each set of capsules were adjusted for the mean $T_{max}$. The error bars represent the SEM.

Discussion

Using a pharmaceutical composition of the present disclosure an oral bioavailability of 14% for kanamycin and 15% for tobramycin was achieved. The key excipients are CA and LLC. In Example 3, a concentration of at least 100 mg of CA is used in a pharmaceutical composition. In the present example, the VCAP PLUS™ capsules are preferable in a pharmaceutical composition to the DRCAPS™ capsules. The studies outlined in Example 3 serve as examples for BCS Class III aminoglycoside antibiotics. The examples of kanamycin and tobramycin are not intended to be limiting and are used as examples that a pharmaceutical composition of the present disclosure can improve oral bioavailability of BCS Class III molecules.

A feasibility study was carried out to evaluate the oral bioavailability and pharmacokinetics (PK) of the BCS Class 3 aminoglycoside bacterial antibiotics, kanamycin and tobramycin. The study design consisted of an intravenous (IV) phase and several oral phases dosed in Beagle dogs.

Orally administered kanamycin in an enteric-coated VCAP PLUS™ capsule containing 500 mg of citric acid (CA) and 100 mg lauroyl-L-carnitine (LLC) (formulation JSV-003-005) was given to 4 dogs and blood samples were collected up to 4 hours to determine plasma kanamycin concentrations over time. The dogs showed a mean $C_{max}$ of 428 ng/mL and a mean absolute bioavailability of 14%. Orally administered tobramycin in an enteric-coated VCAP PLUS™ capsule containing the same excipients (formulation JSV-003-051) were given to 8 dogs and blood samples were collected up to 4 hours to determine plasma tobramycin concentrations over time. These dogs showed a similar mean $C_{max}$ of 314 ng/mL and a similar mean absolute bioavailability of 15%.

TABLE 39

Summary of Mean Pharmacokinetic Parameters for Kanamycin and Tobramycin
Following Oral Administration of VCAP PLUS ™ Coated Capsules to Beagle Dogs (±SEM)

| Formulation | Key Excipients | N | $C_{max}$ (ng/mL) | $T_{max}$ (min) | $AUC_{(0-t)}$ (ng * min/mL) | % F |
|---|---|---|---|---|---|---|
| JSV-003-005 | 10 mg Kanamycin, 500 mg CA, 100 mg LLC | 4 | 428 (88) | 101 (13) | 46216 (6593) | 14.2 (2.0) |
| JSV-003-051 | 10 mg Tobramycin, 500 mg CA, 100 mg LLC | 8 | 314 (46) | 144 (20) | 25829 (4738) | 14.5 (2.7) |

Pharmacokinetic studies with coated and uncoated capsules containing kanamycin formulated with various amounts of CA were studied in dogs. The oral bioavailability of kanamycin from uncoated capsules formulated without CA and LLC was 2.8%, whereas the bioavailability of kanamycin from uncoated capsules formulated with 500 mg CA and 100 mg LLC was 12.4%. There was no significant change in the bioavailability of kanamycin orally delivered with enteric-coated capsules containing the same formulation. Furthermore, there was essentially no difference in bioavailability when the CA levels were reduced to 100 mg. Decreasing the amount of CA to 50 mg reduced the bioavailability of kanamycin to 2.6%.

TABLE 40

Summary of Mean Pharmacokinetic Parameters for Kanamycin Following Oral
Administration of Vcap Plus (Coated and Uncoated) Capsules to Beagle Dogs (±SEM)

| Formulation | Key Excipients | N | $C_{max}$ (ng/mL) | $T_{max}$ (min) | $AUC_{(0-t)}$ (ng * min/mL) | % F |
|---|---|---|---|---|---|---|
| JSV-003-038 | 0 mg CA, 0 mg LLC, uncoated | 6 | 67 (9) | 118 (18) | 9167 (983) | 2.8 (0.3) |
| JSV-003-039 | 500 mg CA, 100 mg LLC, uncoated | 6 | 390 (82) | 38 (9) | 40257 (7693) | 12.4 (2.4) |
| JSV-003-005 | 500 mg CA, 100 mg LLC, coated | 4 | 428 (88) | 101 (13) | 46216 (6593) | 14.2 (2.0) |
| JSV-003-052 | 250 mg CA, 100 mg LLC, coated | 3 | 408 (72) | 125 (22) | 36970 (10465) | 11.4 (3.2) |
| JSV-003-053 | 100 mg CA, 100 mg LLC, coated | 3 | 489 (196) | 160 (10) | 40336 (18038) | 12.4 (5.5) |
| JSV-003-054 | 50 mg CA, 100 mg LLC, coated | 3[1] | 147 (147) | 195 (NA) | 8573 (8573) | 2.6 (2.6) |

[1]Only one dog out of three showed detectable blood levels.

Studies were also performed with DRCAPS™ containing 10 mg kanamycin, 100 mg LLC and two concentrations of CA. These dogs did not show as high a level of oral bioavailability. Results for these two studies are presented below.

TABLE 41

Summary of Mean Pharmacokinetic Parameters for Kanamycin Following Oral
Administration of DR Capsules to Beagle Dogs (±SEM)

| Formulation | Key Excipients | N | $C_{max}$ (ng/mL) | $T_{max}$ (min) | AUC(0-t) (ng * min/mL) | % F |
|---|---|---|---|---|---|---|
| JSV-003-010 | 500 mg CA, 100 mg LLC | 4 | 208 (88) | 131 (54) | 29879 (12061) | 9.2 (4.0) |
| JSV-003-041 | 250 mg CA, 100 mg LLC | 5 | 364 (104) | 66 (14) | 34582 (8443) | 10.6 (2.6) |

Studies with tobramycin comparing unformulated (0 mg CA and 0 mg LLC) and formulated (500 mg CA and 100 mg LLC) VCAP PLUS™ capsules are summarized below. The oral bioavailability of tobramycin was 15% which is similar to that of kanamycin, as expected based on similar molecular weight and structure.

TABLE 42

Summary of Mean Pharmacokinetic Parameters for Tobramycin Following Oral Administration of Enteric-Coated VCAP PLUS ™ Capsules to Beagle Dogs (mean data (±SEM) are presented)

| Formulation | Key Excipients | N | $C_{max}$ (ng/mL) | $T_{max}$ (min) | AUC(0-t) (ng * min/mL) | % F |
|---|---|---|---|---|---|---|
| JSV-003-050 | 0 mg CA, 0 mg LLC | 8[1] | 3 (1) | 145 (35) | 270 (140) | 0.15 (0.08) |
| JSV-003-051 | 500 mg CA, 100 mg LLC | 8 | 314 (46) | 144 (20) | 25829 (4738) | 14.5 (2.7) |

[1]Only three out of eight dogs responded with detectable blood levels.

EXAMPLE 4

Tigecycline in Dogs

Materials
Animals and Test Article

Adult beagle dogs weighing approximately 9 to 15 kg were used in the study. The animals were housed at Sinclair Research Center, Columbia, either individually or in pairs in over-sized dog runs. Primary enclosures were as specified in the USDA Animal Welfare Act (9 CFR Parts 1, 2 and 3) and as described in the Guide for the Care and Use of Laboratory Animals (National Academy Press, Washington, D.C., 1996). A 12-hour light/12-hour dark photoperiod was maintained. Room temperature was set to be maintained between approximately 20±5° C. Relative humidity was monitored but not controlled. Animal room and pen cleaning were performed according to the testing facility (Sinclair) SOPs.

TEKLAD™ Certified Canine Diet was provided once daily in amounts (~400 grams) appropriate for the size and age of the animals. Tap water was available ad libitum via automatic watering device or water bowls. Animals were fasted overnight prior to drug administration and throughout the blood collection. Information on the test article, tigecycline, is listed in Table 43.

TABLE 43

Test Article Information

| Item | Compound Name | Catalog Number | Batch/Lot Number | Supplier |
|---|---|---|---|---|
| Test Article | Tigecycline | S-1403 | 5140301 | Selleck Chemical Co. |

Methods
Doses and Route of Administration

Doses are expressed in terms of free net tigecycline content. Intravenous doses of tigecycline were administered as bolus injections at a dose of 1.0 mg/mL. Oral dosing of enteric-coated capsules was accomplished by administering them to the back of the dog's mouth, followed by a chase of 5 mL water to ensure swallowing. Details of dosing and formulation composition for the primary feasibility assessments are summarized in Table 43.

TABLE 44

Capsule Composition, Dose and Number of Dogs[1,2]

| Formulation | Study Number | CA[3] (mg) | LLC[4] (mg) | PROSOLV ™[5] (mg) mg/capsule | Tigecycline (mg) | Target Dose (mg/kg) | n |
|---|---|---|---|---|---|---|---|
| JSV-003-007 | SC424 | 489 | 98 | 65 | 15 | 1.25 | 8 |
| JSV-003-008 | SC424 | — | — | 482 | 14 | 1.25 | 8 |
| JSV-003-032 | SC430 | 465 | 93 | 48 | 28 | 2.50 | 5 |
| JSV-003-033 | SC430 | 476 | 96 | 35 | 43 | 3.75 | 5 |
| JSV-003-034 | SC430 | — | — | 450 | 25 | 2.50 | 3 |

[1]Capsule composition was calculated by multiplying the average powder content by the percentage of each component in the powder blend
[2]Target Dose assumes 12 kg average dog body weight at time of dosing
[3]Citric acid DC F20, Jungbunzlauer, Unigene lot # AF659
[4]Lauroyl-L-Carnitine, custom synthesis, Lonza, Unigene lot # AF946
[5]PROSOLV ™ SMCC HD90, JRS Pharma, Unigene lot# AF602

Study Design and Sample Collection

Adult female Beagle dogs, weighing 9-15 kg were used in the oral and IV studies. Dogs were fasted overnight before the beginning of each study. Water was provided ad libitum. On the day of the study, one pre-dose blood sample of 3 mL was collected from each animal. Subsequently, each group of animals was dosed based on the protocol, i.e. either IV, or PO by capsule.

After administration of the drug, 3 mL blood samples were collected from the brachial vein at various time-points up to 1140 minutes (24 hours) post-administration, depending on the study duration. Blood samples were collected into new heparinized monovette sampling syringes. The samples were placed on ice before being centrifuged for 10 minutes at approximately 2750 rpm at 2-8° C. Each tube was labeled with the dog ID # and time-point, and they were stored at −20° C. pending shipment.

Analytical Procedure for Tigecycline

The quantitative determination of tigecycline in dog plasma was performed using an HPLC assay using UV detection at 350 nm. Minocycline (VWR international) was used as an internal standard. Sample processing/clean-up of plasma samples was carried out offline by protein precipitation with acidified acetonitrile using 0.5% trifluoroacetic acid (TFA).

The HPLC system consisted of Shimadzu SIL-HTc HPLC system equipped with dual Shimadzu LC-10ADvp isopumps, a Shimadzu CTO-10ASvp column temperature controller and a Shimadzu SPD-10Avp variable wavelength detector. The chromatographic separation was based on Li et al. with some notable differences (See Li et al., 2004, Quantitation of tigecycline, a novel glycylcycline, by liquid chromatography. *J. Chromatography B.* 811:225-229). HPLC separation was achieved on a reversed phase column (Phenomenex Luna C18(2), μm, 150×4.6 mm, part number: 00E-4252-E0), using an initial isocratic phase, following by gradient elution of tigecycline. Mobile phase A consisted of 23 mM phosphate buffer pH 2.5 with 4 mM 1-octanesulfonic acid, while mobile phase B consisting of 90% acetonitrile, 10% water, with 2 mM 1-octanesulfonic acid. The time program started isocratic at 25% mobile phase B for 6 minutes, followed by a linear increase in mobile phase B to 35% over the next 8 minutes (14 minutes), followed by re-equilibration to 25% mobile phase B for an additional 4 minutes. The total runtime was 18 minutes per sample. The mobile phase flow rate was 1.2 mL/min. Detection was performed using the SPD-10Avp variable wavelength detector set at 350 nm, with a sensitivity of 0.001 aufs.

Both unknown samples and calibration standards (tigecycline in pooled dog plasma) were treated by protein precipitation with acidified (0.5% TFA v/v) acetonitrile spiked with internal standard. The samples were then centrifuged under refrigeration at 13k rpm for 5 minutes. The supernatant was taken and the liquid removed to dryness under nitrogen in a turbovap. The dried extract was reconstituted in 60 μL of mobile phase A and the suspension was further centrifuged at 5k rpm for 5 minutes to pellet any insoluble matter. The resulting supernatant was then injected onto the LC.

The unknown concentration in dog plasma samples was determined by interpolation of the peak area ratios of analyte:internal standard versus the ratio of their nominal concentrations into the regression line obtained from calibration standards spiked in pooled dog plasma. No regression weighting was used for the calculations. The method was demonstrated to be linear to 0.05 μg/mL (defined LOQ). The calibration curve covered the range of 0.05 μg/mL to 5 μg/mL.

It should be noted however, that when the method was transferred to an older HPLC system (equipped with a Shimadzu SCT-10Avp system controller and SIL-10A auto-injector), the time program was further altered such that the gradient went to 38% mobile phase B to account to system design changes. All other parameters remained unchanged.

TABLE 45

RP-HPLC Analytical Method for Tigecycline in Dog Plasma

| Parameter | RP-HPLC Method |
|---|---|
| Column | Phenomenex LUNA ™ C18(2) |
| | 5 μm, 150 × 4.6 mm |
| | Part number: F00-4252-E0 |
| Column Temperature | 40° C. |
| Flow Rate | 1.2 mL/min |
| Detection Wavelength | 350 nm |
| Injection Volume | 50 μL |
| Mobile Phase A | 23 mM phosphate buffer pH 2.5 |
| | 4 mM 1-octanesulfonic acid |
| Mobile Phase B | 90% Acetonitrile (v/v) |
| | 10% Water (v/v) |
| | 2 mM 1-octanesulfonic acid |
| Time Program | 0-6 min: 25% B |
| | 6-14 min: linear to 35% B |
| | 14-18 min: 25% B |
| Total Runtime | 18 minutes |
| Standard Curve | 0.05-5.0 μg/mL |
| Sample Preparation | PPT: 0.5% TFA (v/v) in Acetonitrile |
| | Spin: 13k rpm 5 min |
| | Evaporate to dryness |
| | Reconstitute in 60 μL MP A |
| | Spin: 5k rpm 5 min |
| | Inject Supernatant |
| Internal Standard Prep (Minocycline) | 0.4 μg/mL in ppt solution |

Pharmacokinetic Data Handling

Tigecycline PK parameters for individual dogs were calculated using non-compartmental analysis with PK Functions for Microsoft Excel. The maximum plasma concentration ($C_{max}$) values and their times of occurrence ($T_{max}$) were obtained directly from the plasma concentration vs. time profiles. The areas under the plasma concentration-time curves ($AUC_{last}$) were estimated with the linear trapezoidal rule, by adding all the area portions under the curve from time zero to the time of the last observed plasma concentration.

Results

Plasma Tigecycline Following IV Administration (SC427, SC431)

The mean $C_{max}$ for plasma tigecycline at a target dose of 0.08 mg/kg was 79.1 ng/mL and was observed at a mean time ($T_{max}$) of 5 minutes (0.08 hrs). Tigecycline was measurable through 4 hours as expected based on a reported single dose half-life of approximately 20 hours in humans. The mean $AUC_{(0-t)}$ was 72.4 ng*hr/mL.

When the target dose was increased to 0.42 mg/kg, the mean C. increased to 335 ng/mL, which was also observed at $T_{max}$ of 5 minutes. In both studies, there is a clear biphasic disposition of tigecycline, which is initially extremely fast and reaches a steady state by approximately 30 minutes. The mean $AUC_{(0-t)}$ was 411 ng*hr/mL.

TABLE 46

Summary of Tigecycline IV Pharmacokinetic Parameters in Beagle Dogs Administered a Single 1 mg Dose Formulated in PBS (SC427)

| | Dog Number | | | | | |
|---|---|---|---|---|---|---|
| | 5220 | 5221 | 5222 | Mean | SD | % CV |
| | Tigecycline Plasma Concentration (ng/mL) | | | | | |
| Time (min) | | | | | | |
| 5 | 85.98 | 66.27 | 85.18 | 79.14 | 11.16 | 14.10 |
| 10 | 38.77 | 23.92 | 33.00 | 31.90 | 7.48 | 23.46 |
| 15 | 26.49 | 19.85 | 20.60 | 22.32 | 3.64 | 16.29 |
| 20 | 27.70 | 21.11 | 29.60 | 26.14 | 4.46 | 17.06 |
| 30 | 17.57 | 17.14 | 13.86 | 16.19 | 2.03 | 12.55 |
| 40 | 14.30 | 11.51 | 21.58 | 15.80 | 5.20 | 32.89 |
| 60 | 13.52 | 12.49 | 14.50 | 13.51 | 1.00 | 7.43 |
| 90 | 11.21 | 8.90 | 13.98 | 11.36 | 2.54 | 22.40 |
| 120 | 11.55 | 8.80 | 12.96 | 11.10 | 2.12 | 19.06 |
| 360 | 0.00 | 0.00 | 3.45 | 1.15 | 1.99 | 173.21 |
| 1440 | 0.00 | 1.91 | 0.00 | 0.64 | 1.10 | 173.21 |
| Parameters | | | | | | |
| Dose (mg/kg)* | 0.08 | 0.08 | 0.08 | — | | |
| $C_{max}$ (ng/mL) | 85.98 | 66.27 | 85.18 | 79.14 | 11.16 | 14.10 |
| $T_{max}$ (min) | 5 | 5 | 5 | 5 | 0 | 0 |
| $AUC_{(0-t)}$ (ng * hr/mL) | 56.22 | 61.40 | 99.54 | 72.39 | 23.66 | 32.69 |

*Actual dog weights at the beginning of studies were not available. Assumed 12 kg dog weight.

TABLE 47

Summary of Tigecycline IV Pharmacokinetic Parameters in Beagle Dogs Administered a Single 5 mg Dose Formulated in PBS (SC431)

| | Dog Number | | | | | |
|---|---|---|---|---|---|---|
| | 5266 | 5267 | 5268 | Mean | SD | % CV |
| | Tigecycline Plasma Concentration (ng/mL) | | | | | |
| Time (min) | | | | | | |
| 5 | 335.66 | 250.27 | 419.13 | 335.02 | 84.43 | 25.20 |
| 10 | 197.55 | 139.27 | 151.11 | 162.64 | 30.80 | 18.94 |
| 15 | 122.10 | 78.10 | 131.69 | 110.63 | 28.58 | 25.83 |
| 20 | 117.20 | 67.21 | 98.92 | 94.44 | 25.30 | 26.79 |
| 30 | 102.81 | 49.42 | 76.33 | 76.19 | 26.70 | 35.04 |
| 40 | 71.95 | 43.23 | 66.47 | 60.55 | 15.25 | 25.18 |
| 60 | 65.49 | 32.46 | 49.22 | 49.06 | 16.52 | 33.67 |
| 90 | 59.88 | 30.78 | 51.58 | 47.41 | 14.99 | 31.61 |
| 120 | 53.23 | 25.94 | 47.69 | 42.29 | 14.43 | 34.12 |
| 360 | 26.14 | 0.00 | 23.29 | 16.48 | 14.34 | 87.04 |
| 1440 | 0.00 | 0.00 | 0.00 | 0.00 | 0.00 | 0.00 |
| Parameters | | | | | | |
| Dose (mg/kg)* | 0.42 | 0.42 | 0.42 | — | | |
| $C_{max}$ (ng/mL) | 335.66 | 250.27 | 419.13 | 335.02 | 84.43 | 25.20 |
| $T_{max}$ (min) | 5 | 5 | 5 | 5 | 0 | 0 |
| $AUC_{(0-t)}$ (ng * hr/mL) | 568.95 | 153.68 | 509.94 | 410.86 | 224.67 | 54.68 |

*Actual dog weights at the beginning of studies were not available. Assumed 12 kg dog weight.

TABLE 48

Summary of Mean Tigecycline IV Pharmacokinetic Parameters in Beagle Dogs (% CV)

| Study | Dose (mg/kg) | N | $C_{max}$ (ng/mL) | $T_{max}$ (min) | AUC (0-t) (ng * hr/mL) |
|---|---|---|---|---|---|
| Study 1 (SC427) | 0.08 | 3 | 79.1 (14.1) | 5 (0) | 72.4 (32.7) |
| Study 2 (SC431) | 0.42 | 3 | 335 (25.2) | 5 (0) | 411 (54.7) |

Plasma Tigecycline Following PO Administration (SC424, SC430)

Tigecycline was administered orally in enteric-coated capsules either formulated with 500 mg coated CA (Citrocoat DC F20, Jungbunzlauer), 100 mg LLC, and silicified microcrystalline cellulose (PROSOLV™) as a filler, or unformulated with only filler. The capsules were enterically coated using a standard preclinical protocol to 10% weight gain. Two studies were conducted. In study SC424, tigecycline was administered either formulated or unformulated, both at a target 15 mg dose, to 8 dogs each. Study SC430 consisted of dosing 30 mg tigecycline, both formulated (n=5) and unformulated (n=3), and included an additional 45 mg formulated arm (n=5) to study dose escalation affects.

Pharmacokinetic data demonstrate no exposure in either the 15 mg, or 30 mg unformulated arms from studies SC424, or SC430, respectively, while all formulated doses resulted in appreciable exposure in both studies. Oral dosing of 15 mg formulated tigecycline demonstrated a mean $C_{max}$ of 75.5 ng/mL, a mean $AUC_{(0-t)}$ of 133 ng*hr/mL and a mean absolute % F of 12.2%. Pharmacokinetic results for individual dogs demonstrated a range of approximately 2 to 30% F. Tigecycline administration at higher doses and with plasma sampling over 24 hours demonstrated increases in both $C_{max}$ and $AUC_{(0-t)}$ with dose. Dosing at 45 mg tigecycline resulted in a mean $C_{max}$ of 177 ng/mL, a mean $AUC_{(0-t)}$ of 574 ng*hr/mL and a mean absolute % F of 15.5%. The mean T. was reproducible over all studied formulations.

TABLE 49

Summary of Tigecycline Pharmacokinetic Parameters in Beagle Dogs Administered a Single PO 15 mg Unformulated, Enteric-Coated Capsule (SC424)

| | Dog Number† | | | | | | Mean | SD | % CV |
|---|---|---|---|---|---|---|---|---|---|
| | 5196 | 5197 | 5198 | 5199 | 5200 | 5201 | | | |
| | Tigecycline Plasma Concentration (ng/mL) | | | | | | | | |
| Time (min) | | | | | | | | | |
| 15 | 0.00 | 0.00 | 0.00 | 0.00 | 0.00 | 0.00 | 0.00 | 0.00 | 0.00 |
| 30 | 0.00 | 0.00 | 0.00 | 0.00 | 0.00 | 0.00 | 0.00 | 0.00 | 0.00 |
| 45 | 0.00 | 0.00 | 0.00 | 0.00 | 0.00 | 0.00 | 0.00 | 0.00 | 0.00 |
| 60 | 0.00 | 0.00 | 0.00 | 0.00 | 0.00 | 0.00 | 0.00 | 0.00 | 0.00 |
| 75 | 0.00 | 0.00 | 0.00 | 0.00 | 0.00 | 0.00 | 0.00 | 0.00 | 0.00 |
| 90 | 0.00 | 0.00 | 0.00 | 0.00 | 0.00 | 0.00 | 0.00 | 0.00 | 0.00 |
| 105 | 0.00 | 0.00 | 0.00 | 0.00 | 0.00 | 0.00 | 0.00 | 0.00 | 0.00 |
| 120 | 0.00 | 0.00 | 0.00 | 0.00 | 0.00 | 0.00 | 0.00 | 0.00 | 0.00 |
| 135 | 0.00 | 0.00 | 0.00 | 0.00 | 0.00 | 0.00 | 0.00 | 0.00 | 0.00 |

TABLE 49-continued

Summary of Tigecycline Pharmacokinetic Parameters in Beagle Dogs Administered a Single PO 15 mg Unformulated, Enteric-Coated Capsule (SC424)

| | Dog Number[†] | | | | | | | | % |
|---|---|---|---|---|---|---|---|---|---|
| | 5196 | 5197 | 5198 | 5199 | 5200 | 5201 | Mean | SD | CV |
| | Tigecycline Plasma Concentration (ng/mL) | | | | | | | | |
| 150 | 0.00 | 0.00 | 0.00 | 0.00 | 0.00 | 0.00 | 0.00 | 0.00 | 0.00 |
| 165 | 0.00 | 0.00 | 0.00 | 0.00 | 0.00 | 0.00 | 0.00 | 0.00 | 0.00 |
| 180 | 0.00 | 0.00 | 0.00 | 0.00 | 0.00 | 0.00 | 0.00 | 0.00 | 0.00 |
| 195 | 0.00 | 0.00 | 0.00 | 0.00 | 0.00 | 0.00 | 0.00 | 0.00 | 0.00 |
| 210 | 0.00 | 0.00 | 0.00 | 0.00 | 0.00 | 0.00 | 0.00 | 0.00 | 0.00 |
| 225 | 0.00 | 0.00 | 0.00 | 0.00 | 0.00 | 0.00 | 0.00 | 0.00 | 0.00 |
| 240 | 0.00 | 0.00 | 0.00 | 0.00 | 0.00 | 0.00 | 0.00 | 0.00 | 0.00 |
| Parameters | | | | | | | | | |
| Dose (mg/kg)* | 1.25 | 1.25 | 1.25 | 1.25 | 1.25 | 1.25 | — | | |
| $C_{max}$ (ng/mL) | 0.00 | 0.00 | 0.00 | 0.00 | 0.00 | 0.00 | 0.00 | 0.00 | 0.00 |
| $T_{max}$ L (min) | — | — | — | — | — | — | — | — | — |
| $AUC_{(0-t)}$ (ng * hr/mL) | 0.00 | 0.00 | 0.00 | 0.00 | 0.00 | 0.00 | 0.00 | 0.00 | 0.00 |
| % F | 0.00 | 0.00 | 0.00 | 0.00 | 0.00 | 0.00 | 0.00 | 0.00 | 0.00 |

*Actual dog weights at the beginning of studies were not available. Assumed 12 kg dog weight.

[†]Although the initial study protocol indicated N = 8, only 6 dogs were analyzed. Dogs 5202 and 5203 were omitted from analysis.

TABLE 50

Summary of Tigecycline Pharmacokinetic Parameters in Beagle Dogs Administered a Single PO 30 mg Unformulated, Enteric-Coated Capsule (SC430)

| | Dog Number | | | | | |
|---|---|---|---|---|---|---|
| | 5263 | 5264 | 5265 | Mean | SD | % CV |
| | Tigecycline Plasma Concentration (ng/mL) | | | | | |
| Time (min) | | | | | | |
| 0.0 | 0.00 | 0.00 | 0.00 | 0.00 | 0.00 | 0.00 |
| 0.3 | 0.00 | 0.00 | 0.00 | 0.00 | 0.00 | 0.00 |
| 0.7 | 0.00 | 0.00 | 0.00 | 0.00 | 0.00 | 0.00 |
| 1.0 | 0.00 | 0.00 | 0.00 | 0.00 | 0.00 | 0.00 |
| 1.3 | 0.00 | 0.00 | 0.00 | 0.00 | 0.00 | 0.00 |
| 1.7 | 0.00 | 0.00 | 0.00 | 0.00 | 0.00 | 0.00 |
| 2.0 | 0.00 | 0.00 | 0.00 | 0.00 | 0.00 | 0.00 |
| 2.3 | 0.00 | 0.00 | 0.00 | 0.00 | 0.00 | 0.00 |
| 2.7 | 0.00 | 0.00 | 0.00 | 0.00 | 0.00 | 0.00 |
| 3.0 | 0.00 | 0.00 | 0.00 | 0.00 | 0.00 | 0.00 |
| 3.3 | 0.00 | 0.00 | 0.00 | 0.00 | 0.00 | 0.00 |
| 3.7 | 0.00 | 0.00 | 0.00 | 0.00 | 0.00 | 0.00 |
| 4.0 | 0.00 | 0.00 | 0.00 | 0.00 | 0.00 | 0.00 |
| 4.5 | 0.00 | 0.00 | 0.00 | 0.00 | 0.00 | 0.00 |
| 5.0 | 0.00 | 0.00 | 0.00 | 0.00 | 0.00 | 0.00 |
| 5.5 | 0.00 | 0.00 | 0.00 | 0.00 | 0.00 | 0.00 |
| 6.0 | 0.00 | 0.00 | 0.00 | 0.00 | 0.00 | 0.00 |
| 8.0 | 0.00 | 0.00 | 0.00 | 0.00 | 0.00 | 0.00 |
| 10.0 | 0.00 | 0.00 | 0.00 | 0.00 | 0.00 | 0.00 |
| 24.0 | 0.00 | 0.00 | 0.00 | 0.00 | 0.00 | 0.00 |
| Parameters | | | | | | |
| Dose (mg/kg)* | 2.5 | 2.5 | 2.5 | — | | |
| $C_{max}$ (ng/mL) | 0.00 | 0.00 | 0.00 | 0.00 | 0.00 | 0.00 |
| $T_{max}$ (min) | — | — | — | — | — | — |
| $AUC_{(0-t)}$ (ng * hr/mL) | 0.00 | 0.00 | 0.00 | 0.00 | 0.00 | 0.00 |
| % F | 0.00 | 0.00 | 0.00 | 0.00 | 0.00 | 0.00 |

*Actual dog weights at the beginning of studies were not available Assumed 12 kg dog weight.

TABLE 51

Summary of Tigecycline Pharmacokinetic Parameters in Beagle Dogs Administered a Single 15 mg PO, Enteric-Coated Capsule Formulated with 500 mg CA and 100 mg LLC (SC424)

| | Dog Number | | | | | | | | | | |
|---|---|---|---|---|---|---|---|---|---|---|---|
| | 5188 | 5189 | 5190 | 5191 | 5192 | 5193 | 5194 | 5195 | Mean | SD | % CV |
| | Tigecycline Plasma Concentration (ng/mL) | | | | | | | | | | |
| Time (min) | | | | | | | | | | | |
| 0 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.00 | 0.00 |
| 30 | 0.00 | 0.00 | 0.00 | 0.00 | 0.00 | 0.00 | 0.00 | 0.00 | 0.00 | 0.00 | 0.00 |
| 45 | 0.00 | 0.00 | 67.62 | 0.00 | 0.00 | 0.00 | 0.00 | 0.00 | 8.45 | 23.91 | 282.84 |
| 60 | 0.00 | 0.00 | 102.56 | 0.00 | 0.00 | 46.91 | 0.00 | 0.00 | 18.68 | 37.66 | 201.55 |
| 75 | 67.41 | 0.00 | 124.71 | 0.00 | 0.00 | 44.94 | 97.41 | 34.28 | 46.09 | 47.48 | 103.02 |
| 90 | 72.72 | 0.00 | 131.62 | 0.00 | 0.00 | 58.36 | 74.02 | 93.83 | 53.82 | 49.47 | 91.92 |
| 105 | 72.29 | 0.00 | 114.31 | 94.07 | 12.21 | 59.07 | 56.48 | 73.28 | 60.21 | 38.42 | 63.81 |
| 120 | 68.67 | 0.00 | 102.31 | 83.74 | 15.40 | 42.92 | 47.02 | 51.68 | 51.47 | 33.73 | 65.54 |
| 135 | 58.13 | 0.00 | 97.81 | 75.90 | 12.41 | 39.11 | 45.03 | 41.15 | 46.19 | 31.72 | 68.66 |
| 150 | 40.67 | 0.00 | 107.71 | 78.99 | 12.76 | 25.44 | 35.51 | 32.23 | 41.66 | 35.29 | 84.70 |
| 165 | 44.69 | 10.79 | 90.92 | 76.85 | 12.42 | 24.23 | 29.71 | 35.94 | 40.69 | 29.16 | 71.67 |
| 180 | 41.02 | 33.29 | 82.31 | 73.35 | 10.38 | 17.06 | 21.14 | 20.67 | 37.40 | 26.80 | 71.65 |
| 195 | 37.51 | 38.70 | 82.52 | 75.43 | 6.06 | 14.60 | 20.86 | 25.82 | 37.69 | 27.76 | 73.65 |
| 210 | 34.32 | 39.92 | 80.92 | 73.72 | 3.16 | 18.51 | 19.45 | 20.23 | 36.28 | 27.69 | 76.31 |
| 225 | 35.89 | 33.39 | 80.91 | 69.32 | 0.00 | 12.76 | 19.24 | 23.47 | 34.37 | 27.74 | 80.70 |
| 240 | 35.68 | 25.96 | 98.76 | 72.67 | 7.56 | 4.89 | 16.45 | 19.58 | 35.19 | 33.40 | 94.89 |
| Parameters | | | | | | | | | | | |
| Dose (mg/kg)* | 1.25 | 1.25 | 1.25 | 1.25 | 1.25 | 1.25 | 1.25 | 1.25 | — | | |

TABLE 51-continued

Summary of Tigecycline Pharmacokinetic Parameters in Beagle Dogs Administered a Single 15 mg PO, Enteric-Coated Capsule Formulated with 500 mg CA and 100 mg LLC (SC424)

| | Dog Number | | | | | | | | Mean | SD | % CV |
|---|---|---|---|---|---|---|---|---|---|---|---|
| | 5188 | 5189 | 5190 | 5191 | 5192 | 5193 | 5194 | 5195 | | | |
| | Tigecycline Plasma Concentration (ng/mL) | | | | | | | | | | |
| $C_{max}$ (ng/mL) | 72.72 | 39.92 | 131.62 | 94.07 | 15.40 | 59.07 | 97.41 | 93.83 | 75.51 | 48.70 | 64.50 |
| $T_{max}$ (min) | 90 | 210 | 90 | 105 | 120 | 105 | 75 | 90 | 111 | 38.31 | 34.63 |
| $AUC_{(0-t)}$ (ng * hr/mL) | 148 | 42 | 329 | 184 | 22 | 90 | 130 | 116 | 133 | 95.57 | 72.04 |
| % F[‡] | 13.6 | 3.9 | 30.3 | 17.0 | 2.0 | 8.3 | 12.0 | 10.6 | 12.2 | 8.80 | 72.04 |

*Actual dog weights at the beginning of studies were not available. Assumed 12 kg dog weight.
[‡]% F calculated from IV data generated from Study SC427.

TABLE 52

Summary of Tigecycline Pharmacokinetic Parameters in Beagle Dogs Administered a Single 30 mg PO, Enteric-Coated Capsule Formulated with 500 mg CA and 100 mg LLC (SC430)

| | Dog Number | | | | | Mean | SD | % CV |
|---|---|---|---|---|---|---|---|---|
| | 5253 | 5254 | 5255 | 5256 | 5257 | | | |
| | Tigecycline Plasma Concentration (ng/mL) | | | | | | | |
| Time (min) | | | | | | | | |
| 0.0 | 0.00 | 0.00 | 0.00 | 0.00 | 0.00 | 0.00 | 0.00 | 0.00 |
| 0.3 | 0.00 | 0.00 | 0.00 | 0.00 | 0.00 | 0.00 | 0.00 | 0.00 |
| 0.7 | 0.00 | 95.94 | 0.00 | 0.00 | 36.01 | 26.39 | 41.89 | 158.74 |
| 1.0 | 0.00 | 154.19 | 0.00 | 0.00 | 90.62 | 48.96 | 70.71 | 144.42 |
| 1.3 | 0.00 | 182.24 | 0.00 | 0.00 | 73.60 | 51.17 | 79.90 | 156.15 |
| 1.7 | 91.58 | 145.17 | 33.81 | 0.00 | 47.35 | 63.58 | 56.20 | 88.38 |
| 2.0 | 66.04 | 127.57 | 87.39 | NR | 53.01 | 83.50 | 32.62 | 39.06 |
| 2.3 | 76.54 | 118.71 | 120.08 | 0.00 | 45.11 | 72.09 | 51.04 | 70.81 |
| 2.7 | 55.33 | 107.93 | 87.68 | 0.00 | 44.38 | 59.06 | 41.61 | 70.44 |
| 3.0 | 44.24 | 96.41 | 76.21 | 0.00 | 32.59 | 49.89 | 37.67 | 75.51 |
| 3.3 | 42.97 | 87.87 | 48.94 | 0.00 | 32.16 | 42.39 | 31.67 | 74.73 |
| 3.7 | NR | 71.18 | 50.58 | 0.00 | NR | 40.59 | 36.63 | 90.24 |
| 4.0 | 33.78 | 65.95 | 48.33 | 0.00 | 35.01 | 36.61 | 24.23 | 66.19 |
| 4.5 | 34.53 | 61.09 | 38.99 | 0.00 | 33.07 | 33.54 | 21.88 | 65.24 |
| 5.0 | 33.82 | 63.28 | 34.27 | 0.00 | 27.47 | 31.77 | 22.53 | 70.93 |
| 5.5 | NR | 59.44 | 34.85 | 36.11 | 21.10 | 37.88 | 15.90 | 41.99 |
| 6.0 | 0.00 | NR | 28.57 | 36.53 | 19.76 | 21.21 | 15.71 | 74.08 |
| 8.0 | 0.00 | 0.00 | 18.56 | 0.00 | 17.77 | 7.27 | 9.95 | 136.99 |
| 10.0 | 0.00 | 0.00 | 0.00 | 0.00 | 12.91 | 2.58 | 5.77 | 223.61 |
| 24.0 | 0.00 | 0.00 | 0.00 | 0.00 | 0.00 | 0.00 | 0.00 | 0.00 |
| Parameters[†] | | | | | | | | |
| Dose (mg/kg)* | 2.5 | 2.5 | 2.5 | 2.5 | 2.5 | — | | |
| $C_{max}$ (ng/mL) | 91.58 | 182.24 | 120.08 | 36.53 | 90.62 | 121.13 | 42.97 | 35.47 |
| $T_{max}$ (min) | 1.7 | 1.3 | 2.3 | 6.0 | 1.0 | 1.6 | 0.57 | 35.95 |
| $AUC_{(0-t)}$ (ng * hr/mL) | 195 | 575 | 315 | 64 | 382 | 367 | 158.68 | 43.28 |
| % F[‡] | 7.9 | 23.3 | 12.8 | 2.6 | 15.5 | 14.9 | 6.44 | 43.28 |

*Actual dog weights at the beginning of studies were not available. Assumed 12 kg dog weight.
[†]Results reported excluding animal 5256
[‡]% F calculated from IV PK data generated under Study SC431

TABLE 53

Summary of Tigecycline Pharmacokinetic Parameters in Beagle Dogs Administered a Single 45 mg PO, Enteric-Coated Capsule Formulated with 500 mg CA and 100 mg LLC (SC430)

| | Dog Number | | | | | | | |
|---|---|---|---|---|---|---|---|---|
| | 5258 | 5259 | 5260 | 5261 | 5262 | Mean | SD | % CV |
| | Tigecycline Plasma Concentration (ng/mL) | | | | | | | |
| Time (min) | | | | | | | | |
| 0.0 | 0.00 | 0.00 | 0.00 | 0.00 | 0.00 | 0.00 | 0.00 | 0.00 |
| 0.3 | 0.00 | 0.00 | 0.00 | 0.00 | 0.00 | 0.00 | 0.00 | 0.00 |
| 0.7 | 0.00 | 0.00 | 0.00 | 0.00 | 0.00 | 0.00 | 0.00 | 0.00 |
| 1.0 | 133.63 | 127.65 | 0.00 | 20.73 | 0.00 | 56.40 | 68.33 | 121.15 |
| 1.3 | 153.06 | 78.69 | 0.00 | 59.87 | 0.00 | 58.32 | 63.63 | 109.10 |
| 1.7 | 138.33 | 46.66 | 0.00 | 157.62 | 163.14 | 101.15 | 73.51 | 72.67 |
| 2.0 | 116.10 | 43.10 | 44.20 | 149.31 | 367.01 | 143.94 | 132.93 | 92.35 |
| 2.3 | 87.32 | 39.82 | 79.71 | 114.76 | 216.56 | 107.63 | 66.53 | 61.82 |
| 2.7 | 78.26 | 33.22 | 79.21 | 102.49 | 199.64 | 98.56 | 61.82 | 62.73 |
| 3.0 | 74.06 | 31.63 | 62.12 | 98.25 | 116.52 | 76.52 | 32.79 | 42.85 |
| 3.3 | 69.50 | 33.98 | 49.17 | 63.91 | 126.80 | 68.67 | 35.31 | 51.41 |
| 3.7 | 62.36 | 33.14 | 38.96 | 55.89 | 119.77 | 62.02 | 34.42 | 55.49 |
| 4.0 | 54.31 | 21.63 | 32.14 | 46.68 | 103.81 | 51.71 | 31.76 | 61.41 |
| 4.5 | 58.85 | 16.87 | 21.77 | 47.61 | 99.47 | 48.91 | 33.24 | 67.96 |
| 5.0 | 48.38 | 20.56 | 33.56 | 45.61 | 104.91 | 50.60 | 32.30 | 63.82 |
| 5.5 | 44.74 | 19.45 | 21.25 | 50.62 | 76.57 | 42.53 | 23.53 | 55.33 |
| 6.0 | 36.76 | 13.66 | 13.38 | 34.52 | 77.87 | 35.24 | 26.29 | 74.59 |
| 8.0 | 27.89 | 10.52 | 6.37 | 20.09 | 49.82 | 22.94 | 17.20 | 75.00 |
| 10.0 | 22.19 | 0.00 | 4.77 | 12.09 | 44.75 | 16.76 | 17.75 | 105.88 |
| 24.0 | 0.00 | 0.00 | 0.00 | 0.00 | 0.00 | 0.00 | 0.00 | 0.00 |
| Parameters | | | | | | | | |
| Dose (mg/kg)* | 3.75 | 3.75 | 3.75 | 3.75 | 3.75 | — | | |
| $C_{max}$ (ng/mL) | 153.06 | 127.65 | 79.71 | 157.62 | 367.01 | 177.01 | 110.63 | 62.50 |
| $T_{max}$ (min) | 1.33 | 1.00 | 2.33 | 1.67 | 2.00 | 1.67 | 0.53 | 31.62 |
| $AUC_{(0-t)}$ (ng * hr/mL) | 682 | 232 | 237 | 546 | 1175 | 574 | 389 | 67.70 |
| % F‡ | 18.4 | 6.3 | 6.4 | 14.8 | 31.8 | 15.5 | 10.52 | 67.70 |

*Actual dog weights at the beginning of studies were not available. Assumed 12 kg dog weight.
‡% F calculated from IV PK data generated under Study SC431

TABLE 54

Mean Tigecycline Pharmacokinetic Parameters Following Oral Administration in Enteric Coated Capsules (% CV).

| Study | Formulation† | N | $C_{max}$ (ng/mL) | $T_{max}$ (min) | $AUC_{(0-t)}$ (ng * hr/mL) | % F‡ |
|---|---|---|---|---|---|---|
| Study 1 (SC424) | 15 mg Formulated | 8 | 75.5 (48.7) | 111 (38.3) | 133 (72.0) | 12.2 (72.0) |
| | 15 mg Unformulated | 6 | ND | — | — | 0.0 |
| Study 2 (SC430) | 30 mg Unformulated | 3 | ND | — | — | 0.0 |
| | 30 mg Formulated* | 4* | 121 (35.5)* | 95 (36.0)* | 367 (43.3)* | 14.9 (43.3)* |
| | 45 mg Formulated | 5 | 177 (62.5) | 100 (31.6) | 574 (67.7) | 15.5 (67.7) |

*Results reported excluding animal 5256
†Formulated capsules targeted 500 mg CA and 100 mg LLC
‡% F calculated based on that study's respective IV arm Discussion These studies demonstrated the feasibility of improving the oral bioavailability of tigecycline, a BCS Class III antibiotic, using the combination of CA and LLC in beagle dogs. These formulations were delivered in enterically coated capsules and provide a valuable preclinical proof of concept to support potential future clinical development. Example 1 conducted in rats using an ID injection model demonstrates the seemingly synergistic role of the combination of CA and LLC as absorption enhancing excipients. The studies outlined in Example 1 also demonstrated the importance of formulation pH in enabling oral % F of tigecycline. While valuable from a mechanistic standpoint, Example 1 used a liquid vehicle to directly deliver tigecycline to the absorptive surface and was designed specifically to remove the potential confounder of the solid to liquid transition (disintegration and dissolution) of a solid dosage form, a primary factor in enabling bioavailability and controlling the variability inherent to enabling formulations.

Figure 44:
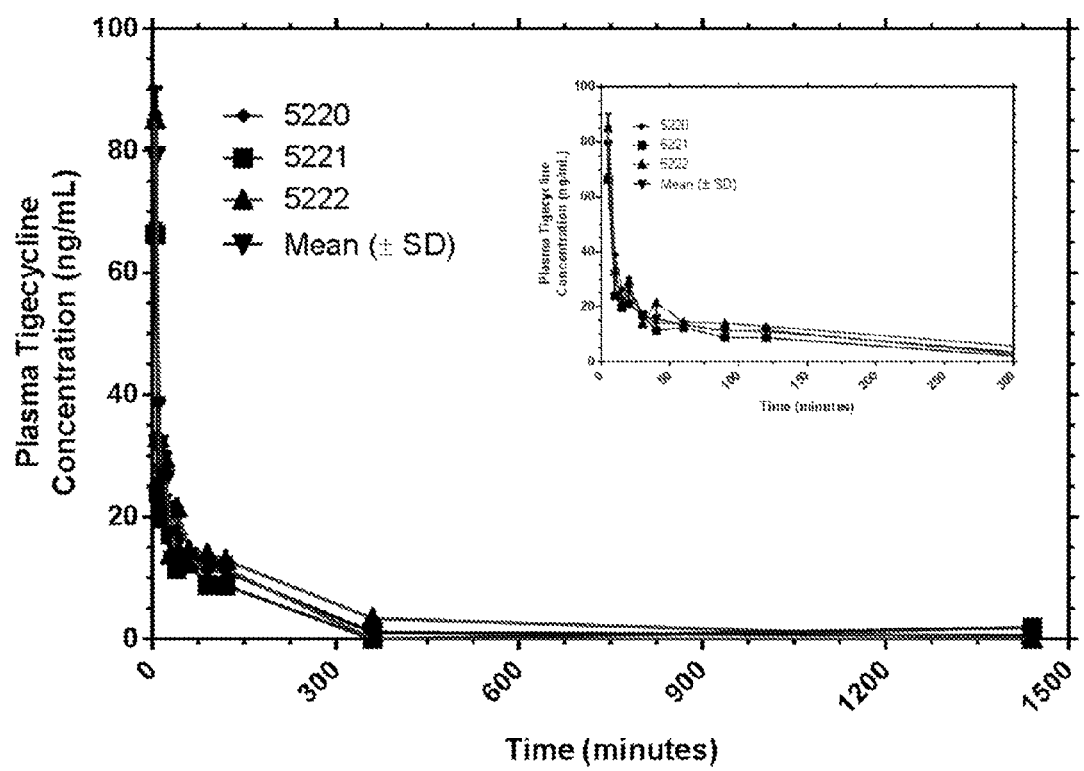
FIG. 44 is a graph showing Individual and Mean (±SD) Plasma Tigecycline Concentration in Beagle Dogs Following a Single 1 mg (0.08 mg/kg) IV Bolus Injection (SC427).
Figure 45:
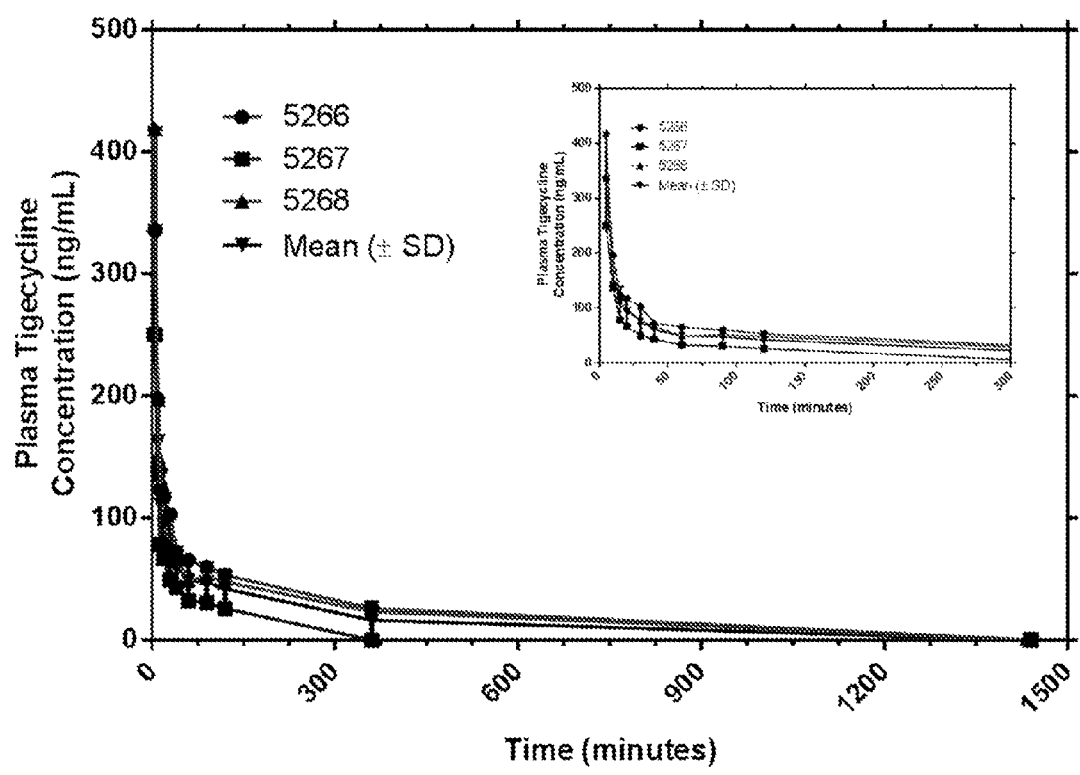
FIG. 45 is a graph showing Individual and Mean (±SD) Plasma Tigecycline Concentration in Beagle Dogs Following a Single 5 mg (0.42 mg/kg) IV Bolus Injection (SC431).
Figure 46:
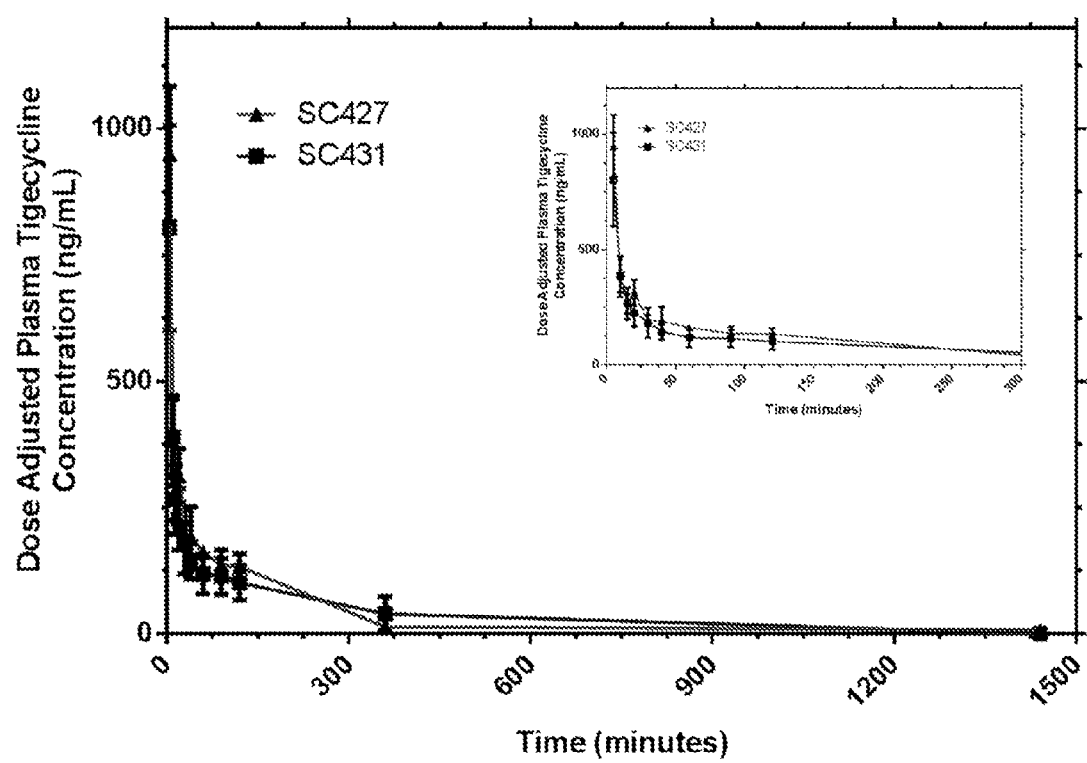
FIG. 46 is a graph showing Dose Adjusted Mean Plasma Tigecycline Concentrations in Beagle Dogs Following Single IV Bolus Injections (SC427 and SC431).
Figure 47:
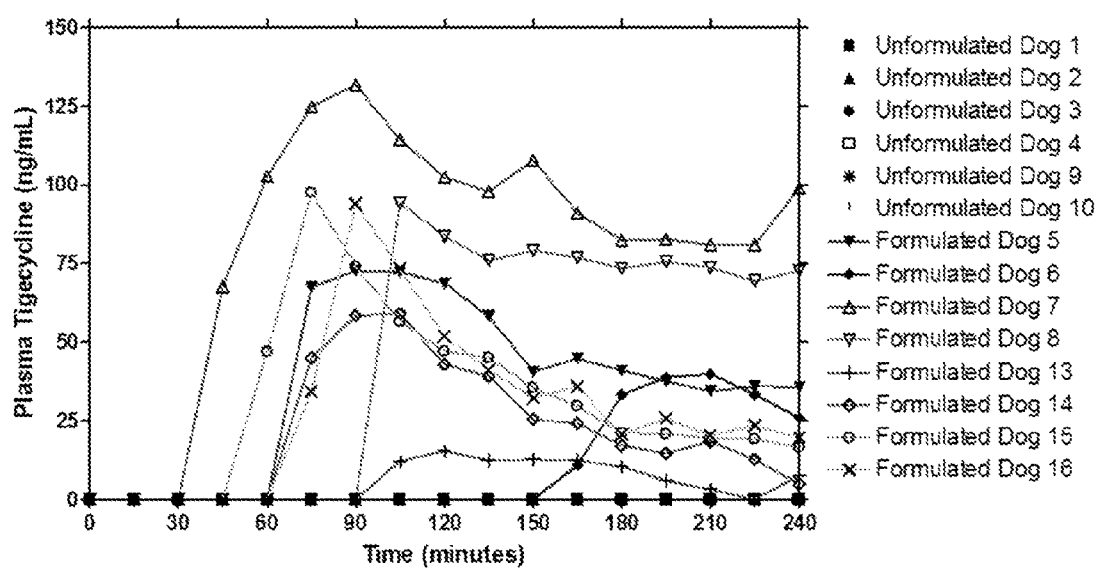
FIG. 47 is a graph showing Individual Plasma Tigecycline Concentration in Beagle Dogs Following a Single 15 mg (1.25 mg/kg) PO Enteric-Coated Capsule Either Unformulated, or Formulated with 500 mg CA and 100 mg LLC (SC424).
Figure 48:
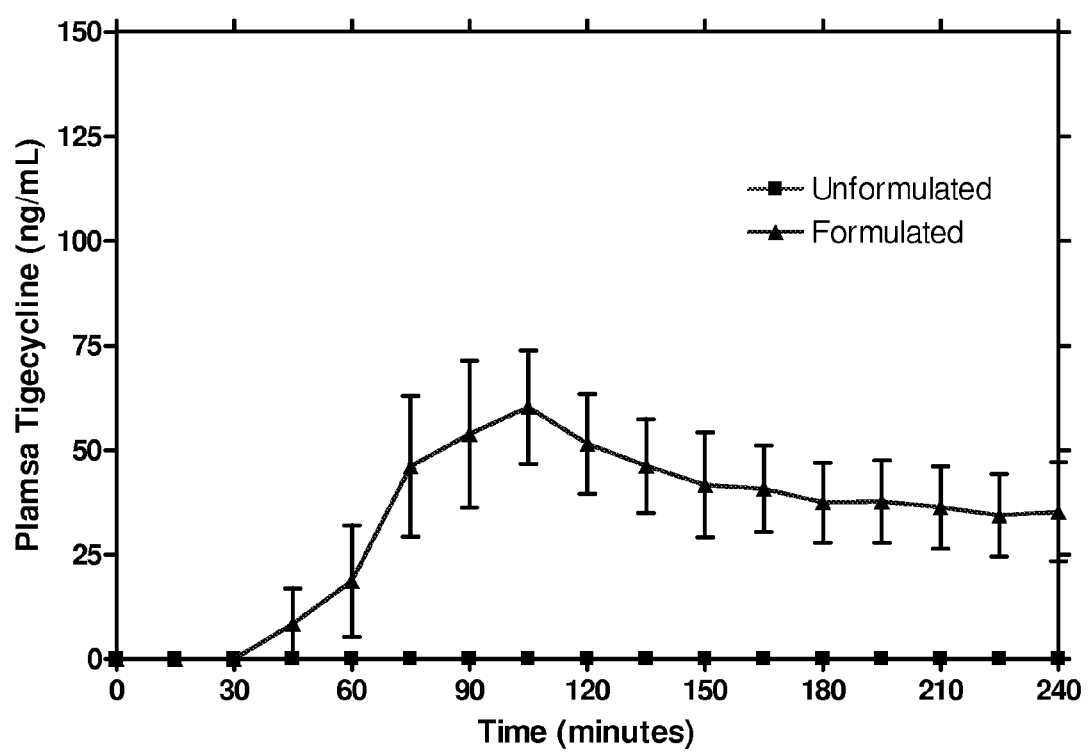
FIG. 48 is a graph showing Mean (±SD) Plasma Tigecycline Concentration in Beagle Dogs Following a Single 15 mg (1.25 mg/kg) PO Enteric-Coated Capsule Either Unformulated, or Formulated with 500 mg CA and 100 mg LLC (SC424).
Figure 49:
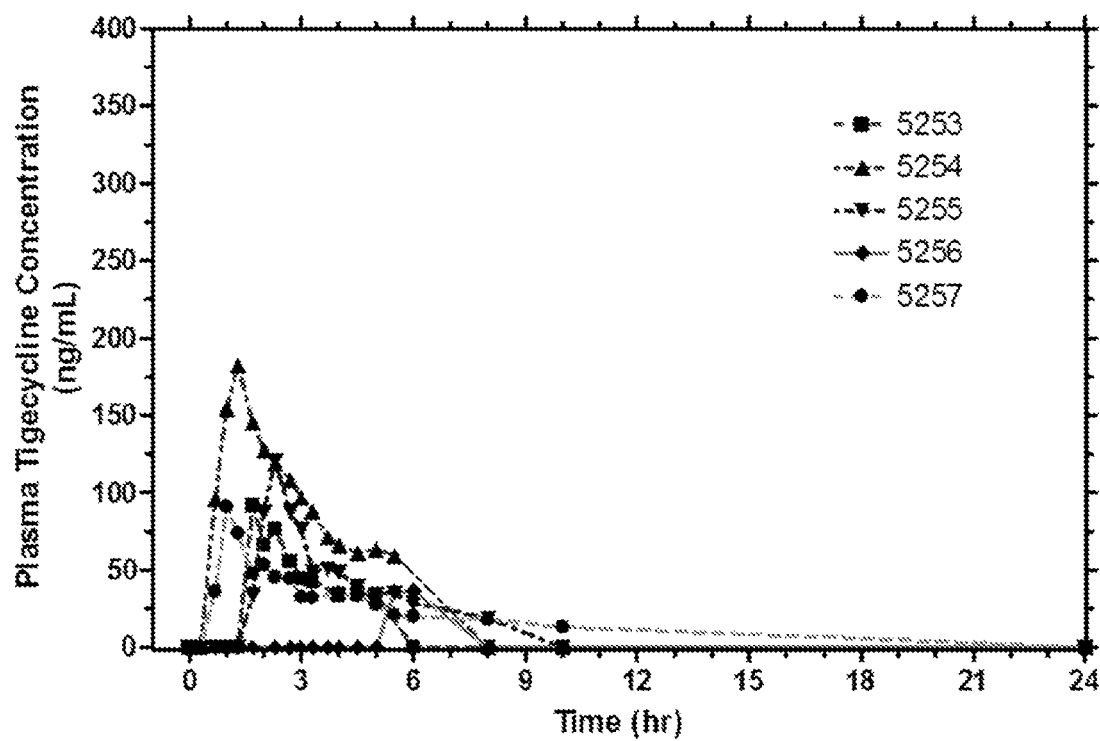
FIG. 49 is a graph showing Individual Plasma Tigecycline Concentration in Beagle Dogs Following a Single 30 mg (2.5 mg/kg) PO Enteric-Coated Capsule Formulated with 500 mg CA and 100 mg LLC (SC430).
Figure 50:
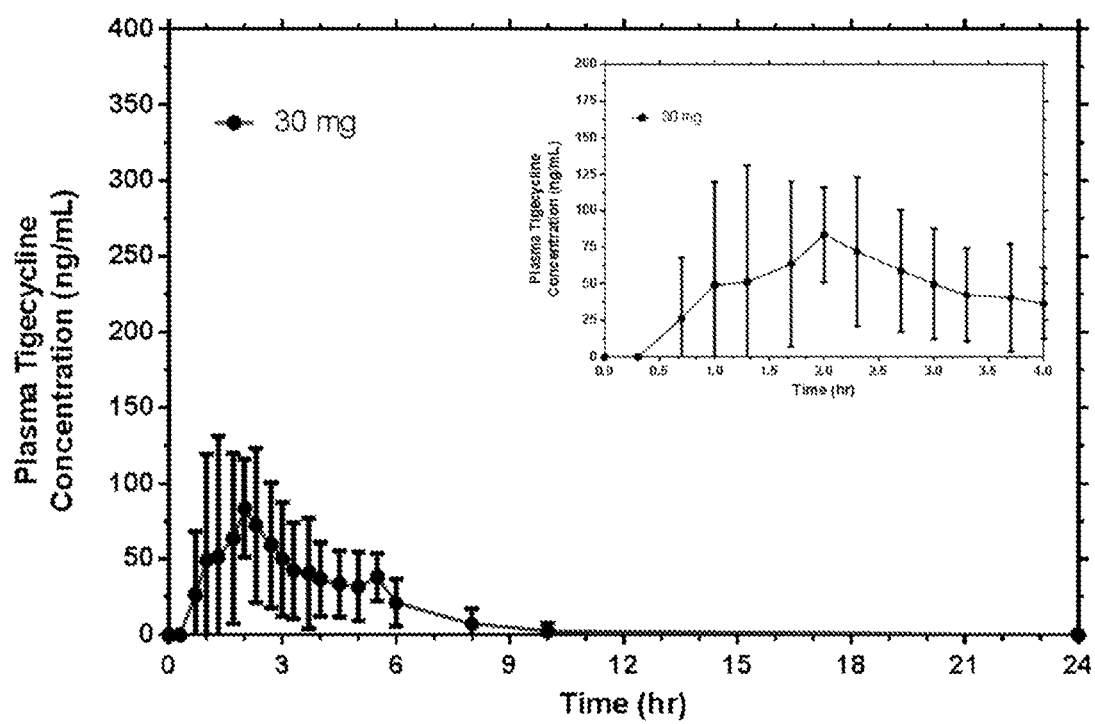
FIG. 50 is a graph showing Mean (±SD) Plasma Tigecycline Concentration in Beagle Dogs Following a Single 30 mg (2.5 mg/kg) PO Enteric-Coated Capsule Formulated with 500 mg CA and 100 mg LLC (SC430).
Figure 51:
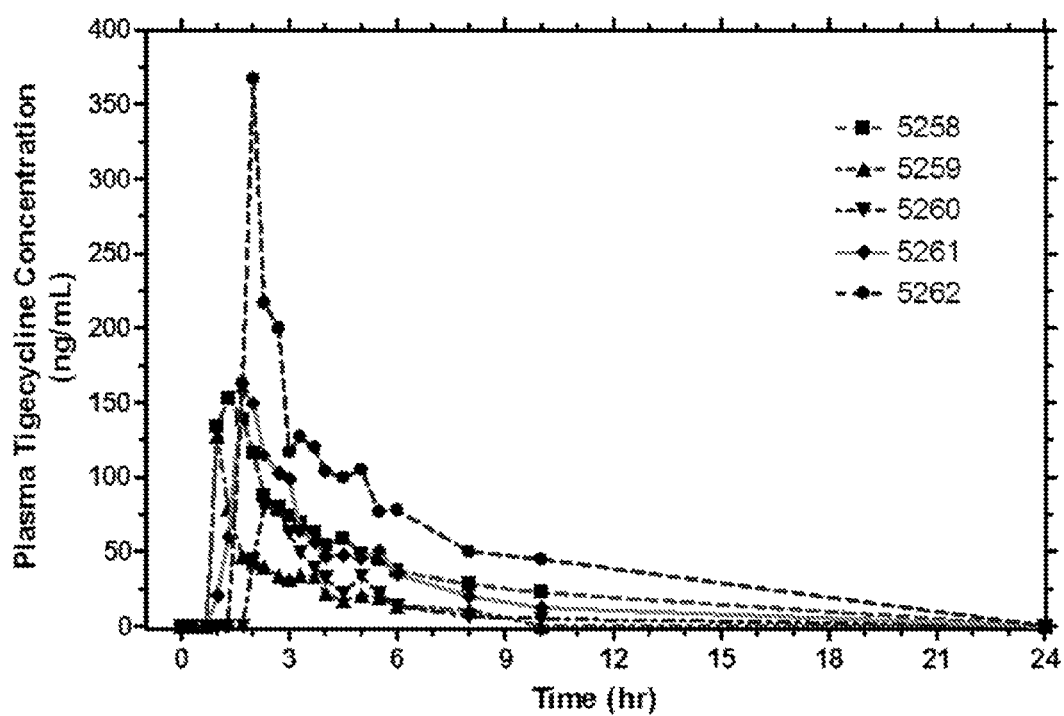
FIG. 51 is a graph showing Individual Plasma Tigecycline Concentration in Beagle Dogs Following a Single 45 mg (3.75 mg/kg) PO Enteric-Coated Capsule Formulated with 500 mg CA and 100 mg LLC (SC430).
Figure 52:
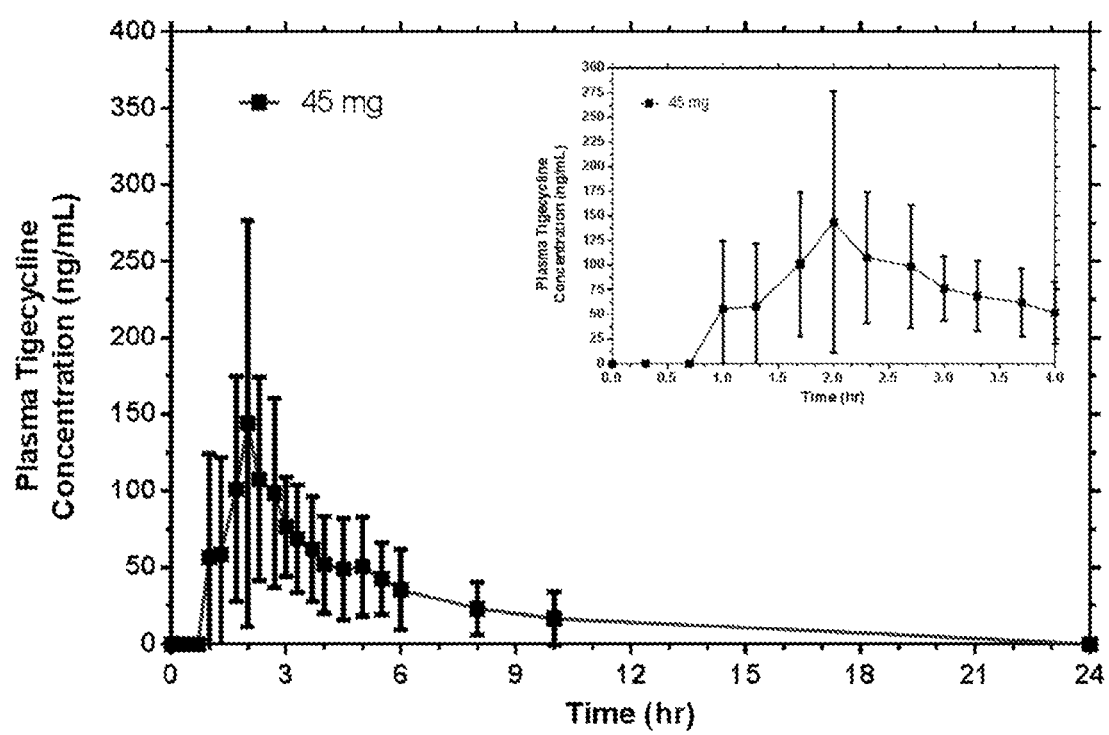
FIG. 52 is a graph showing Mean (±SD) Plasma Tigecycline Concentration in Beagle Dogs Following a Single 45 mg (3.75 mg/kg) PO Enteric-Coated Capsule Formulated with 500 mg CA and 100 mg LLC (SC430).
Figure 53:
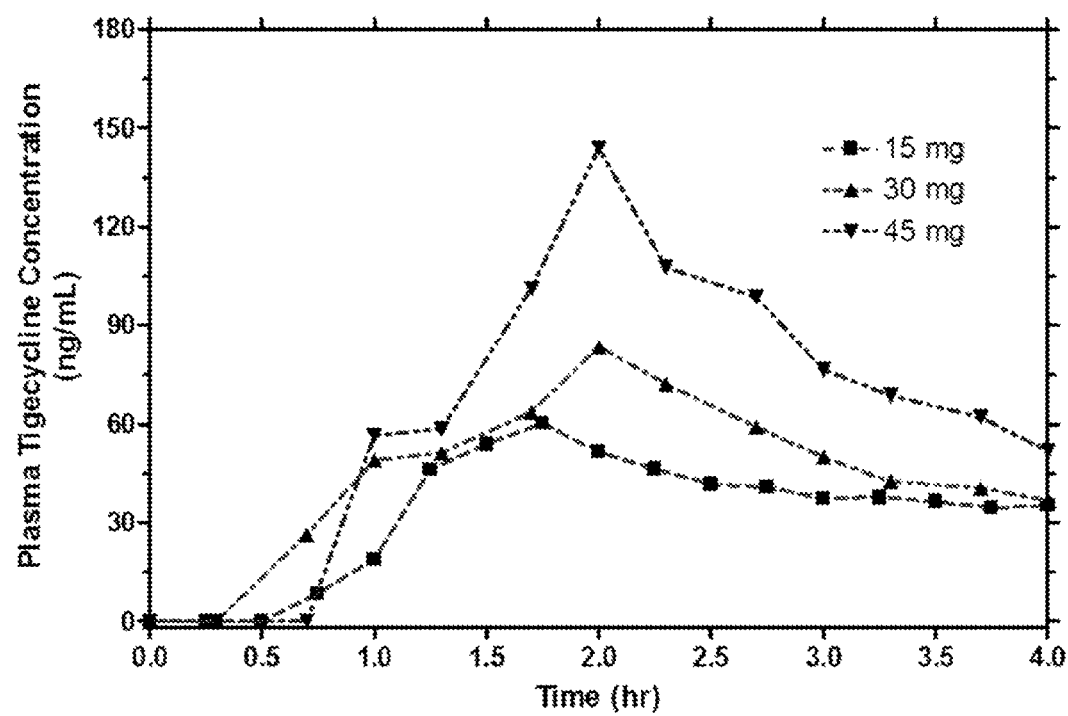
FIG. 53 is a graph showing Mean Plasma Tigecycline Concentrations in Beagle Dogs Following a Single PO Enteric-Coated Capsule Formulated with 500 mg CA and 100 mg LLC (SC424 and SC430). (Note the time scale has been adjusted for comparison as SC424 sampled to 4 hours, while SC430 sampled to 24 hours).

Intravenous administration of tigecycline resulted in an expected biphasic, first order plasma concentration curve. Given that one way to overcome low exposure upon dosing a BCS Class III compound is by increasing the local concentration available for absorption (i.e., the dose), the IV PK profile was determined at two concentrations. While overall exposure was directly dependent on the dose (FIG. 44 and FIG. 45), the dose adjusted PK curves were virtually identical (FIG. 46).

Rat studies (Example 1) also demonstrated the utility of higher concentrations of CA in enabling higher tigecycline exposure. In those studies, 400 mM CA, pH 3.5, in combination with 26 mM LLC resulted in approximately 21% bioavailability. It was hypothesized that CA could act to disrupt potential tetracycline:bile salt interactions, which lead to tigecycline precipitation. To this end, these formulations were prepared with a target of 500 mg coated CA, which is on the high end of the concentration range typically studied, both clinically and preclinically. Moreover, these studies did not explore the effects of lower CA concentrations, as data from the rat studies would immediately suggest lower net exposure. These studies did however explore the effects of dose escalation on absolute exposure.

Peroral dosing of 15 mg (target 1.25 mg/kg) tigecycline with 500 mg CA and 100 mg LLC resulted in a mean $C_{max}$ of 75.5 ng/mL, a mean $AUC_{(0-t)}$ of 133 ng*hr/mL and a mean absolute % F of 12.2%. Dosing at 45 mg tigecycline resulted in a mean $C_{max}$ of 177 ng/mL, a mean $AUC_{(0-t)}$ of 574 ng*hr/mL and a mean absolute bioavailability of 15.5%. The mean $T_{max}$, at approximately 100 minutes, was reproducible over all studied oral formulations. Interestingly, while exposure was linear with respect to both $C_{max}$ and AUC, it was less than dose proportional with respect to both $C_{max}$ and $AUC_{(0-4HR)}$ (Table 55). These observations could be a function of a limited absorption window (by design), as the percent difference from predicted (based on results from the 15 mg dose) at the 30 mg dose was lower than that for the 45 mg dose. An alternate hypothesis could be that other factors, such as bile salt or transporter interactions, are playing a role in inhibiting absorptive flux; i.e. as the dose is increased, tigecycline is in such excess that there isn't sufficient CA to inhibit either transporter effects, or precipitation with bile salt complexes. More likely, however, is that the biopharmaceutical properties of the molecule itself result in an observable saturation effect due to extensive tissue distribution.

Figure 54:
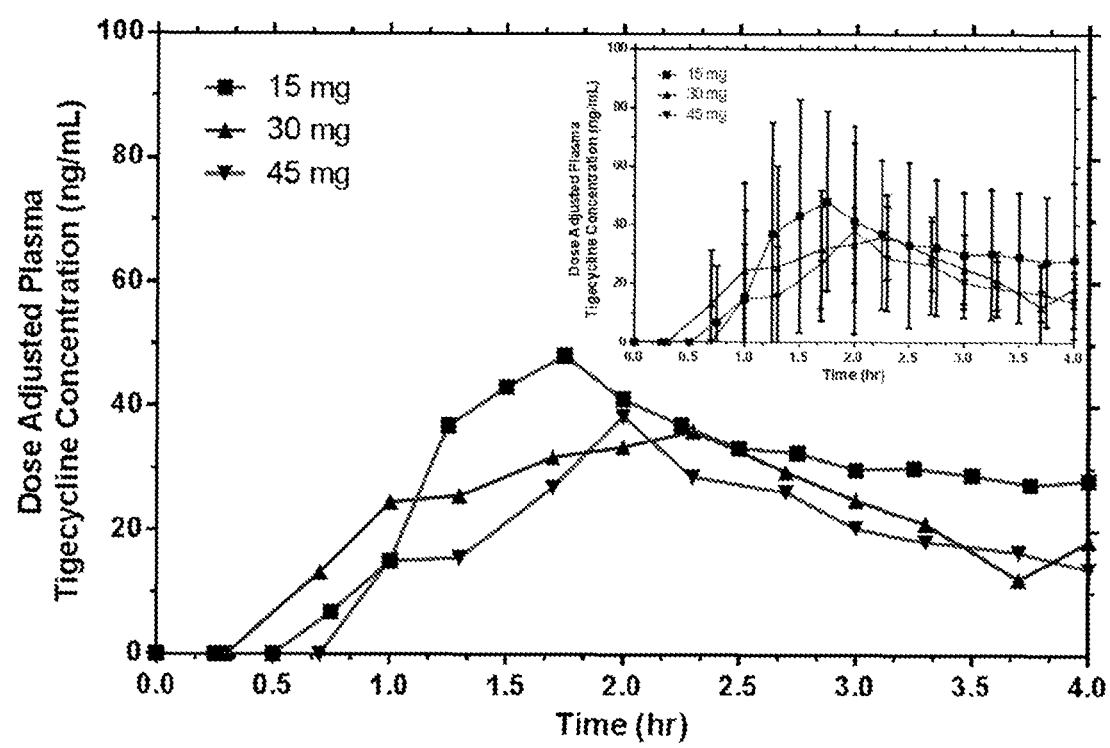
FIG. 54 is a graph showing Mean Dose Adjusted Plasma Tigecycline Concentrations in Beagle Dogs Following a Single PO Enteric-Coated Capsule Formulated with 500 mg CA and 100 mg LLC (SC424 and SC430). Note the time scale has been adjusted for comparison as SC424 sampled to 4 hours, while SC430 sampled to 24 hours.
Figure 55:
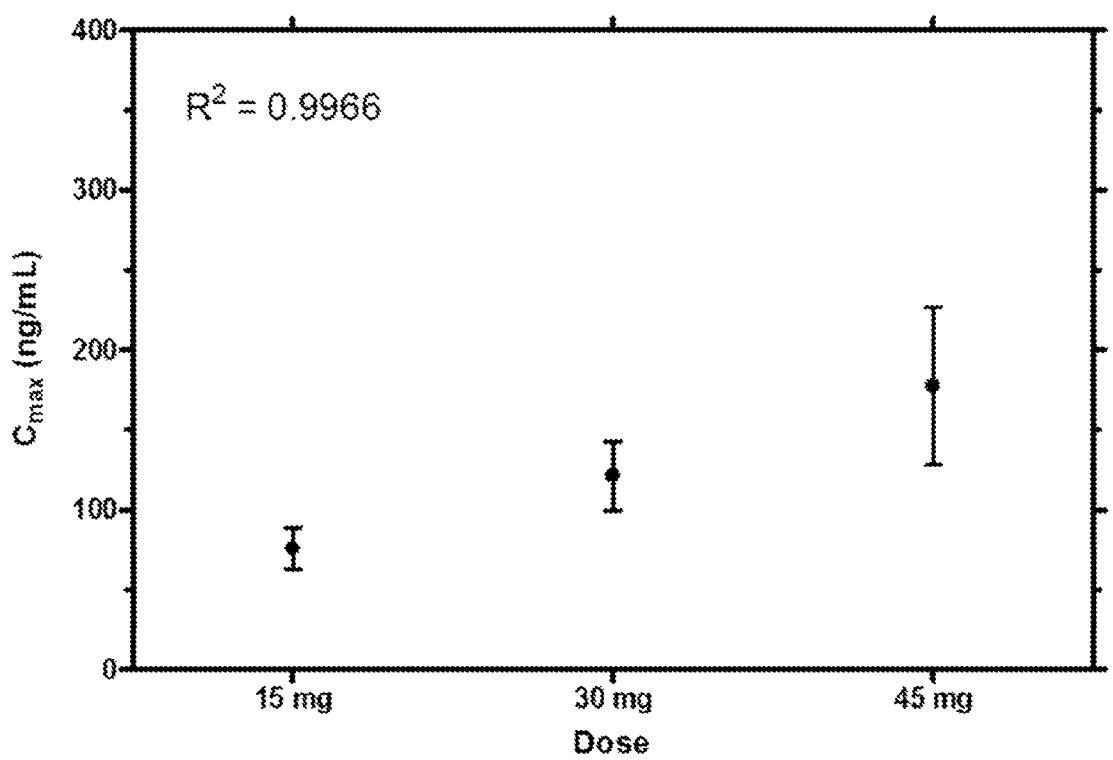
FIG. 55 is a graph showing Dose Linearity With Respect to $C_{max}$ in Beagle Dogs Following a Single PO Enteric-Coated Capsules Formulated with 500 mg CA and 100 mg LLC. Note the time scale has been adjusted for comparison as SC424 sampled to 4 hours, while SC430 sampled to 24 hours.
Figure 56:
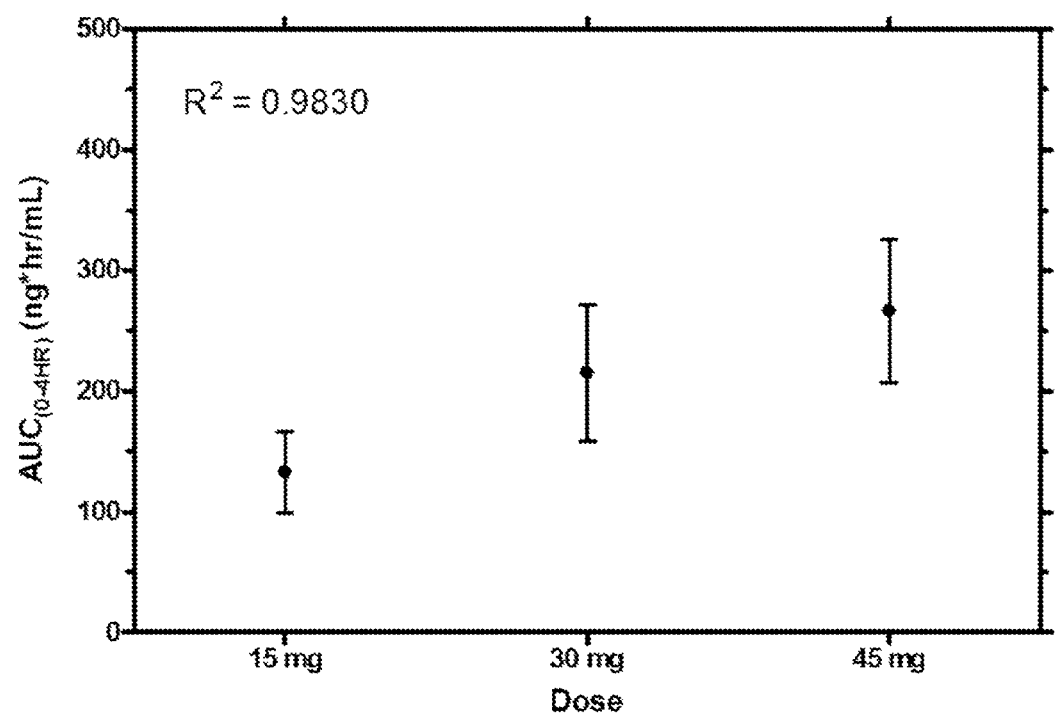
FIG. 56 is a graph showing Dose Linearity With Respect to $AUC_{(0-4HR)}$ in Beagle Dogs Following a Single PO Enteric-Coated Capsules Formulated with 500 mg CA and 100 mg LLC. Note the time scale has been adjusted for comparison as SC424 sampled to 4 hours, while SC430 sampled to 24 hours.

Tigecycline does indeed exhibit a high tissue distribution. Coupled with a lack of metabolism, the low dose proportionality further suggests both insufficient absorption, as well as nonlinear clearance with respect to dose. In short, the dose relationship observed is a saturation effect, i.e. clearance decreases with respect to increasing dose, most likely due to tissue deposition commensurate with the high tissue distribution of tigecycline, which could be confounded by absorption issues at the higher doses. Further supporting this hypothesis is that no observable differences could be gleaned from the dose adjusted mean plasma profiles (FIG. 54). A relatively simple way to test this hypothesis would be to study the dose proportionality after single oral doses of tigecycline following a saturable IV infusion. Such a study would also benefit potential further clinical investigation as this could be foreseen as a potential product profile for orally administered tigecycline.

TABLE 55

Dose Proportionality of Tigecycline Pharmacokinetic Parameters Following Oral Administration in Enterically Coated Capsules[‡]

| Target Dose (mg) | Observed Mean $C_{max}$ (ng/mL) | Predicted Mean $C_{max}$ (ng/mL; % Difference)[†] | Observed $AUC_{(0-t)}$ (ng * hr/mL) | Predicted $AUC_{(0-t)}$ (ng * hr/mL; % Difference)[†] |
|---|---|---|---|---|
| 15 | 75.5 | — | 133 | — |
| 30 | 121* | 151 (−24.8) | 214* | 265 (−23.9) |
| 45 | 177 | 226 (−28.0) | 266 | 398 (−49.4) |

*Results reported excluding animal 5256
[†]Predicted values based on 15 mg results
[‡]Note the time scale has been adjusted for comparison as SC424 sampled to 4 hours, while SC430 sampled to 24 hours.

These studies demonstrate the feasibility of using the oral delivery technology for the BCS Class III small molecule tigecycline in the dog preclinical model. No tigecycline exposure was observed in dogs dosed with either 15 mg or 30 mg tigecycline capsules formulated in a microcrystalline cellulose filler. Administration of enterically coated capsules containing 15 mg tigecycline and formulated with 500 mg CA and 100 mg LLC resulted in a mean absolute % F of 12.2%. Increasing the dose linearly increased both $C_{max}$ and $AUC_{(0-t)}$, but exposure was not dose proportional. The mean bioavailability of 45 mg tigecycline formulated with 500 mg citric acid and 100 mg LLC resulted in a mean absolute % F of 15.5%.

The purpose of these studies was to investigate the oral bioavailability (% F) and pharmacokinetic (PK) profiles of orally administered tigecycline in beagle dogs. Two studies were conducted, each consisting of an intravenous (IV) phase and an oral phase with enteric-coated capsules containing formulated, or unformulated tigecycline. The studies differed in the doses administered and sampling timeframe.

In Study 1 (SC424 and SC427), tigecycline was administered as a 1 mg IV bolus injection to beagle dogs (n=3), as well as a 15 mg, enteric coated capsule arm. The capsule phase included 2 formulations, either formulated with citric acid (CA) and 3,0-lauroyl-L-carnitine (LLC), or unformulated (n=8 dogs each). Venous blood samples were collected up to 4 hours after dosing to determine plasma tigecycline concentrations with respect to time.

Study 2 (SC430 and SC431) was designed based on feedback from Study 1, and included a higher dose IV arm (5 mg per animal, n=3), as well as 30 mg and 45 mg formulated (n=5 each), enterically coated capsules and 30 mg unformulated (n=3), enterically coated capsules. The study also included 24 hours venous sampling to fully characterize the PK profiles upon single oral doses. Formulated arms in both studies included 500 mg CA and 100 mg LLC, while unformulated arms included the drug dispersed in a microcrystalline cellulose filler. These parameters were not varied between Study 1 and Study 2.

Pharmacokinetic data indicate that IV administered tigecycline exhibited a biphasic clearance, with an approximately proportional increase in both $C_{max}$ and $AUC_{(0-t)}$ upon increasing dose between Study 1 and Study 2 (1 mg vs. 5 mg). The mean $C_{max}$ was 79 ng/mL and 335 ng/mL, respectively, and the mean $AUC_{(0-t)}$ was 72.4 ng*hr/mL and 411 ng*hr/mL, respectively.

TABLE 56

Summary of Mean Tigecycline IV Pharmacokinetic Parameters in Beagle Dogs (% CV)

| Study | Dose (mg) | N | $C_{max}$ (ng/mL) | $T_{max}$ (min) | $AUC_{(0-t)}$ (ng * hr/mL) |
|---|---|---|---|---|---|
| Study 1 (SC427) | 1 | 3 | 79.1 (14.1) | 5 (0) | 72.4 (32.7) |
| Study 2 (SC431) | 5 | 3 | 335 (25.2) | 5 (0) | 411 (54.7) |

Oral administration of tigecycline formulated with microcrystalline cellulose (unformulated) and filled in enterically coated capsules at either 15 mg (Study 1), or 30 mg (Study 2) did not result in observable plasma exposure, while tigecycline formulated with 500 mg CA and 100 mg LLC demonstrated appreciable exposure at all doses in both studies. Orally administered tigecycline formulated at 15 mg with active excipients were dosed to 8 dogs, with plasma sampling occurring over 4 hours post-dose. Results demonstrate a mean C. of 75.5 ng/mL, a mean $AUC_{(0-t)}$ of 133 ng*hr/mL and a mean absolute % F of 12.2%. Tigecycline administration at higher doses and with plasma sampling over 24 hours demonstrated increases in both $C_{max}$ and $AUC_{(0-t)}$ with dose, but exposure was less than dose proportional, potentially due to a limited absorption window by design. Dosing at 45 mg tigecycline resulted in a mean $C_{max}$ of 177 ng/mL, a mean $AUC_{(0-t)}$ of 574 ng*hr/mL and a mean absolute % F of 15.5%. The mean $T_{max}$ was reproducible over all studied doses.

TABLE 57

Mean Tigecycline Pharmacokinetic Parameters Following Oral Administration in Enteric Coated Capsules (% CV)

| Study | Formulation[†] | N | $C_{max}$ (ng/mL) | $T_{max}$ (min) | $AUC_{(0-t)}$ (ng * hr/mL) | % F[‡] |
|---|---|---|---|---|---|---|
| Study 1 (SC424) | 15 mg Formulated | 8 | 75.5 (48.7) | 111 (38.3) | 133 (72.0) | 12.2 (72.0) |
| | 15 mg Unformulated | 8 | ND | — | — | 0.0 |
| Study 2 (SC430) | 30 mg Unformulated | 3 | ND | — | — | 0.0 |
| | 30 mg Formulated* | 4* | 121 (35.5)* | 95 (36.0)* | 367 (43.3)* | 14.9 (43.3)* |
| | 45 mg Formulated | 5 | 177 (62.5) | 100 (31.6) | 574 (67.7) | 15.5 (67.7) |

*Results reported excluding animal 5256
[†]Formulated capsules targeted 500 mg citric acid and 100 mg LLC
[‡]% F calculated based on that study's respective IV arm

EXAMPLE 5

Fenofibrate Solubility

Methods

Fenofibrate is a BCS class II compound and as such is insoluble in water. It has solubility of 1 mg/mL in ethanol, 30 mg/mL in DMF, 15 mg/mL in DMSO and 250 mcg/mL in 1:3 DMF:PBS pH 7.2

The solubility of fenofibrate in water was assessed at increasing concentrations of LLC from 0.0% w/v to 10.0% w/v. Excess fenofibrate was weighed into individual PP vials. Fenofibrate containing solutions were mixed at 125 rpm at 25° C. for 4 days. Dissolved fenofibrate was monitored by HPLC against a standard curve prepared in neat $CH_3CN$.

Results and Discussion

Figure 57:
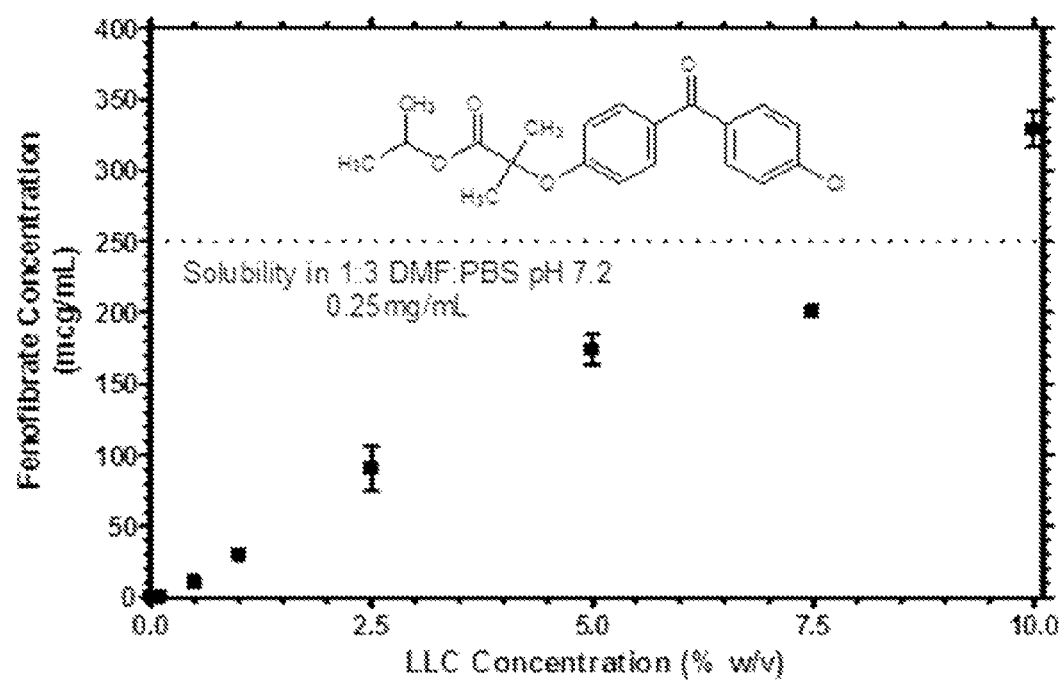
FIG. 57 is a graph showing Solubility of Fenofibrate with increasing concentrations of LLC.

Data shown in FIG. 57 indicate increased solubility of fenofibrate in water with increasing concentrations of LLC. The increased solubility of fenofibrate may indicate the utility of LLC in enhancing solubility of other class II molecules in water. LLC may be utilized in a composition of the present disclosure as a solubility enhancer.

The invention claimed is:

1. A solid oral dosage form comprising:
    a mixture comprising:
        a therapeutically effective amount of at least one active pharmaceutical compound classified as BCS Class III, wherein the compound does not include a peptide bond in the molecular structure of the compound;
        an absorption enhancer; and
        from 100 mg to 500 mg of coated citric acid particles, wherein the citric acid particles are coated with a water soluble coat that separates the citric acid from the active pharmaceutical compound, wherein, if the dosage form was added to ten milliliters of 0.1 M aqueous sodium bicarbonate solution, the pH of the solution would be acidified to a pH no higher than 5.5;
    an enteric coating; and
    a water soluble barrier positioned between the mixture and the enteric coating, thereby separating the mixture from the enteric coating,
    wherein oral administration results in a synergistic increase in systemic bioavailability of the active pharmaceutical compound when compared to the systemic bioavailability provided by administration of a solid dosage form containing an equal dose of the active pharmaceutical compound without the absorption enhancer and the citric acid.

2. The solid oral dosage form of claim 1, wherein the absorption enhancer is a combination of two or more absorption enhancers.

3. The solid oral dosage form of claim 1, wherein the absorption enhancer comprises a surface acting agent.

4. The solid oral dosage form of claim 3, wherein the surface acting agent is an acid soluble bile acid.

5. The solid oral dosage form of claim 1, wherein the absorption enhancer comprises an acylcarnitine.

6. The solid oral dosage form of claim 1, wherein the absorption enhancer comprises lauroyl carnitine.

7. The solid oral dosage form of claim 1, wherein the at least one active pharmaceutical compound classified as BCS Class III is an antibiotic or an antiviral compound.

8. The solid oral dosage form of claim 1, wherein the at least one active pharmaceutical compound classified as BCS Class III is an aminoglycoside.

9. The solid oral dosage form of claim 1, wherein the at least one active pharmaceutical compound is selected from the group consisting of tigecycline, zanamivir, kanamycin, and tobramycin.

10. A method of treating a bacterial infection in a subject in need thereof comprising orally administering a solid oral dosage form comprising:

a mixture comprising:

at least one active pharmaceutical, antibacterial, or antiviral compound classified as BCS Class III, wherein the compound does not include a peptide bond in the compound's molecular structure an absorption enhancer; and from 100 mg to 500 mg of coated citric acid particles, wherein the citric acid particles are coated with a water soluble coat that separates the citric acid from the at least one active compound, wherein, if the dosage form was added to ten milliliters of 0.1 M aqueous sodium bicarbonate solution, the pH of the solution would be lowered to no higher than 5.5;

an enteric coating; and a water soluble barrier positioned between the mixture and the enteric coating, thereby separating the mixture from the enteric coating, wherein oral administration results in a synergistic increase in systemic bioavailability of the active compound when compared to the systemic bioavailability provided by administration of a solid dosage form containing an equal dose of the active compound without the absorption enhancer and the citric acid.

11. The method of claim 10, wherein the infection is a gram-negative infection.

12. The method of claim 10, wherein the infection is a gram-positive infection.

13. The method of claim 10, wherein the at least one active compound is an antibiotic or an antiviral compound.

14. The method of claim 10, wherein the at least one active compound is an aminoglycoside.

15. The method of claim 10, wherein the at least one active compound is selected from the group consisting of tigecycline, zanamivir, kanamycin, and tobramycin.

16. The method of claim 10, wherein the absorption enhancer is a combination of two or more absorption enhancers.

17. The method of claim 10, wherein the absorption enhancer comprises an acylcarnitine.

18. The method of claim 10, wherein the absorption enhancer comprises lauroyl carnitine.

* * * * *